(12) United States Patent
Zenz-Olson et al.

(10) Patent No.: US 10,987,210 B2
(45) Date of Patent: Apr. 27, 2021

(54) MEDICAL IMPLANT DELIVERY SYSTEM AND RELATED METHODS

(71) Applicant: ROTATION MEDICAL, INC., Plymouth, MN (US)

(72) Inventors: Nathaniel Zenz-Olson, Blaine, MN (US); Nathaniel Tran, Lakeville, MN (US)

(73) Assignee: ROTATION MEDICAL, INC., Plymouth, MN (US)

( * ) Notice: Subject to any disclaimer, the term of this patent is extended or adjusted under 35 U.S.C. 154(b) by 132 days.

(21) Appl. No.: 16/211,761

(22) Filed: Dec. 6, 2018

(65) Prior Publication Data

US 2019/0175328 A1     Jun. 13, 2019

Related U.S. Application Data

(60) Provisional application No. 62/595,737, filed on Dec. 7, 2017.

(51) Int. Cl.
| | |
|---|---|
| *A61F 2/08* | (2006.01) |
| *A61B 17/064* | (2006.01) |
| *A61B 17/10* | (2006.01) |
| *A61B 17/00* | (2006.01) |
| *A61F 2/00* | (2006.01) |

(52) U.S. Cl.
CPC .......... *A61F 2/0805* (2013.01); *A61B 17/064* (2013.01); *A61B 17/0642* (2013.01); *A61B 17/10* (2013.01); *A61F 2/0811* (2013.01); *A61B 2017/00964* (2013.01); *A61B 2017/0647* (2013.01); *A61F 2002/0068* (2013.01); *A61F 2002/0072* (2013.01); *A61F 2002/0817* (2013.01); *A61F 2002/0858* (2013.01); *A61F 2002/0882* (2013.01); *A61F 2220/0016* (2013.01); *A61F 2230/0006* (2013.01); *A61F 2230/0008* (2013.01)

(58) Field of Classification Search
USPC .......................................................... 606/151
See application file for complete search history.

(56) References Cited

U.S. PATENT DOCUMENTS

| | | |
|---|---|---|
| 511,238 A | 12/1893 | Hieatzman et al. |
| 765,793 A | 7/1904 | Ruckel |
| 1,728,316 A | 9/1929 | Von Wachenfeldt |
| 1,855,546 A | 4/1932 | File |
| | (Continued) | |

FOREIGN PATENT DOCUMENTS

| | | |
|---|---|---|
| CA | 2390508 A1 | 5/2001 |
| CA | 2945821 A1 | 11/2015 |
| | (Continued) | |

OTHER PUBLICATIONS

International Search Report and Written Opinion for Application No. PCT/US2016/069261, 24 pages, dated Mar. 29, 2017.
(Continued)

*Primary Examiner* — Yashita Sharma
(74) *Attorney, Agent, or Firm* — Seager, Tufte & Wickhem LLP.

(57) ABSTRACT

An example implant delivery system is disclosed. The example implant delivery system includes a delivery shaft including a proximal portion, a distal portion and a lumen extending therebetween. The delivery system also includes a frame detachably coupled to the distal portion of the delivery shaft and a tack member coupled to the frame.

39 Claims, 27 Drawing Sheets

(56) References Cited

U.S. PATENT DOCUMENTS

| | | |
|---|---|---|
| 1,868,100 A | 7/1932 | Goodstein |
| 1,910,688 A | 5/1933 | Goodstein |
| 1,940,351 A | 12/1933 | Howard |
| 2,034,785 A | 3/1936 | Wappler |
| 2,075,508 A | 3/1937 | Davidson |
| 2,131,321 A | 9/1938 | Hart |
| 2,154,688 A | 4/1939 | Matthews et al. |
| 2,158,242 A | 5/1939 | Maynard |
| 2,199,025 A | 4/1940 | Conn |
| 2,201,610 A | 5/1940 | Dawson, Jr. |
| 2,254,620 A | 9/1941 | Miller |
| 2,277,931 A | 3/1942 | Moe |
| 2,283,814 A | 5/1942 | La Place |
| 2,316,297 A | 4/1943 | Southerland et al. |
| 2,421,193 A | 5/1947 | Gardner |
| 2,571,813 A | 10/1951 | Austin |
| 2,630,316 A | 3/1953 | Foster |
| 2,684,070 A | 7/1954 | Kelsey |
| 2,744,251 A | 5/1956 | Vollmer |
| 2,790,341 A | 4/1957 | Keep et al. |
| 2,817,339 A | 12/1957 | Sullivan |
| 2,825,162 A | 3/1958 | Flood |
| 2,881,762 A | 4/1959 | Lowrie |
| 2,910,067 A | 10/1959 | White |
| 3,068,870 A | 12/1962 | Levin |
| 3,077,812 A | 2/1963 | Dietrich |
| 3,103,666 A | 9/1963 | Bone |
| 3,123,077 A | 3/1964 | Alcamo |
| 3,209,754 A | 10/1965 | Brown |
| 3,221,746 A | 12/1965 | Noble |
| 3,470,834 A | 10/1969 | Bone |
| 3,527,223 A | 9/1970 | Shein |
| 3,570,497 A | 3/1971 | Lemole |
| 3,577,837 A | 5/1971 | Bader, Jr. |
| 3,579,831 A | 5/1971 | Stevens et al. |
| 3,643,851 A | 2/1972 | Green et al. |
| 3,687,138 A | 8/1972 | Jarvik |
| 3,716,058 A | 2/1973 | Tanner, Jr. |
| 3,717,294 A | 2/1973 | Green |
| 3,757,629 A | 9/1973 | Schneider |
| 3,777,538 A | 12/1973 | Weatherly et al. |
| 3,837,555 A | 9/1974 | Green |
| 3,845,772 A | 11/1974 | Smith |
| 3,875,648 A | 4/1975 | Bone |
| 3,960,147 A | 6/1976 | Murray |
| 3,976,079 A | 8/1976 | Samuels et al. |
| 4,014,492 A | 3/1977 | Rothfuss |
| 4,127,227 A | 11/1978 | Green |
| 4,259,959 A | 4/1981 | Walker |
| 4,263,903 A | 4/1981 | Griggs |
| 4,265,226 A | 5/1981 | Cassimally |
| 4,317,451 A | 3/1982 | Cerwin et al. |
| 4,400,833 A | 8/1983 | Kurland |
| 4,422,567 A | 12/1983 | Haynes |
| 4,454,875 A | 6/1984 | Pratt et al. |
| 4,480,641 A | 11/1984 | Failla et al. |
| 4,485,816 A | 12/1984 | Krumme |
| 4,526,174 A | 7/1985 | Froehlich |
| 4,549,545 A | 10/1985 | Levy |
| 4,570,623 A | 2/1986 | Ellison et al. |
| 4,595,007 A | 6/1986 | Mericle |
| 4,624,254 A | 11/1986 | McGarry et al. |
| 4,627,437 A | 12/1986 | Bedi et al. |
| 4,632,100 A | 12/1986 | Somers et al. |
| 4,635,637 A | 1/1987 | Schreiber |
| 4,669,473 A | 6/1987 | Richards et al. |
| 4,696,300 A | 9/1987 | Anderson |
| 4,719,917 A | 1/1988 | Barrows et al. |
| 4,738,255 A | 4/1988 | Goble et al. |
| 4,741,330 A | 5/1988 | Hayhurst |
| 4,762,260 A | 8/1988 | Richards et al. |
| 4,799,495 A | 1/1989 | Hawkins et al. |
| 4,809,695 A | 3/1989 | Gwathmey et al. |
| 4,851,005 A | 7/1989 | Hunt et al. |
| 4,858,608 A | 8/1989 | McQuilkin |
| 4,884,572 A | 12/1989 | Bays et al. |
| 4,887,601 A | 12/1989 | Richards |
| 4,924,866 A | 5/1990 | Yoon |
| 4,930,674 A | 6/1990 | Barak |
| 4,968,315 A | 11/1990 | Gattuma |
| 4,976,715 A | 12/1990 | Bays et al. |
| 4,994,073 A | 2/1991 | Green |
| 4,997,436 A | 3/1991 | Oberlander |
| 5,002,563 A | 3/1991 | Pyka et al. |
| 5,013,316 A | 5/1991 | Goble et al. |
| 5,015,249 A | 5/1991 | Nakao et al. |
| 5,037,422 A | 8/1991 | Hayhurst et al. |
| 5,041,129 A | 8/1991 | Hayhurst et al. |
| 5,046,513 A | 9/1991 | Gattuma et al. |
| 5,053,047 A | 10/1991 | Yoon |
| 5,059,206 A | 10/1991 | Winters |
| 5,062,563 A | 11/1991 | Green et al. |
| 5,100,417 A | 3/1992 | Cerier et al. |
| 5,102,421 A | 4/1992 | Anspach, Jr. |
| 5,116,357 A | 5/1992 | Eberbach |
| 5,122,155 A | 6/1992 | Eberbach |
| 5,123,913 A | 6/1992 | Wilk et al. |
| RE34,021 E | 8/1992 | Mueller et al. |
| 5,141,515 A | 8/1992 | Eberbach |
| 5,141,520 A | 8/1992 | Goble et al. |
| 5,156,609 A | 10/1992 | Nakao et al. |
| 5,156,616 A | 10/1992 | Meadows et al. |
| 5,167,665 A | 12/1992 | McKinney |
| 5,171,259 A | 12/1992 | Inoue |
| 5,174,295 A | 12/1992 | Christian et al. |
| 5,174,487 A | 12/1992 | Rothfuss et al. |
| 5,176,682 A | 1/1993 | Chow |
| 5,176,692 A | 1/1993 | Wilk et al. |
| 5,203,787 A | 4/1993 | Noblitt et al. |
| 5,217,472 A | 6/1993 | Green et al. |
| 5,224,946 A | 7/1993 | Hayhurst et al. |
| 5,238,004 A | 8/1993 | Sahatjian et al. |
| 5,242,457 A | 9/1993 | Akopov et al. |
| 5,246,441 A | 9/1993 | Ross et al. |
| 5,251,642 A | 10/1993 | Handlos |
| 5,261,914 A | 11/1993 | Warren |
| 5,269,753 A | 12/1993 | Wilk |
| 5,269,783 A | 12/1993 | Sander |
| 5,282,829 A | 2/1994 | Hermes |
| 5,289,963 A | 3/1994 | McGarry et al. |
| 5,290,217 A | 3/1994 | Campos |
| 5,304,187 A | 4/1994 | Green et al. |
| 5,333,624 A | 8/1994 | Tovey |
| 5,342,396 A | 8/1994 | Cook |
| 5,350,400 A | 9/1994 | Esposito et al. |
| 5,352,229 A | 10/1994 | Goble et al. |
| 5,354,292 A | 10/1994 | Braeuer et al. |
| 5,364,408 A | 11/1994 | Gordon |
| 5,366,460 A | 11/1994 | Eberbach |
| 5,370,650 A | 12/1994 | Tovey et al. |
| 5,372,604 A | 12/1994 | Trott |
| 5,380,334 A | 1/1995 | Torrie et al. |
| 5,383,477 A | 1/1995 | DeMatteis |
| 5,397,332 A | 3/1995 | Kammerer et al. |
| 5,403,326 A | 4/1995 | Harrison et al. |
| 5,405,360 A | 4/1995 | Tovey |
| 5,411,522 A | 5/1995 | Trott |
| 5,411,523 A | 5/1995 | Goble |
| 5,417,691 A | 5/1995 | Hayhurst |
| 5,417,712 A | 5/1995 | Whittaker et al. |
| 5,425,490 A | 6/1995 | Goble et al. |
| 5,441,502 A | 8/1995 | Bartlett |
| 5,441,508 A | 8/1995 | Gazielly et al. |
| 5,456,720 A | 10/1995 | Schultz et al. |
| 5,464,403 A | 11/1995 | Kieturakis et al. |
| 5,478,354 A | 12/1995 | Tovey et al. |
| 5,482,864 A | 1/1996 | Knobel |
| 5,486,197 A | 1/1996 | Le et al. |
| 5,497,933 A | 3/1996 | DeFonzo et al. |
| 5,500,000 A | 3/1996 | Feagin et al. |
| 5,501,695 A | 3/1996 | Anspach, Jr. et al. |
| 5,503,623 A | 4/1996 | Tilton, Jr. |
| 5,505,735 A | 4/1996 | Li |
| 5,507,754 A | 4/1996 | Green et al. |

(56) References Cited

U.S. PATENT DOCUMENTS

| | | |
|---|---|---|
| 5,520,700 A | 5/1996 | Beyar et al. |
| 5,522,817 A | 6/1996 | Sander et al. |
| 5,545,180 A | 8/1996 | Le et al. |
| 5,560,532 A | 10/1996 | DeFonzo et al. |
| 5,562,689 A | 10/1996 | Green et al. |
| 5,569,306 A | 10/1996 | Thal |
| 5,582,616 A | 12/1996 | Bolduc et al. |
| 5,584,835 A | 12/1996 | Greenfield |
| 5,618,314 A | 4/1997 | Harwin et al. |
| 5,622,257 A | 4/1997 | Deschenes et al. |
| 5,628,751 A | 5/1997 | Sander et al. |
| 5,643,319 A | 7/1997 | Green et al. |
| 5,643,321 A | 7/1997 | McDevitt |
| 5,647,874 A | 7/1997 | Hayhurst |
| 5,649,963 A | 7/1997 | McDevitt |
| 5,662,683 A | 9/1997 | Kay |
| 5,667,513 A | 9/1997 | Torrie et al. |
| 5,674,245 A | 10/1997 | Ilgen |
| 5,681,342 A | 10/1997 | Benchetrit |
| 5,702,215 A | 12/1997 | Li |
| 5,713,903 A | 2/1998 | Sander et al. |
| 5,720,753 A | 2/1998 | Sander et al. |
| 5,725,541 A | 3/1998 | Anspach, III et al. |
| 5,741,282 A | 4/1998 | Anspach, III et al. |
| 5,766,246 A | 6/1998 | Mulhauser et al. |
| 5,782,864 A | 7/1998 | Lizardi |
| 5,797,909 A | 8/1998 | Michelson |
| 5,797,931 A | 8/1998 | Bito et al. |
| 5,797,963 A | 8/1998 | McDevitt |
| 5,807,403 A | 9/1998 | Beyar et al. |
| 5,830,221 A | 11/1998 | Stein et al. |
| 5,836,961 A | 11/1998 | Kieturakis et al. |
| 5,868,762 A | 2/1999 | Cragg et al. |
| 5,873,891 A | 2/1999 | Sohn |
| 5,885,258 A | 3/1999 | Sachdeva et al. |
| 5,885,294 A | 3/1999 | Pedlick et al. |
| 5,893,856 A | 4/1999 | Jacob et al. |
| 5,904,696 A | 5/1999 | Rosenman |
| 5,919,184 A | 7/1999 | Tilton, Jr. |
| 5,922,026 A | 7/1999 | Chin |
| 5,928,244 A | 7/1999 | Tovey et al. |
| 5,948,000 A | 9/1999 | Larsen et al. |
| 5,957,939 A | 9/1999 | Heaven et al. |
| 5,957,953 A | 9/1999 | Dipoto et al. |
| 5,968,044 A | 10/1999 | Nicholson et al. |
| 5,980,557 A | 11/1999 | Iserin et al. |
| 5,989,265 A | 11/1999 | Bouquet De La Joliniere et al. |
| 5,997,552 A | 12/1999 | Person et al. |
| 6,063,088 A | 5/2000 | Winslow |
| 6,099,518 A | 8/2000 | Adams et al. |
| 6,156,045 A | 12/2000 | Ulbrich et al. |
| 6,179,840 B1 | 1/2001 | Bowman |
| 6,193,731 B1 | 2/2001 | Oppelt et al. |
| 6,193,733 B1 | 2/2001 | Adams |
| 6,245,072 B1 | 6/2001 | Zdeblick et al. |
| 6,302,885 B1 | 10/2001 | Essiger |
| 6,312,442 B1 | 11/2001 | Kieturakis et al. |
| 6,315,789 B1 | 11/2001 | Cragg |
| 6,318,616 B1 | 11/2001 | Pasqualucci et al. |
| 6,322,563 B1 | 11/2001 | Cummings et al. |
| 6,325,805 B1 | 12/2001 | Ogilvie et al. |
| 6,387,113 B1 | 5/2002 | Hawkins et al. |
| 6,391,333 B1 | 5/2002 | Li et al. |
| 6,413,274 B1 | 7/2002 | Pedros |
| 6,425,900 B1 | 7/2002 | Knodel et al. |
| 6,436,110 B2 | 8/2002 | Bowman et al. |
| 6,447,522 B2 | 9/2002 | Gambale et al. |
| 6,447,524 B1 | 9/2002 | Knodel et al. |
| 6,478,803 B1 | 11/2002 | Kapec et al. |
| 6,482,178 B1 | 11/2002 | Andrews et al. |
| 6,482,210 B1 | 11/2002 | Skiba et al. |
| 6,506,190 B1 | 1/2003 | Walshe |
| 6,508,803 B1 | 1/2003 | Horikawa et al. |
| 6,511,499 B2 | 1/2003 | Schmieding et al. |
| 6,517,564 B1 | 2/2003 | Grafton et al. |
| 6,524,316 B1 | 2/2003 | Nicholson et al. |
| 6,527,795 B1 | 3/2003 | Lizardi |
| 6,530,933 B1 | 3/2003 | Yeung et al. |
| 6,540,769 B1 | 4/2003 | Miller, III |
| 6,551,333 B2 | 4/2003 | Kuhns et al. |
| 6,554,852 B1 | 4/2003 | Oberlander |
| 6,569,186 B1 | 5/2003 | Winters et al. |
| 6,575,976 B2 | 6/2003 | Grafton |
| 6,599,286 B2 | 7/2003 | Campin et al. |
| 6,620,185 B1 | 9/2003 | Harvie et al. |
| 6,629,988 B2 | 10/2003 | Weadock |
| 6,638,297 B1 | 10/2003 | Huitema |
| 6,639,365 B2 | 10/2003 | Pruett |
| 6,648,893 B2 | 11/2003 | Dudasik |
| 6,666,672 B1 | 12/2003 | Steffens |
| 6,666,872 B2 | 12/2003 | Barreiro et al. |
| 6,673,094 B1 | 1/2004 | McDevitt et al. |
| 6,685,728 B2 | 2/2004 | Sinnott et al. |
| 6,692,506 B1 | 2/2004 | Ory et al. |
| 6,723,099 B1 | 4/2004 | Goshert |
| 6,726,704 B1 | 4/2004 | Loshakove et al. |
| 6,726,705 B2 | 4/2004 | Peterson et al. |
| 6,740,100 B2 | 5/2004 | Demopulos et al. |
| 6,746,472 B2 | 6/2004 | Frazier et al. |
| 6,764,500 B1 | 7/2004 | Muijs Van De Moer et al. |
| 6,770,073 B2 | 8/2004 | McDevitt et al. |
| 6,779,701 B2 | 8/2004 | Bailly et al. |
| 6,800,081 B2 | 10/2004 | Parodi |
| 6,835,206 B2 | 12/2004 | Jackson |
| 6,849,078 B2 | 2/2005 | Durgin et al. |
| 6,887,259 B2 | 5/2005 | Lizardi |
| 6,926,723 B1 | 8/2005 | Mulhauser et al. |
| 6,932,834 B2 | 8/2005 | Lizardi et al. |
| 6,939,365 B1 | 9/2005 | Fogarty et al. |
| 6,946,003 B1 | 9/2005 | Wolowacz et al. |
| 6,949,117 B2 | 9/2005 | Gambale et al. |
| 6,964,685 B2 | 11/2005 | Murray et al. |
| 6,966,916 B2 | 11/2005 | Kumar |
| 6,972,027 B2 | 12/2005 | Fallin et al. |
| 6,984,241 B2 | 1/2006 | Lubbers et al. |
| 6,991,597 B2 | 1/2006 | Gellman et al. |
| 7,008,435 B2 | 3/2006 | Cummins |
| 7,021,316 B2 | 4/2006 | Leiboff |
| 7,025,772 B2 | 4/2006 | Gellman et al. |
| 7,033,379 B2 | 4/2006 | Peterson |
| 7,037,324 B2 | 5/2006 | Martinek |
| 7,048,171 B2 | 5/2006 | Thornton et al. |
| 7,063,711 B1 | 6/2006 | Loshakove et al. |
| 7,083,638 B2 | 8/2006 | Foerster |
| 7,087,064 B1 | 8/2006 | Hyde |
| 7,112,214 B2 | 9/2006 | Peterson et al. |
| 7,118,581 B2 | 10/2006 | Fridén |
| 7,144,403 B2 | 12/2006 | Booth |
| 7,144,413 B2 | 12/2006 | Wilford et al. |
| 7,144,414 B2 | 12/2006 | Harvie et al. |
| 7,150,750 B2 | 12/2006 | Damarati |
| 7,153,314 B2 | 12/2006 | Laufer et al. |
| 7,160,314 B2 | 1/2007 | Sgro et al. |
| 7,160,326 B2 | 1/2007 | Ball |
| 7,163,551 B2 | 1/2007 | Anthony et al. |
| 7,163,563 B2 | 1/2007 | Schwartz et al. |
| 7,169,157 B2 | 1/2007 | Kayan |
| 7,189,251 B2 | 3/2007 | Kay |
| 7,201,754 B2 | 4/2007 | Stewart et al. |
| 7,214,232 B2 | 5/2007 | Bowman et al. |
| 7,226,469 B2 | 6/2007 | Benavitz et al. |
| 7,229,452 B2 | 6/2007 | Kayan |
| 7,247,164 B1 | 7/2007 | Ritchart et al. |
| 7,303,577 B1 | 12/2007 | Dean |
| 7,309,337 B2 | 12/2007 | Colleran et al. |
| 7,320,692 B1 | 1/2008 | Bender et al. |
| 7,320,701 B2 | 1/2008 | Haut et al. |
| 7,322,935 B2 | 1/2008 | Palmer et al. |
| 7,326,231 B2 | 2/2008 | Phillips et al. |
| 7,343,920 B2 | 3/2008 | Toby et al. |
| 7,368,124 B2 | 5/2008 | Chun et al. |
| 7,377,934 B2 | 5/2008 | Lin et al. |
| 7,381,213 B2 | 6/2008 | Lizardi |
| 7,390,329 B2 | 6/2008 | Westra et al. |

(56) References Cited

U.S. PATENT DOCUMENTS

| | | |
|---|---|---|
| 7,399,304 B2 | 7/2008 | Gambale et al. |
| 7,404,824 B1 | 7/2008 | Webler et al. |
| 7,416,554 B2 | 8/2008 | Lam et al. |
| 7,452,368 B2 | 11/2008 | Liberatore et al. |
| 7,460,913 B2 | 12/2008 | Kuzma et al. |
| 7,463,933 B2 | 12/2008 | Wahlstrom et al. |
| 7,465,308 B2 | 12/2008 | Sikora et al. |
| 7,481,832 B1 | 1/2009 | Meridew et al. |
| 7,485,124 B2 | 2/2009 | Kuhns et al. |
| 7,497,854 B2 | 3/2009 | Gill et al. |
| 7,500,972 B2 | 3/2009 | Voegele et al. |
| 7,500,980 B2 | 3/2009 | Gill et al. |
| 7,500,983 B1 | 3/2009 | Kaiser et al. |
| 7,503,474 B2 | 3/2009 | Hillstead et al. |
| 7,506,791 B2 | 3/2009 | Omaits et al. |
| 7,559,941 B2 | 7/2009 | Zannis et al. |
| 7,572,276 B2 | 8/2009 | Lim et al. |
| 7,585,311 B2 | 9/2009 | Green et al. |
| 7,766,208 B2 | 8/2010 | Epperly et al. |
| 7,771,440 B2 | 8/2010 | Ortiz et al. |
| 7,776,057 B2 | 8/2010 | Laufer et al. |
| 7,780,685 B2 | 8/2010 | Hunt et al. |
| 7,785,255 B2 | 8/2010 | Malkani |
| 7,807,192 B2 | 10/2010 | Li et al. |
| 7,819,880 B2 | 10/2010 | Zannis et al. |
| 7,846,171 B2 | 12/2010 | Kullas et al. |
| 7,867,222 B1 | 1/2011 | Tilton, Jr. et al. |
| 7,918,879 B2 | 4/2011 | Yeung et al. |
| 8,114,101 B2 | 2/2012 | Criscuolo et al. |
| 8,197,837 B2 | 6/2012 | Jamiolkowski et al. |
| 8,585,773 B1 | 11/2013 | Kucklick |
| 8,668,718 B2 | 3/2014 | Euteneuer et al. |
| 8,763,878 B2 | 7/2014 | Euteneuer et al. |
| 8,821,536 B2 | 9/2014 | Euteneuer et al. |
| 8,821,537 B2 | 9/2014 | Euteneuer et al. |
| 8,840,642 B2 | 9/2014 | Euteneuer et al. |
| 8,864,780 B2 | 10/2014 | Euteneuer et al. |
| 8,920,464 B2 | 12/2014 | Euteneuer et al. |
| 9,005,224 B2 | 4/2015 | Euteneuer et al. |
| 9,027,819 B2 | 5/2015 | Euteneuer et al. |
| 9,033,201 B2 | 5/2015 | Euteneuer |
| 9,095,337 B2 | 8/2015 | Euteneuer et al. |
| 9,101,460 B2 | 8/2015 | Euteneuer et al. |
| 9,107,661 B2 | 8/2015 | Euteneuer et al. |
| 9,113,977 B2 | 8/2015 | Euteneuer et al. |
| 9,125,650 B2 | 9/2015 | Euteneuer et al. |
| 9,179,910 B2 | 11/2015 | Euteneuer et al. |
| 9,179,961 B2 | 11/2015 | Euteneuer et al. |
| 9,198,750 B2 | 12/2015 | Van Kampen et al. |
| 9,198,751 B2 | 12/2015 | Euteneuer et al. |
| 9,204,940 B2 | 12/2015 | Euteneuer et al. |
| 9,247,978 B2 | 2/2016 | Euteneuer et al. |
| 9,259,220 B2 | 2/2016 | Euteneuer et al. |
| 9,271,726 B2 | 3/2016 | Euteneuer |
| 9,314,314 B2 | 4/2016 | Euteneuer et al. |
| 9,314,331 B2 | 4/2016 | Euteneuer et al. |
| 9,370,356 B2 | 6/2016 | Euteneuer et al. |
| 9,393,103 B2 | 7/2016 | Van Kampen et al. |
| 9,393,104 B2 | 7/2016 | Kampen et al. |
| 9,414,841 B2 | 8/2016 | Euteneuer et al. |
| 9,566,063 B2 | 2/2017 | Euteneuer et al. |
| 9,878,141 B2 | 1/2018 | Kucklick |
| 2002/0077687 A1 | 6/2002 | Ahn |
| 2002/0090725 A1 | 7/2002 | Simpson et al. |
| 2002/0123767 A1 | 9/2002 | Prestel |
| 2002/0165559 A1 | 11/2002 | Grant et al. |
| 2003/0073979 A1 | 4/2003 | Naimark et al. |
| 2003/0125748 A1 | 7/2003 | Li et al. |
| 2003/0212456 A1 | 11/2003 | Lipchitz et al. |
| 2004/0059416 A1 | 3/2004 | Murray et al. |
| 2004/0073219 A1 | 4/2004 | Skiba et al. |
| 2004/0138705 A1 | 7/2004 | Heino et al. |
| 2004/0167519 A1 | 8/2004 | Weiner et al. |
| 2004/0220574 A1 | 11/2004 | Pelo et al. |
| 2005/0015021 A1 | 1/2005 | Shiber |
| 2005/0049618 A1 | 3/2005 | Masuda et al. |
| 2005/0051597 A1 | 3/2005 | Toledano |
| 2005/0059996 A1 | 3/2005 | Bauman et al. |
| 2005/0060033 A1 | 3/2005 | Vacanti et al. |
| 2005/0107807 A1 | 5/2005 | Nakao |
| 2005/0113736 A1 | 5/2005 | Orr et al. |
| 2005/0171569 A1 | 8/2005 | Girard et al. |
| 2005/0187576 A1 | 8/2005 | Whitman et al. |
| 2005/0240222 A1 | 10/2005 | Shipp |
| 2005/0274768 A1 | 12/2005 | Cummins et al. |
| 2006/0074423 A1 | 4/2006 | Alleyne et al. |
| 2006/0178743 A1 | 8/2006 | Carter |
| 2006/0235442 A1 | 10/2006 | Huitema |
| 2006/0293760 A1 | 12/2006 | DeDeyne |
| 2007/0078477 A1 | 4/2007 | Heneveld, Sr. et al. |
| 2007/0083236 A1 | 4/2007 | Sikora et al. |
| 2007/0112361 A1 | 5/2007 | Schonholz et al. |
| 2007/0179531 A1 | 8/2007 | Thornes |
| 2007/0185506 A1 | 8/2007 | Jackson |
| 2007/0190108 A1 | 8/2007 | Datta et al. |
| 2007/0219558 A1 | 9/2007 | Deutsch |
| 2007/0270804 A1 | 11/2007 | Chudik |
| 2007/0288023 A1 | 12/2007 | Pellegrino et al. |
| 2008/0027470 A1 | 1/2008 | Hart et al. |
| 2008/0051888 A1 | 2/2008 | Ratcliffe et al. |
| 2008/0065153 A1 | 3/2008 | Allard et al. |
| 2008/0090936 A1 | 4/2008 | Fujimura et al. |
| 2008/0125869 A1 | 5/2008 | Paz et al. |
| 2008/0135600 A1 | 6/2008 | Hiranuma et al. |
| 2008/0173691 A1 | 7/2008 | Mas et al. |
| 2008/0188874 A1 | 8/2008 | Henderson |
| 2008/0188936 A1 | 8/2008 | Ball et al. |
| 2008/0195119 A1 | 8/2008 | Ferree |
| 2008/0200949 A1 | 8/2008 | Hiles et al. |
| 2008/0241213 A1 | 10/2008 | Chun et al. |
| 2008/0272173 A1 | 11/2008 | Coleman et al. |
| 2008/0306408 A1 | 12/2008 | Lo |
| 2009/0001122 A1 | 1/2009 | Prommersberger et al. |
| 2009/0012521 A1 | 1/2009 | Axelson, Jr. et al. |
| 2009/0030434 A1 | 1/2009 | Paz et al. |
| 2009/0069806 A1 | 3/2009 | De La Mora Levy et al. |
| 2009/0076541 A1 | 3/2009 | Chin et al. |
| 2009/0105535 A1 | 4/2009 | Green et al. |
| 2009/0112085 A1 | 4/2009 | Eby |
| 2009/0134198 A1 | 5/2009 | Knodel et al. |
| 2009/0156986 A1 | 6/2009 | Trenhaile |
| 2009/0156997 A1 | 6/2009 | Trenhaile |
| 2009/0182245 A1 | 7/2009 | Zambelli |
| 2009/0242609 A1 | 10/2009 | Kanner |
| 2010/0145367 A1 | 6/2010 | Ratcliffe |
| 2010/0147922 A1 | 6/2010 | Olson |
| 2010/0163598 A1 | 7/2010 | Belzer |
| 2010/0191332 A1 | 7/2010 | Euteneuer et al. |
| 2010/0241227 A1 | 9/2010 | Euteneuer et al. |
| 2010/0249801 A1 | 9/2010 | Sengun et al. |
| 2010/0256675 A1 | 10/2010 | Romans |
| 2010/0274278 A1 | 10/2010 | Fleenor et al. |
| 2010/0292715 A1 | 11/2010 | Nering et al. |
| 2010/0292791 A1 | 11/2010 | Lu et al. |
| 2010/0312250 A1 | 12/2010 | Euteneuer et al. |
| 2010/0312275 A1 | 12/2010 | Euteneuer et al. |
| 2010/0327042 A1 | 12/2010 | Amid et al. |
| 2011/0000950 A1 | 1/2011 | Euteneuer et al. |
| 2011/0004221 A1 | 1/2011 | Euteneuer et al. |
| 2011/0011407 A1 | 1/2011 | Townsend et al. |
| 2011/0011917 A1 | 1/2011 | Loulmet |
| 2011/0034942 A1 | 2/2011 | Levin et al. |
| 2011/0040310 A1 | 2/2011 | Levin et al. |
| 2011/0040311 A1 | 2/2011 | Levin et al. |
| 2011/0066166 A1 | 3/2011 | Levin et al. |
| 2011/0106154 A1 | 5/2011 | DiMatteo et al. |
| 2011/0114700 A1 | 5/2011 | Baxter, III et al. |
| 2011/0224702 A1 | 9/2011 | Van Kampen et al. |
| 2011/0264149 A1 | 10/2011 | Pappalardo et al. |
| 2012/0100200 A1 | 4/2012 | Belcheva et al. |
| 2012/0160893 A1 | 6/2012 | Harris et al. |
| 2012/0193391 A1 | 8/2012 | Michler et al. |
| 2012/0209401 A1 | 8/2012 | Euteneuer et al. |
| 2012/0211543 A1 | 8/2012 | Euteneuer |

(56) References Cited

U.S. PATENT DOCUMENTS

| | | |
|---|---|---|
| 2012/0248171 A1 | 10/2012 | Bailly et al. |
| 2012/0316608 A1 | 12/2012 | Foley |
| 2013/0103100 A1 | 4/2013 | Ruffieux |
| 2013/0110156 A1 | 5/2013 | Nakayama et al. |
| 2013/0153627 A1 | 6/2013 | Euteneuer et al. |
| 2013/0153628 A1 | 6/2013 | Euteneuer |
| 2013/0158554 A1 | 6/2013 | Euteneuer et al. |
| 2013/0158587 A1 | 6/2013 | Euteneuer et al. |
| 2013/0158661 A1 | 6/2013 | Euteneuer et al. |
| 2013/0172920 A1 | 7/2013 | Euteneuer et al. |
| 2013/0172997 A1 | 7/2013 | Euteneuer et al. |
| 2013/0184716 A1 | 7/2013 | Euteneuer et al. |
| 2013/0240598 A1 | 9/2013 | Euteneuer et al. |
| 2013/0245627 A1 | 9/2013 | Euteneuer et al. |
| 2013/0245682 A1 | 9/2013 | Euteneuer et al. |
| 2013/0245683 A1 | 9/2013 | Euteneuer et al. |
| 2013/0245706 A1 | 9/2013 | Euteneuer et al. |
| 2013/0245707 A1 | 9/2013 | Euteneuer et al. |
| 2013/0245762 A1 | 9/2013 | Van Kampen et al. |
| 2013/0245774 A1 | 9/2013 | Euteneuer et al. |
| 2014/0188161 A1 | 7/2014 | Euteneuer et al. |
| 2014/0288593 A1 | 9/2014 | Euteneuer et al. |
| 2014/0371853 A1 | 12/2014 | Kampen et al. |
| 2015/0025630 A1 | 1/2015 | Euteneuer et al. |
| 2015/0112370 A1 | 4/2015 | Euteneuer et al. |
| 2015/0182326 A1 | 7/2015 | Euteneuer et al. |
| 2015/0230792 A1 | 8/2015 | Euteneuer et al. |
| 2015/0238190 A1 | 8/2015 | Euteneuer |
| 2015/0250477 A1 | 9/2015 | Euteneuer et al. |
| 2015/0272573 A1 | 10/2015 | Euteneuer et al. |
| 2015/0313705 A1 | 11/2015 | Euteneuer et al. |
| 2015/0320543 A1 | 11/2015 | Zenz-Olson |
| 2015/0327858 A1 | 11/2015 | Euteneuer et al. |
| 2015/0327975 A1 | 11/2015 | Euteneuer et al. |
| 2016/0030150 A1 | 2/2016 | Euteneuer et al. |
| 2016/0030157 A1 | 2/2016 | Euteneuer et al. |
| 2016/0051300 A1 | 2/2016 | Euteneuer et al. |
| 2016/0058535 A1 | 3/2016 | Euteneuer et al. |
| 2016/0100935 A1 | 4/2016 | Euteneuer et al. |
| 2016/0120538 A1 | 5/2016 | Westling et al. |
| 2016/0120542 A1 | 5/2016 | Westling et al. |
| 2016/0128693 A1 | 5/2016 | Euteneuer et al. |
| 2016/0135806 A1 | 5/2016 | Euteneuer |
| 2016/0256254 A1 | 9/2016 | Kucklick |
| 2016/0256258 A1 | 9/2016 | Euteneuer et al. |
| 2016/0262747 A1 | 9/2016 | Euteneuer et al. |
| 2016/0262780 A1 | 9/2016 | Kucklick |
| 2016/0296318 A1 | 10/2016 | Van Kampen et al. |
| 2016/0317147 A1 | 11/2016 | Euteneuer et al. |
| 2016/0317281 A1 | 11/2016 | Van Kampen et al. |
| 2016/0324616 A1 | 11/2016 | Zenz-Olson et al. |
| 2016/0361155 A1 | 12/2016 | Van Kampen |
| 2017/0181830 A1 | 6/2017 | Felix et al. |
| 2017/0181833 A1 | 6/2017 | Felix et al. |
| 2017/0189164 A1 | 7/2017 | Zenz-Olson et al. |

FOREIGN PATENT DOCUMENTS

| | | |
|---|---|---|
| EP | 0142225 A1 | 5/1985 |
| EP | 0298400 A1 | 1/1989 |
| EP | 0390613 A1 | 10/1990 |
| EP | 0543499 A1 | 5/1993 |
| EP | 0548998 A1 | 6/1993 |
| EP | 0557963 A1 | 9/1993 |
| EP | 0589306 A2 | 3/1994 |
| EP | 0908152 A1 | 4/1999 |
| EP | 1114618 A2 | 7/2001 |
| EP | 1491157 A1 | 12/2004 |
| EP | 1559379 A1 | 8/2005 |
| EP | 2030576 A2 | 3/2009 |
| EP | 2097021 A2 | 9/2009 |
| GB | 2154688 A | 9/1985 |
| GB | 2397240 A | 7/2004 |
| JP | 58188442 A | 11/1983 |
| JP | 2005586122 A | 3/2005 |
| JP | 2006515774 A | 6/2006 |
| WO | 8505025 A1 | 11/1985 |
| WO | 0176456 A2 | 10/2001 |
| WO | 0191644 A1 | 12/2001 |
| WO | 0234140 A2 | 5/2002 |
| WO | 2003105670 A2 | 12/2003 |
| WO | 2004000138 A1 | 12/2003 |
| WO | 2004093690 A1 | 11/2004 |
| WO | 2005016389 A2 | 2/2005 |
| WO | 2006086679 A1 | 8/2006 |
| WO | 2007014910 A1 | 2/2007 |
| WO | 2007030676 A2 | 3/2007 |
| WO | 2007078978 A2 | 7/2007 |
| WO | 2007082088 A2 | 7/2007 |
| WO | 2008111073 A2 | 9/2008 |
| WO | 2008111078 A2 | 9/2008 |
| WO | 2008139473 A2 | 11/2008 |
| WO | 2009079211 A1 | 6/2009 |
| WO | 2009143331 A1 | 11/2009 |
| WO | 2010141906 A1 | 12/2010 |
| WO | 2011095890 A2 | 8/2011 |
| WO | 2011128903 A2 | 10/2011 |
| WO | 2011140382 A1 | 11/2011 |
| WO | 20130101638 A1 | 7/2013 |
| WO | 2018144887 A1 | 8/2018 |

OTHER PUBLICATIONS

International Search Report and Written Opinion for Application No. PCT/US2018/064215, 17 pages, dated Feb. 22, 2019.

MEDICAL IMPLANT DELIVERY SYSTEM AND RELATED METHODS

CROSS REFERENCE TO RELATED APPLICATIONS

This application claims the benefit of U.S. Provisional Patent Application Ser. No. 62/595,737 filed on Dec. 7, 2017, the disclosure of which is incorporated herein by reference.

TECHNICAL FIELD

The present disclosure pertains generally, but not by way of limitation, to orthopedic implants and methods of treatment. More particularly, the present disclosure relates to a tendon repair implant, such as one that is engineered for arthroscopic placement over or in the area of a full or partial thickness tear of the supraspinatus tendon of the shoulder.

BACKGROUND

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. Adequate procedures do not exist for repairing a partial thickness tear of less than 50% in the supraspinatus tendon. Current procedures attempt to alleviate impingement or make room for movement of the tendon to prevent further damage and relieve discomfort but do not repair or strengthen the tendon. Use of the still damaged tendon can lead to further damage or injury. There is an ongoing need to deliver and adequately position medical implants during an arthroscopic procedure in order to treat injuries to the rotator cuff, rotator cuff tendons, or other soft tissue or tendon injuries throughout a body.

BRIEF SUMMARY

This disclosure provides design, material, manufacturing method, and use alternatives for medical devices. An example implant delivery system includes a delivery shaft including a proximal portion, a distal portion and a lumen extending therebetween. The delivery system also includes a frame detachably coupled to the distal portion of the delivery shaft and a tack member coupled to the frame.

Alternatively or additionally to any of the embodiments above, wherein further comprising a tether member coupled to a proximal portion of the tack member.

Alternatively or additionally to any of the embodiments above, wherein the tether member extends within the lumen of the delivery shaft.

Alternatively or additionally to any of the embodiments above, wherein the frame includes a body portion and a plurality of attachment arms extending away from the body portion.

Alternatively or additionally to any of the embodiments above, wherein the tack member extends through an aperture in the body portion of the frame.

Alternatively or additionally to any of the embodiments above, wherein a distal end portion of the tack member is configured to engage with a bone.

Alternatively or additionally to any of the embodiments above, wherein retraction of the tether member is designed to disengage the tack member from a bone.

Alternatively or additionally to any of the embodiments above, wherein the distal end portion of the tack member includes a tapered region.

Alternatively or additionally to any of the embodiments above, wherein a proximal end portion of the tack member includes a bore extending along a longitudinal axis of the tack member.

Alternatively or additionally to any of the embodiments above, wherein a distal end portion of the tether member is secured within the bore of the tack member.

Alternatively or additionally to any of the embodiments above, wherein the plurality of attachment arms are configured to be attached to an implant.

Alternatively or additionally to any of the embodiments above, wherein the frame is configured to detach from the delivery shaft in vivo.

Alternatively or additionally to any of the embodiments above, wherein the tether is directly coupled to the frame.

Alternatively or additionally to any of the embodiments above, wherein the tether is indirectly coupled to the frame via a connection member.

Alternatively or additionally to any of the embodiments above, wherein the frame further comprises a first aperture configured to couple with the connection member.

Alternatively or additionally to any of the embodiments above, wherein the connection member includes a first profile and wherein the lumen of the delivery sheath includes a second profile, and wherein the first profile is configured to mate with the second profile.

Alternatively or additionally to any of the embodiments above, wherein the connection member is configured to disengage from the delivery shaft, and wherein the connection member is configured to remain engaged to the frame after disengaging from the delivery shaft.

Alternatively or additionally to any of the embodiments above, wherein the tack member is stationary with respect to the connection member.

Alternatively or additionally to any of the embodiments above, wherein the tack member can translate with respect to the connection member.

Alternatively or additionally to any of the embodiments above, wherein the tack member includes a shaft having a circumferential surface and one or more protrusions extending radially away from the circumferential surface.

Alternatively or additionally to any of the embodiments above, wherein the one or more curved protrusions are configured to anchor the tack member beneath a layer of bone.

Alternatively or additionally to any of the embodiments above, wherein the one or more curved protrusions are spaced away from each other along the shaft.

Alternatively or additionally to any of the embodiments above, wherein the tack member includes a shaft formed from a first material and one or more fixation members disposed along the shaft, wherein the one or more fixation members are formed from a second material different from the first material.

Alternatively or additionally to any of the embodiments above, wherein the one or more fixation members extending radially away from a circumferential surface of the shaft.

Alternatively or additionally to any of the embodiments above, wherein the tether extends within the lumen of the delivery shaft while the delivery shaft is attached to the frame, and wherein the tether remains connected to the frame when the delivery shaft is detached from the frame.

An example method for delivering an implant to repair a tendon includes advancing an implant repair system to a target site. The implant repair system includes a delivery shaft including a proximal portion and a distal portion, and a frame detachably coupled to the distal portion of the delivery shaft via a connection member. The frame includes a body portion and a plurality of attachment arms extending away from the body portion. A tack member is coupled to the connection member. An implant is attached to the attachment arms. The method further includes positioning the implant adjacent a bony structure of the target site and engaging the tack member with the bony structure. Thereafter, the delivery shaft is detached from the frame in vivo with the tack member remaining engaged with the bony structure. Thereafter, the implant is affixed to the target site.

Alternatively or additionally to any of the embodiments above, wherein the connection member is coupled between a distal end of the delivery shaft and the frame, and wherein detaching the delivery shaft from the frame includes disengaging the connection member from the distal end of the delivery shaft.

Alternatively or additionally to any of the embodiments above, wherein engaging the tack member further includes anchoring the tack into the bony structure.

Alternatively or additionally to any of the embodiments above, wherein the tack member includes a shaft having a circumferential surface and one or more curved protrusions extending radially away from the circumferential surface, and wherein anchoring the tack into the bony structure includes positioning the one or more curved portions beneath a cortical layer of bone.

Alternatively or additionally to any of the embodiments above, wherein the tack member includes a shaft formed from a first material and one or more fixation members disposed along the shaft, wherein the one or more fixation members are formed from a second material different from the first material, and wherein anchoring the tack into the bony structure includes positioning the one or more fixation members adjacent a cortical layer of bone.

Alternatively or additionally to any of the embodiments above, wherein the method further comprises withdrawing the frame from the target site after affixing the implant to the target site, and wherein withdrawing the frame from the target site includes retracting a tether coupled to the frame.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
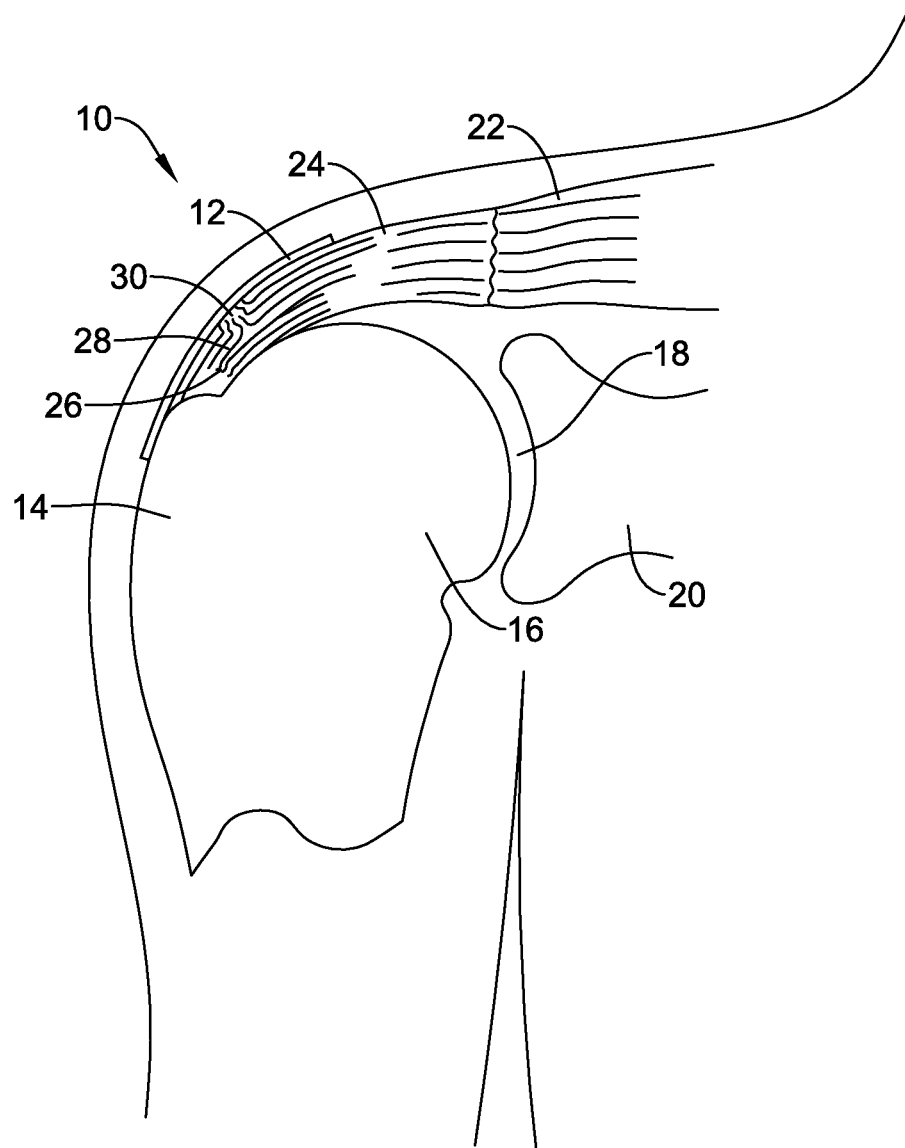
FIG. 1 illustrates a cross-section of an anterior view of a shoulder of a patient.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. Current repair procedures may attempt to alleviate impingement or make room for movement of the tendon to prevent further damage and relieve discomfort but do not repair or strengthen the tendon. An accepted treatment for rotator cuff tears may include reattaching the torn tendon to the humeral head using sutures. Additionally, in treating rotator cuff tears, an accepted practice may also include the placement of a scaffold over the repaired tendon to mechanically reinforce the repaired tendon. Therefore, there is an ongoing need to deliver and adequately position medical implants during an arthroscopic procedure in order to treat injuries to the rotator cuff, rotator cuff tendons, or other soft tissue or tendon injuries throughout a body.

FIG. 1 shows a cross-sectional view of a shoulder 10 including an example implant 12. Shoulder 10 further shows a head 14 of humerus 16 mating with a glenoid fossa 18 of scapula 20. The glenoid fossa 18 comprises a shallow depression in scapula 20. A supraspinatus tendon 22 is also shown. These muscles (along with others) control the movement of humerus 16 relative to scapula 20. A distal tendon 24 of supraspinatus tendon 22 meets humerus 16 at an insertion point 26.

In FIG. 1, tendon 24 includes a damaged portion 28 located near insertion point 26. Damaged portion 28 includes a tear 30 extending partially through tendon 24. Tear 30 may be referred to as a partial thickness tear. The depicted partial thickness tear 30 is on the bursal side of the tendon, however, the tear may also be on the opposite or articular side of the tendon 24 and/or may include internal tears to the tendon 24 not visible on either surface.

FIG. 1 further illustrates that the tendon repair implant 12 has been placed over the partial thickness tear 30. In this example, the tendon repair implant 12 is placed on the bursal side of the tendon regardless of whether the tear is on the bursal side, articular side or within the tendon. Further, the tendon repair implant 12 may overlay multiple tears.

In some instances, delivery of an implant 12 (e.g., a sheet-like implant) to a target site of a patient may require a physician to create an incision in the patient sufficient to access the target implant site. After creating this "access site," the physician may insert an implant delivery system through the access site and position the distal end of the implant delivery system adjacent the target implant site. The physician may then manipulate the implant delivery system to deploy an implant out of a delivery sheath adjacent the target implant site.

Figure 2:
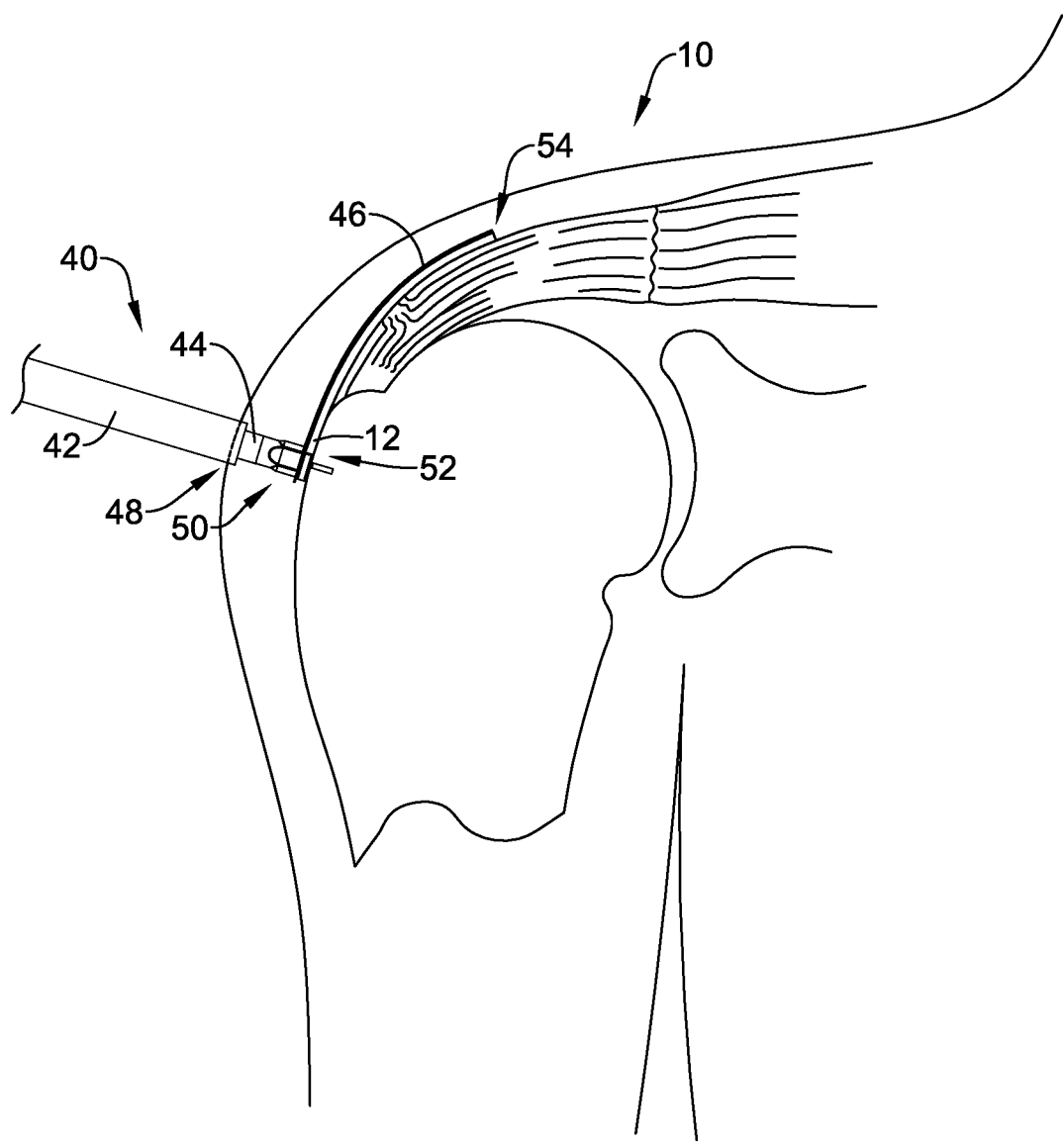
FIG. 2 illustrates a shoulder including a head of the humerus mating with the glenoid fossa of the scapula at a glenohumeral joint and an implant affixed to a tendon.

For example, FIG. 2 provides a perspective view of an implant delivery system 40 extending through the shoulder 10 of a patient. FIG. 2 shows implant delivery system 40 deployed adjacent a target site (e.g., a tear in the supraspinatus tendon). In at least some embodiments, implant delivery system 40 comprises a sheath member 42 (e.g., a cannula) including a proximal portion (not shown), a distal portion 48 and a lumen extending within at least a portion of cannula 42. Further, implant delivery system 40 may include a delivery shaft 44 extending within the lumen of sheath member 42 and longitudinally movable relative thereto.

Delivery shaft 44 may include a proximal portion (not shown) extending out of the proximal portion of sheath member 42 and/or otherwise manipulatable relative to sheath member 42 by a user. Additionally, in some examples the proximal portion of delivery shaft 44 and/or sheath member 44 may be coupled to a handle member (not shown). The handle member may be utilized to manipulate delivery shaft 44. For example, the handle member may be utilized to impart a rotational force to delivery shaft 44.

In addition, delivery shaft 44 may include a distal portion 50 extending out of the distal portion 48 of sheath member 42. Further, delivery shaft 44 may include a lumen extending therein. The lumen of delivery shaft 44 may extend along a portion or the entire length delivery shaft 44 (e.g., from distal portion 50 to the proximal portion of delivery shaft 44).

Delivery system 40 may further include a detachable frame member 46 attached to the distal portion 50 of the delivery shaft 44. As shown in FIG. 2, detachable frame 46 may be attached to an implant 12 (e.g., a sheet-like implant). For purposes of the discussion herein, the combined structure including frame 46 and implant 12 may be defined as having a proximal end 52 and a distal end 54 as illustrated in FIG. 2.

When initially positioning the frame 46 and implant 12 adjacent a target site, a clinician may orient the frame 46 and implant 12 (for example, via a handle member attached to a proximal portion of the delivery shaft 44) such that the proximal portion 52 may be adjacent (e.g., overlaid) on a portion of the humerus (e.g., on the bone), while the distal portion 54 of the frame 46 and implant 12 may overlay the tendon 24.

As described above, delivery of implant delivery system 40 may include the insertion of delivery sheath 42 through an access site (e.g., incision) and advancement to a target site. After positioning the distal end 48 of delivery sheath 42 proximate the target site, a clinician may deploy the detachable frame 46 in combination with the implant 12 out of the lumen located within and along the distal portion 48 of the delivery sheath 42, such as by retracting delivery sheath 42 relative to delivery shaft 44 and frame 46, and positioning implant 12 and frame 46 over the target site.

Prior to deployment, the detachable frame 46 and implant 12 combination may be contained (e.g., housed) within the lumen of delivery sheath 42 for subsequent deployment distally out distal opening of delivery sheath 42. As will be described in greater detail below, the combination of detachable frame 46 and implant 12 may wrap and/or fold upon itself such that it may be positioned within the lumen of the delivery sheath 42. Alternatively, detachable frame 46 and implant 12 may warp and/or fold around implant delivery shaft 44 while disposed within delivery sheath 42. The delivery sheath 42 constrains the frame 46 in a contracted configuration within the lumen of the delivery sheath 42.

Figure 3:
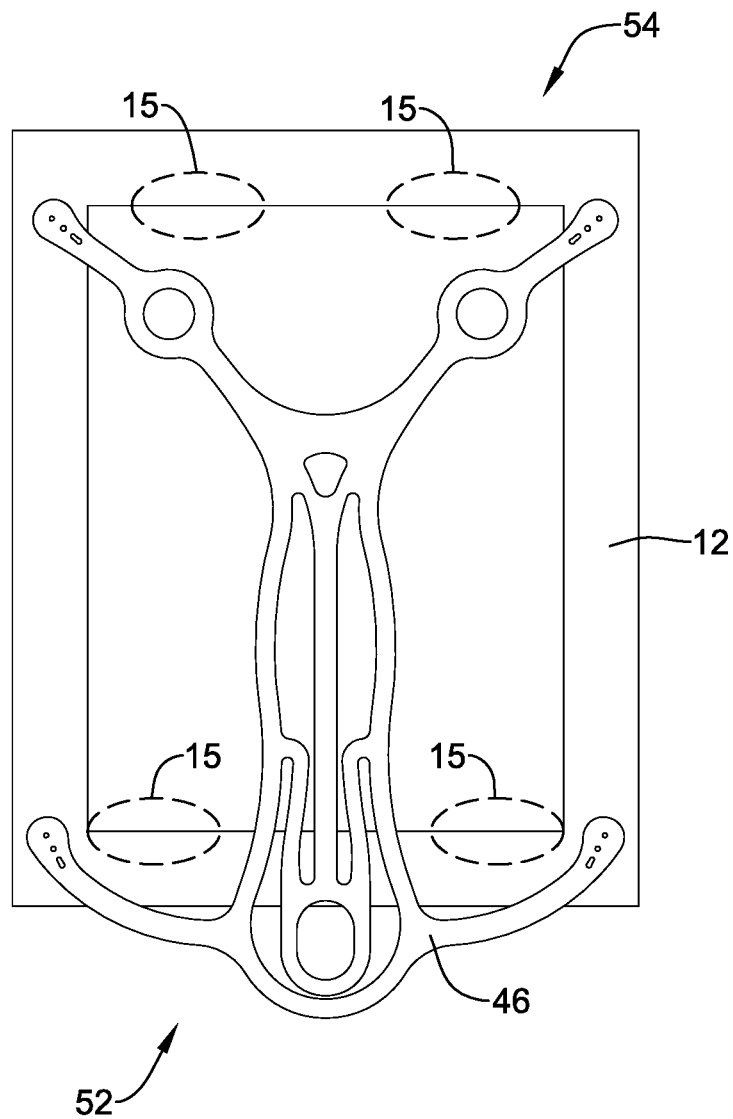
FIG. 3 illustrates an example implant delivery device attached to an implant.

FIG. 3 shows an example detachable frame member 46 attached to example implant 12. As stated above with reference to FIG. 2, detachable frame member 46 and implant 12 may have a proximal portion 52 which, for purposes of discussion herein, may be adjacent delivery shaft 44 and be configured to be positioned adjacent humerus 16. Further, detachable frame member 46 and implant 12 may have a distal portion 54 which, for purposes of discussion herein, may extend away from deliver shaft 44 and be configured to be positioned adjacent tendon 24.

FIG. 3 further shows fastening regions 15 located at various positions within implant 12. As shown in FIG. 3, the fastening regions 15 are positioned at locations which are free from the structure of frame member 46. In other words, the shape of frame 46 may be designed to specifically permit fastening implant 12 to the anatomy at locations 15. For example, a clinician may staple implant 12 to the anatomy at locations 15.

Figure 4A:
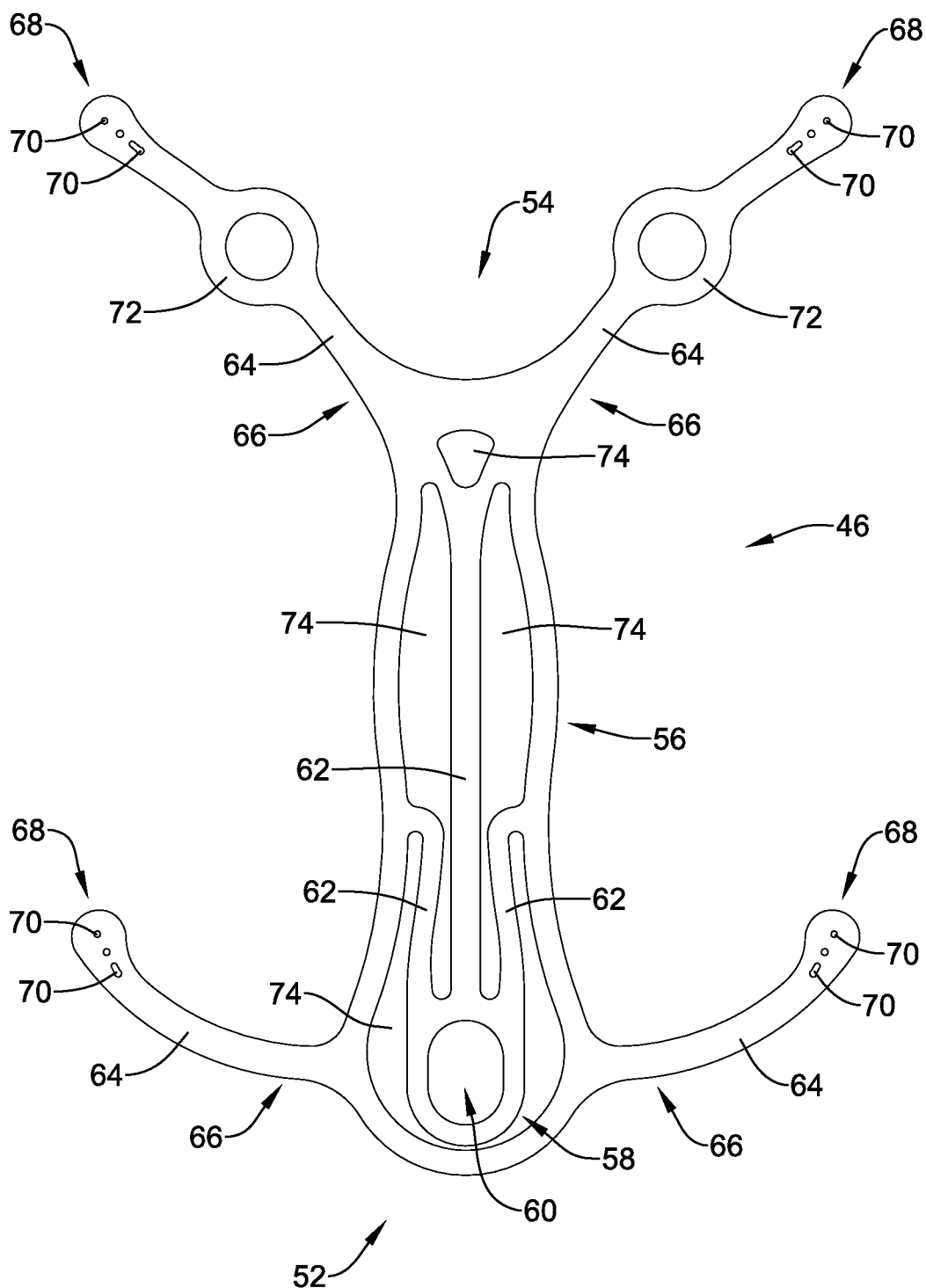
FIG. 4A illustrates another example implant delivery device.

FIG. 4A shows an example detachable frame member 46. As shown in FIG. 4A, frame member 46 may include a body portion 56. In some examples, body portion 56 may be understood to define a circular, ovular, or similar shaped framework from which other members may extend. For example, body portion 56 of frame 46 may bear some resemblance to an elongated oval having a proximal portion 52 and a distal portion 54. Body portion 56 may include one or more apertures 74. Further, frame 46 may include a head portion 58 positioned within and/or extending away from the proximal portion 52. Head portion 52 may include an aperture 60.

As shown in FIG. 4A, detachable frame 46 may include one or more attachment arms 64 extending away from body portion 56. Each respective attachment arm 64 may include a proximal portion 66 and a distal portion 68. The proximal portion 66 of each of the attachment arms 64 may be rigidly attached to body portion 56, while the distal portion 68 may be a free end of the attachment arm 64 spaced away from body portion 56. In some examples (such as that shown in FIG. 4A), attachment arms 64 and head portion 58 may form a monolithic structure with body portion 56. In other words, in some examples body portion 56, head portion 58 and attachment arms 64 may be formed (e.g., machined, cut, shaped, stamped, laser-cut, etc.) as a unitary structure from a single piece of material. However, the above discussion is not intended to be limiting. Rather, it is contemplated that detachable frame 46 may be constructed using alternative materials and/or manufacturing methodologies. For example, frame 46, or portions thereof, may be constructed from a polymeric material, a ceramic material and/or other various materials. Additionally, frame 46 may be manufactured via an injection molding or alternative polymer manufacturing methodologies. Alternatively, frame 46 may be formed through a 3-D printing process, if desired. Further, different portions of frame 46 (as described above, for example), may be made from a variety of materials and combined using alternative methodologies. For example, attachment arms 64 may be made from a polymer material and combined with a central frame member constructed from a metal. Variations of combining different materials with different portions of frame 46 are contemplated.

FIG. 4A further illustrates that attachment arms 64 may include a variety of shapes. For example, in some instances, attachment arms 64 may include a bow and/or general curvilinear shape (such as that shown in the attachment arm 64 closest to head portion 58). In other examples, an attachment arm 64 may include additional features, such as the circular portion 72 positioned along the attachment arm 64 (as shown in attachment arm 64 located farthest from head portion 58). In some instances, the circular portion 72 may be designed to provide a "visual engagement marker" for which a user (e.g., clinician) may be able to engage a secondary medical device and manipulate the position of the frame 46 after initial deployment. In other words, a clinician may be able to engage a secondary medical device with circular portion 72 and thereafter manipulate the secondary medical device to alter the initial deployment position of frame 46.

In some examples, frame 46 may include a variety of shapes and/or geometric arrangements. For example, while the above discussion has focused on the shape of frame 46 shown in FIG. 4A, it is not intended to be limiting. For example, frame 46 may include one or more stiffening members 62 extending throughout frame 46. Further, stiffening members 62 may be arranged within frame 46 (e.g., within body portion 56) such that they create one or more apertures 74. The number, shape, configuration and/or arrangement of stiffening members 62 and/or apertures 74 may depend on the particular performance characteristics desired to be imparted to detachable frame 46. For example, additional stiffening members 62 may be added to frame 46 to provide increased stiffness to frame 46. In other instances, stiffening members 62 may take on particular geometries that increase stiffness or flexibility in a particular direction while decreasing stiffness or flexibility in a different direction, for example.

Stiffening members 62 may be located (e.g., arranged) throughout frame 46 in a variety of configurations to provide additional stiffness and/or structural integrity to a particular frame shape. In other words, a wide variety of different shapes and/or arrangements of stiffening members 62 may be included within frame 46 in order to impart customized performance characteristics of frame 46. For example, in some instances, it may be desirable to transfer rotational forces placed on head portion 58 to attachment arms 64 positioned at the distal portion of frame 46. The addition of stiffening members 62 may allow transfer of those rotational forces throughout frame 46 (e.g., to the distal portion of frame 46) while minimizing the amount of force lost and/or dissipated throughout the frame due to undesirable flexing of the frame members.

Figure 4B:
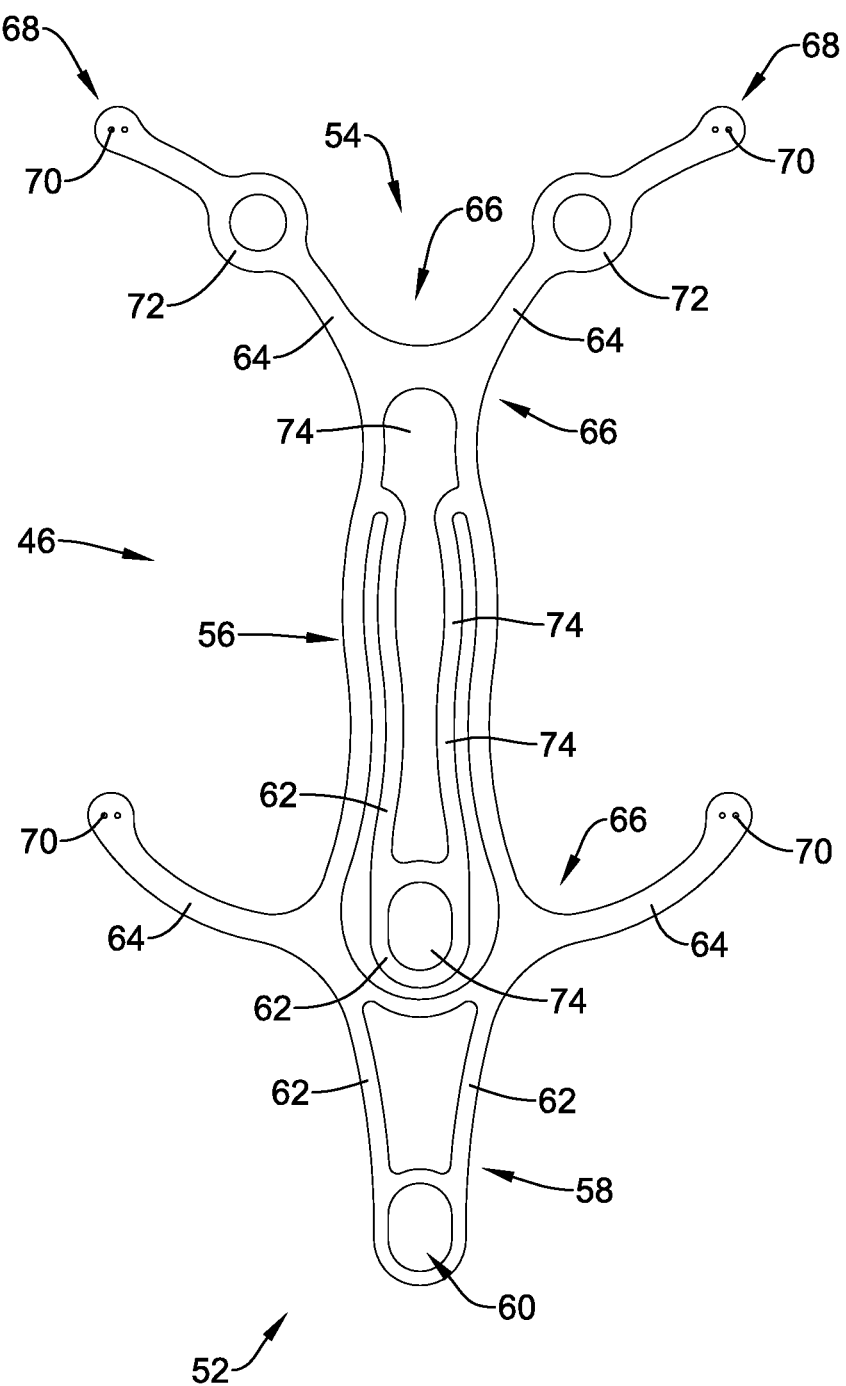
FIG. 4B illustrates another example implant delivery device.

FIG. 4B shows another example of the frame 46. For purposes of simplicity, the reference numerals depicted in FIG. 4B may represent analogous elements described in FIG. 4A. As shown in FIG. 4B, frame 46 may include a geometric shape that is similar to that described with respect to frame 46 shown in FIG. 4A. However, as illustrated in FIG. 4B, frame 46 may include stiffening members 62 extending and spaced in a different arrangement (as compared with the stiffening members 62 shown in FIG. 4A). Additionally, the frame 46 shown in FIG. 4B may include different apertures 74 created by the alternative arrangement of stiffening members 62.

FIGS. 4A and 4B further illustrate that frame 46 may include one or more attachment apertures 70 located along a distal portion 68 of one or more attachment arms 64. For example, FIGS. 4A/4B show attachment apertures 70 positioned at a distal portion 68 of the attachment arms 64. As will be discussed in greater detail below, attachment apertures 70 may be utilized to attach the frame 46 to an example implant 12.

While FIG. 4A shows three attachment apertures 70 positioned along a distal portion 68 of each of the attachment arms 64, the illustrated number of attachment apertures 70 is not intended to be limiting. In other embodiments, attachment apertures 70 may be located along another region of attachment arms 64, such as a proximal portion of attachment arms 64 proximate body portion 56. In other words, it is contemplated that one or more attachment arm apertures may be positioned along any portion of frame 46. For example, FIG. 4B shows two attachment apertures 70 positioned along a distal portion 68 of each of the attachment arms 64. The number of attachment apertures positioned along frame 46 may be 1, 2, 3, 4, 5, 6, 7, 8, 9, 10, 15, 20 or more. In other instances, attachment arms 64 may be devoid of attachment apertures. In such instances, attachment arms 64 may include an alternative attachment structure for attaching to implant 12.

For simplicity purposes, when combined with an example implant 12, frame 46 may be defined as having a first surface that faces away from the implant 12 when implant 12 is attached to frame 46 (e.g., a first surface that faces away from a target site in the body) and a second surface that faces the example implant 12 (e.g., a second surface that faces a target site in the body). In some instances, attachment apertures 70 may extend from the first surface to the second surface. In other words, in some instances, attachment apertures 70 may be defined as holes and/or openings that extend through the thickness of frame 46 from the first surface of the frame 46 that faces away from the implant 12 to the second surface of the frame 46 that faces toward the implant 12.

Figure 5A:
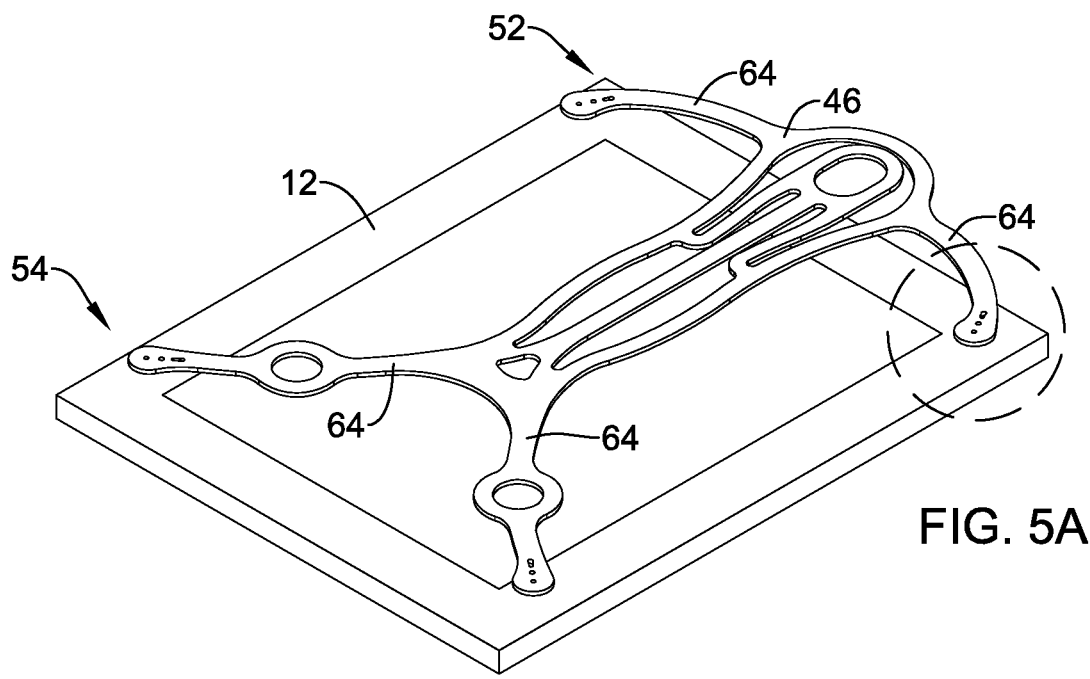
FIG. 5A illustrates another example implant delivery device attached to an implant.

As stated above, attachment apertures 70 may be utilized to attach and/or couple frame 46 to an example implant 12. FIG. 5A shows an example frame 46 attached to an example implant 12. Further, FIG. 5 shows example frame 46 attached to example implant 12 at the distal or free end of each of the four attachment arms 64, respectively. Attachment of free distal ends of attachment arms 64 to implant 12 may be made by any desired attachment mechanism.

Figure 5B:
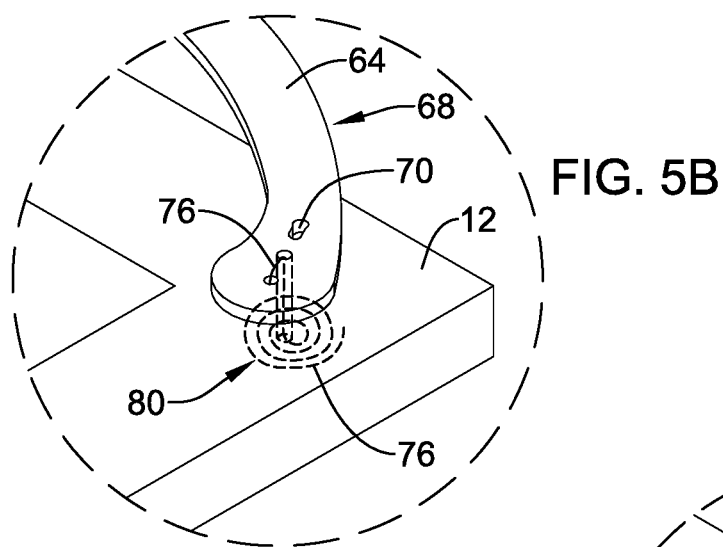
FIG. 5B illustrates an example delivery device attached to an implant.

FIG. 5B shows a detailed view of a portion of the proximal portion 54 of a frame 46 attached to an implant 12 in a configuration similar to that discussed above with respect to FIGS. 2-4. Further, FIG. 5B shows example attachment arm 64 including a distal portion 68. Three attachment apertures 70 are positioned along the distal portion 68 of the attachment arm 64. Additionally, FIG. 5B shows an example attachment member (e.g. wire) 76 extending between and through one or more of the attachment apertures 70 located on the distal portion 68 of attachment arms 64.

Attachment members 76 may be one of several structures and/or techniques contemplated to attach example frame 46 to example implant 12. As shown in FIG. 5B, attachment member 76 may be positioned, looped, wound and/or threaded through one or more attachment apertures 70 such that the member 76 is prevented from being pulled away from the distal portion 68 of attachment arm 64. In other words, winding attachment member 76 through one or more attachment apertures 70 may effectively affix attachment member 76 onto the attachment arm 64. In other words, it is contemplated that attachment member 76 may be affixed to the distal portion 68 of attachment arms 64 (via attachment apertures 70, for example) without having either end of the attachment member 76 directly attached (e.g., welded, tied, etc.) to any structure (e.g., frame 46). In some instances, member 76 may be wrapped and/or looped through attachment apertures 70 one or more times to provide a friction fit and/or resistive tension to unraveling or unwinding as a withdrawal force is applied to attachment member 76.

While FIG. 5B shows a single attachment member 76 extending between two attachment apertures 70, it is contemplated that attachment member 76 may extend and/or wrap between two or more attachment apertures 70. For example, it is contemplated that attachment member 76 may be woven (e.g., over-and-under) through three apertures 70 in order to lock member 76 to the distal end 68 of attachment arm 64.

The above discussion and the forgoing examples are not intended to limit the disclosure to using an attachment member (e.g., wire, thread, cable, etc.) to attach frame 46 to implant 12. Rather, a variety of methodologies may be utilized to attach frame 46 to implant 12. For example, adhesives may be used alone or in combination with another attachment mechanism to attach frame 46 to implant 12. Additionally, a variety of injection molding techniques may be employed to attach frame 46 to implant 12. Further, combinations of the disclosed techniques may be used to attach frame 46 to implant 12. For example, an attachment member 76 may be used in conjunction with an adhesive to attach frame 46 to implant 12 without having to wind attachment member 76 through attachment apertures 70.

As stated above, it is contemplated in the examples discussed herein that frame 46 may be able to be "detached" from implant 12. For example, frame 46 may be configured to detach from implant 12 after implant 12 has been affixed to a target site in the body, such as with staples and/or sutures. Therefore, it can be appreciated that in some examples disclosed herein, frame member 46 may be temporarily attached to implant 12. For example, frame member 46 may be coupled, affixed or attached to implant 12 while positioned within delivery sheath 42, deployed out of delivery sheath 42 and maneuvered into position relative to a target site. Once positioned at the target site (e.g., along the tendon and/or humeral head), implant 12 may be rigidly affixed to the target site, such as stapled and/or sutured to bone and/or tendon tissue at the target site. However, once implant 12 has been rigidly affixed to the target site, frame 46 may be pulled away (e.g., detached) from implant 12 and removed from the body.

FIG. 5B shows an example attachment configuration which may allow frame 46 to detach from implant 12. FIG. 5B shows attachment member 76 wound in a spiral pattern 80 along the surface of implant 12 facing a target site. In other words, attachment member 76 may form a spiral pattern 80 that remains in a plane substantially parallel to the plane of the surface of implant 12 which faces a target site. Further, it can be appreciated that attachment member 76 may extend from the side of attachment arm 64 facing away from implant 12, through the combined thickness of the attachment arm 64 and implant 12, eventually exiting implant 12 on the surface of implant 12 facing a target site. Further, it can be appreciated that the spiral pattern 80 shown in FIG. 5B is one of a variety of configurations for which attachment member 76 may be wound in order to prevent frame 46 from prematurely releasing from implant 12.

Attachment member 76 may have a first end secured to a free distal end of attachment arm 64 positioned on a first side of implant 12 and have a second end positioned on a second, opposite side of implant 12. In some instances, attachment member 76 may extend through implant 12 from the first side of implant 12 to the second side of implant 12. However, in other instances, attachment member 76 may extend around an edge of implant 12 from the first side of implant 12 to the second side of implant 12.

The attachment member 76 may be configured to be detached from implant 12 upon application of a threshold level of force. For example, the spiral pattern 80 shown in FIG. 5B may provide frame 46 the ability to detach from implant 12 when a force greater than or equal to a threshold "pull-away force" is applied to frame 46. For example, after implant 12 is affixed to a target site, a clinician may apply a force to frame 46 (via a tether, for example) such that frame 46 is pulled away from implant 12. Provided the force is great enough (e.g., the threshold force is met), attachment members 76 (e.g., spiral portion 80 of attachment member 76 shown in FIG. 5B) may be unwound and pulled back through the "body" (e.g., thickness) of implant 12, thereby releasing frame 46 from implant 12. In other words, provided a threshold pull-away force is applied to frame 46, the attachment member 76 forming the spiral 80 shown in FIG. 5B may unwind and pull back through implant 12. In some examples, the threshold "pull-away" force for the frame 46 to release from implant 12 may be about 0.25 lb to 1.75 lb, or may be about 0.75 lb to about 1.25 lb, or may be about 1.0 lb. Accordingly, the threshold "pull-away" force to release each of the four attachment member 76 from implant 12 may be about 0.0625 lb to 0.4375 lb, or may be about 0.1875 lb to about 0.3125 lb, or may be about 0.25 lb.

Figure 5C:
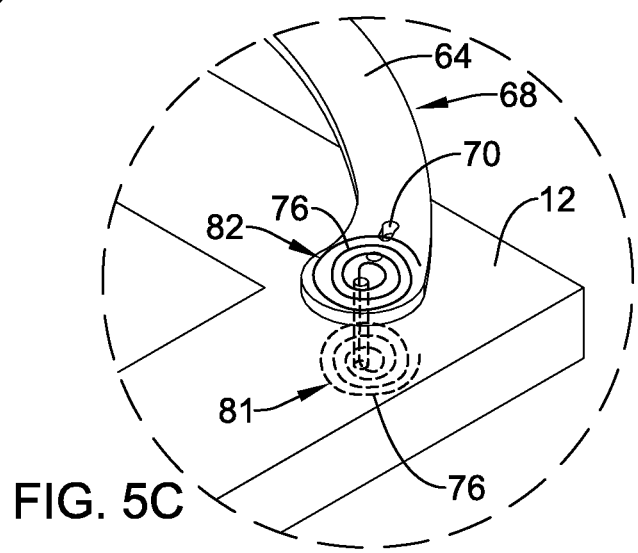
FIG. 5C illustrates an example delivery device attached to an implant.

FIG. 5C shows another example method to attach frame 46 to an example implant 12. As shown in FIG. 5C, attachment member 76 may include a spiral 81 positioned on the surface of the implant 12 which faces away from a target site (similar to spiral 80 shown in FIG. 5B). Additionally, FIG. 5C shows that attachment member 76 may include a second spiral 82 positioned on the surface of attachment arm 68 that faces away from implant 12. In other words, FIG. 5C shows two spirals 81/82 formed at opposite ends of attachment member 76 and positioned on both the attachment arm 64 facing away from implant 12 (e.g., spiral 82 of FIG. 5C) and on the side of the implant 12 lying along a treatment site (e.g., spiral 81 of FIG. 5C). The configuration of spirals 81/82 may provide a frame 46 with a "releasable" connection to implant 12 similar to that discussed with respect to FIG. 5B.

Figure 6:
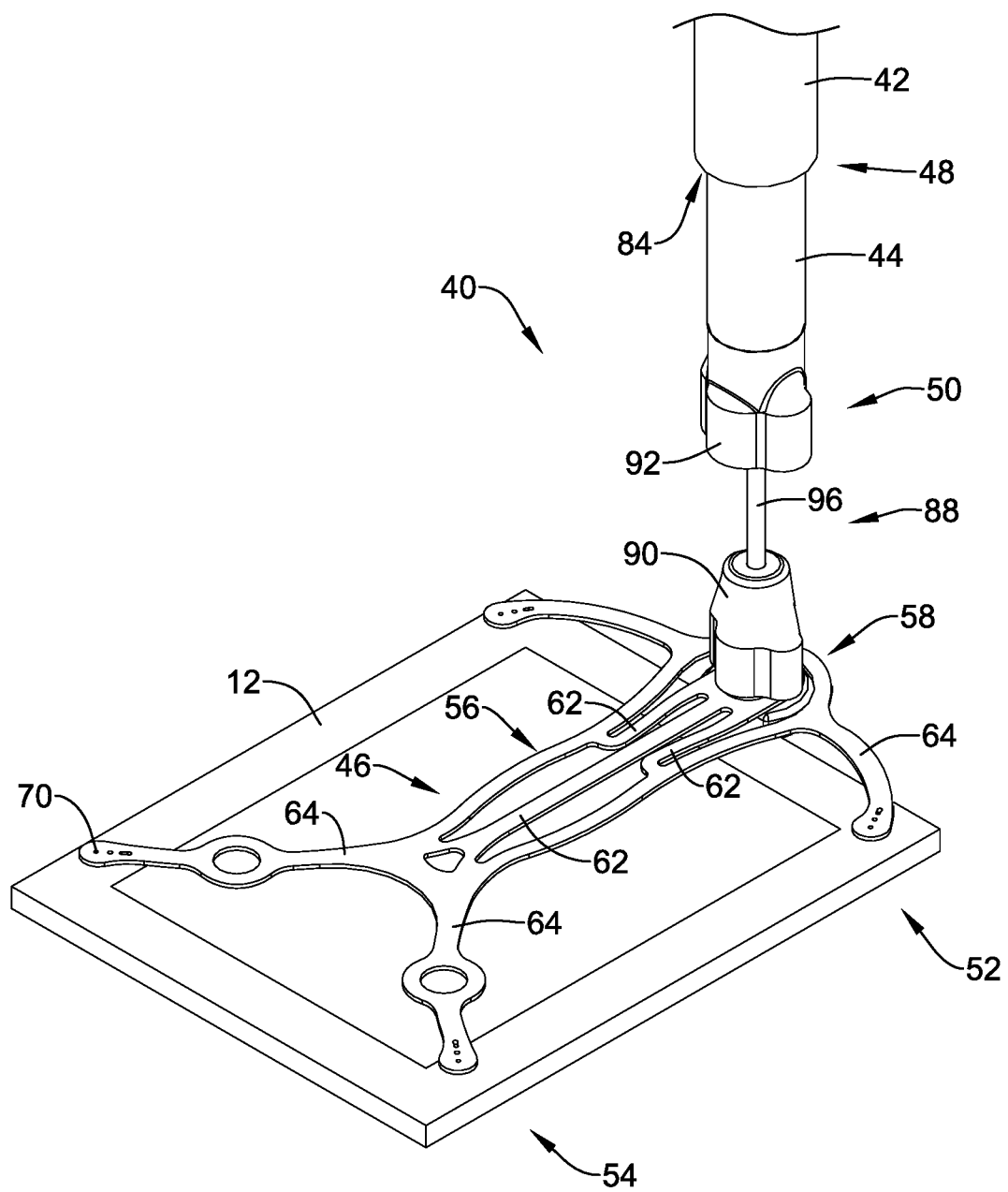
FIG. 6 illustrates another example implant delivery device.

FIG. 6 shows example frame 46 coupled to example implant 12 via attachment members 76 as described above. Further, FIG. 6 shows frame 46 in combination with implant 12 coupled to example implant delivery system 40. Similar to that discussed with respect to FIG. 2, implant delivery system 40 includes implant delivery shaft 44 extending through an example lumen 84 of an example delivery sheath 42.

Further, FIG. 6 shows the delivery shaft 44 coupled to frame 46 via a connection assembly 88. Connection assembly 88 may include a first connection member 90 attached to the head portion 58 of frame 46 and a second connection member 92 attached to the distal end 50 of delivery shaft 44. While FIG. 6 does not directly show first connection member 90 attached directly to second connection member 92, it can be appreciated that the first and second connection members 90/92 of connection assembly 88 may form a mating connection. For example, in some instances, first connection member 90 may form a male connection member while second connection member 92 may form a mating female connection member. In other words, in some examples second connection member 92 may include a cavity which is configured to extend over and allow first connection member 90 to be inserted therein. In other instances, the first connection member 90 may be a female connection member, while second connection member 92 may be a mating male connection member.

Additionally, as shown in FIG. 6, it is contemplated that second connection member 92 may disengage or decouple from first connection member 90. For example, in some instances connection assembly 88 (including first and second connection members 90/92) may be defined as a "quick release" connection assembly, or otherwise decoupling connection assembly. It is further contemplated that a variety of design configurations may be employed to engage/disengage (i.e., couple/decouple) the first and second connection members 90/92 from one another. For example, first and second connection members 90/92 may be coupled via a threaded connection, friction fit, spring loaded connection, bayonet connection, movable collar or other actuation mechanism, or the like. Further, connection member 90/92 may be engaged/disengaged by an operator of the device.

In some instances, delivery shaft 44 may be attached (via connection assembly 88, for example) to the head portion 58 of frame member 46. As shown in FIG. 6, the first connection member 90 of connection assembly 88 may attach to head portion 58 via an aperture 60 (shown in FIG. 3). In some instances, first connection member 90 may be attached to the head portion 58 of frame member 46 via a variety of mechanical fastening means (e.g., injection molding, encapsulation, bonding, etc.).

Figure 16:
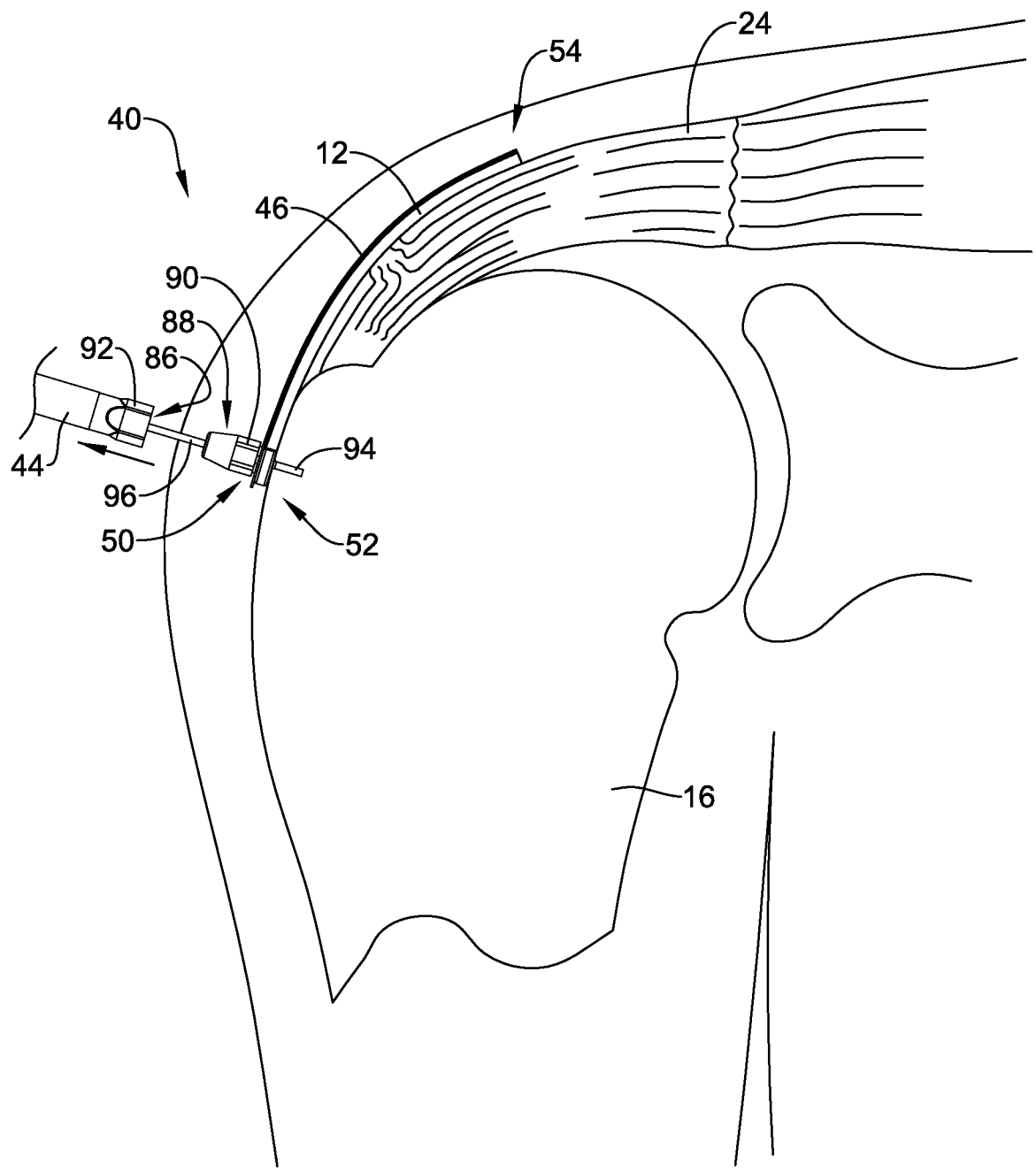

Additionally, in some instances, delivery system 40 may include a tether 96 coupled to frame 46. For example, FIG. 6, as well as FIG. 16, shows tether 96 attached to first connection member 90. However, it is contemplated that in some examples tether 96 may be coupled directly or indirectly to frame 46 and/or any other suitable structure. Further, tether 96 may be a rigid structure (e.g., rod) or it may be a non-rigid structure (e.g., a wire, cable, etc.). Additionally, it can be appreciated that tether 96 may be long enough to extend from frame 46 positioned at the target site to a location exterior of the patient through insertion site (i.e., incision), such as through a lumen 86 of delivery shaft 44 and out of a proximal portion of the implant delivery system 40 (e.g., proximal portion of delivery shaft 44). However, it is also contemplated that in some examples tether 96 may extend from frame 46 outside of delivery shaft 44 and out of a proximal portion of the implant delivery system 40. As will be discussed in greater detail below, the tether 96 may be utilized to withdraw the frame 46 out of the body after the implant 12 has been attached.

As discussed above, in some instances, a physician may insert implant delivery system 40 (including a delivery sheath 42, delivery shaft 44, frame 46 and implant 12) through an incision and position the distal end of the implant delivery system 40 adjacent a target implant site (e.g., torn tendon). Once adjacent the target site, the physician may manipulate the implant delivery shaft 44 to advance the implant (while attached to the detachable frame 46) out of the delivery sheath 42 adjacent the target implant site. For example, the physician may retract delivery sheath 42 proximally relative to delivery shaft 44 and frame 46 and/or may advance delivery shaft 44 and frame 46 distally relative to delivery sheath 42.

FIG. 6 shows frame 46 and implant 12 deployed from the distal portion 48 of delivery sheath 42. In some instances, frame 46 and implant 12 may have a substantially concave shape with respect to delivery sheath 42. It can be appreciated that the concave shape of frame member 46 and implant 12 may facilitate positioning the implant 12 along the generally rounded shape of the human shoulder.

However, when positioned in the delivery sheath 42 (e.g., prior to deployment) the frame 46 and implant 12 may be wrapped around the delivery shaft 44 in a convex configuration. Therefore, frame 46 and implant 12 may shift from a first convex configuration (while wrapped tightly around delivery shaft 44 within lumen 84 of delivery sheath 42) to a second concave configuration when advanced (e.g., deployed) out of sheath 42.

In other words, frame 46 and implant 12 may be attached to the delivery shaft 44 via the connection assembly 88 when positioned within the lumen 84 of the delivery sheath 42. In one example, when positioned within the delivery sheath 42, the frame 46 and implant 12 may wrap, or extend around, the delivery shaft 44. The position of the frame 46 and implant 12 may be in a convex configuration with respect to the distal end 50 of the delivery shaft 44. As the frame 46 and implant 12 are deployed out of the distal end 50 of the delivery shaft 44, the frame 46 and implant 12 may "shift" from a convex configuration to a concave configuration (as viewed with respect to the distal end 50 of delivery shaft 44).

Figure 7:
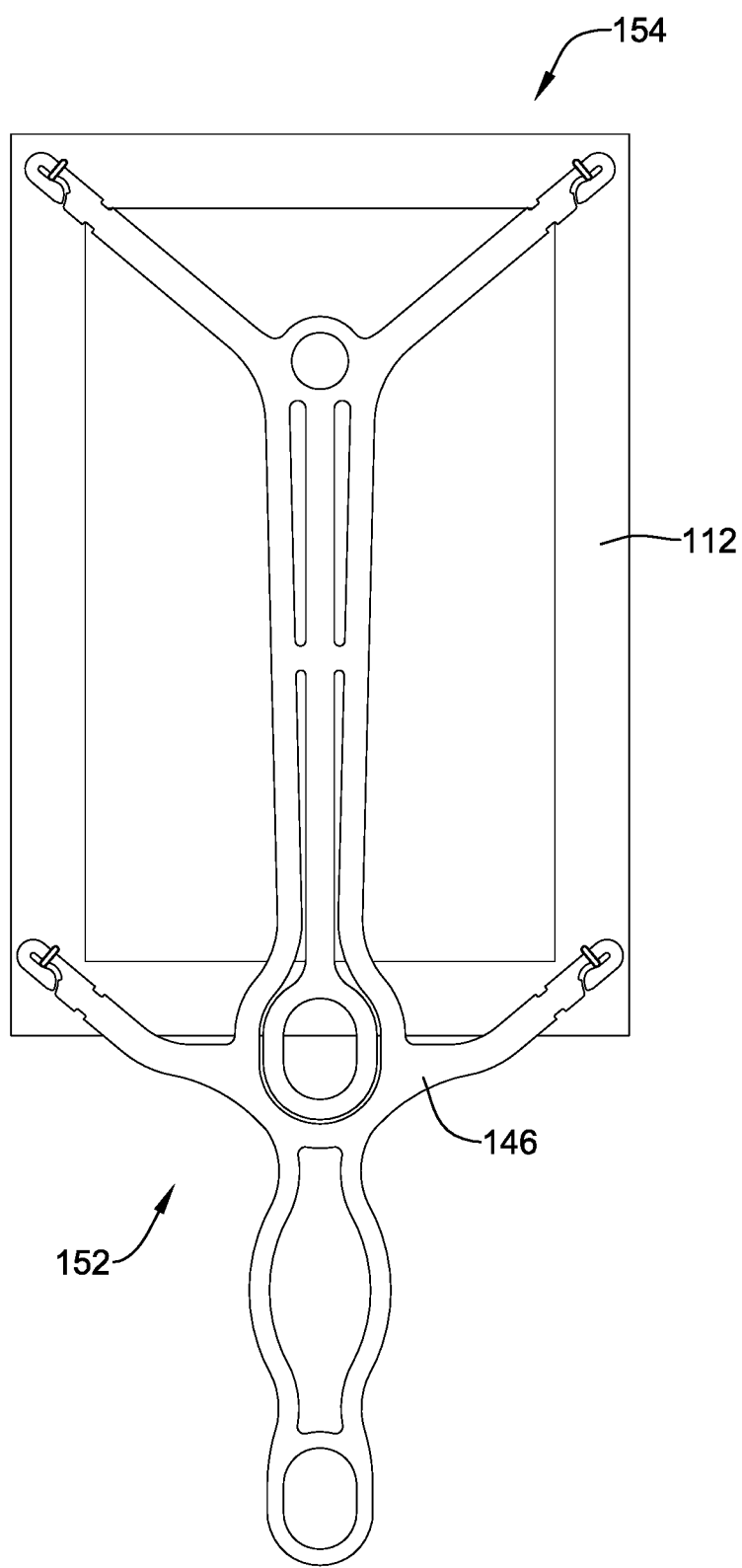
FIG. 7 illustrates an example implant delivery device attached to an implant.

FIG. 7 illustrates another example detachable frame member 146 attached to an implant 112. It is contemplated that any of the frame members and/or implants disclosed herein may be utilized in conjunction with any of the delivery systems and/or delivery system features disclosed herein. Further, frame member 146 and/or implant 112 may be similar in form and functionality to other example frame members described herein. For example, detachable frame member 146 and implant 112 may have a proximal portion 152 which, for purposes of discussion herein, may be adjacent delivery shaft 44 (described above) and be configured to be positioned adjacent humerus 16 (shown in FIG. 1). Further, detachable frame member 146 and implant 112 may have a distal portion 154 which, for purposes of discussion herein, may extend away from deliver shaft 44 (described above) and be configured to be positioned adjacent tendon 24 (shown in FIG. 1).

Figure 8:
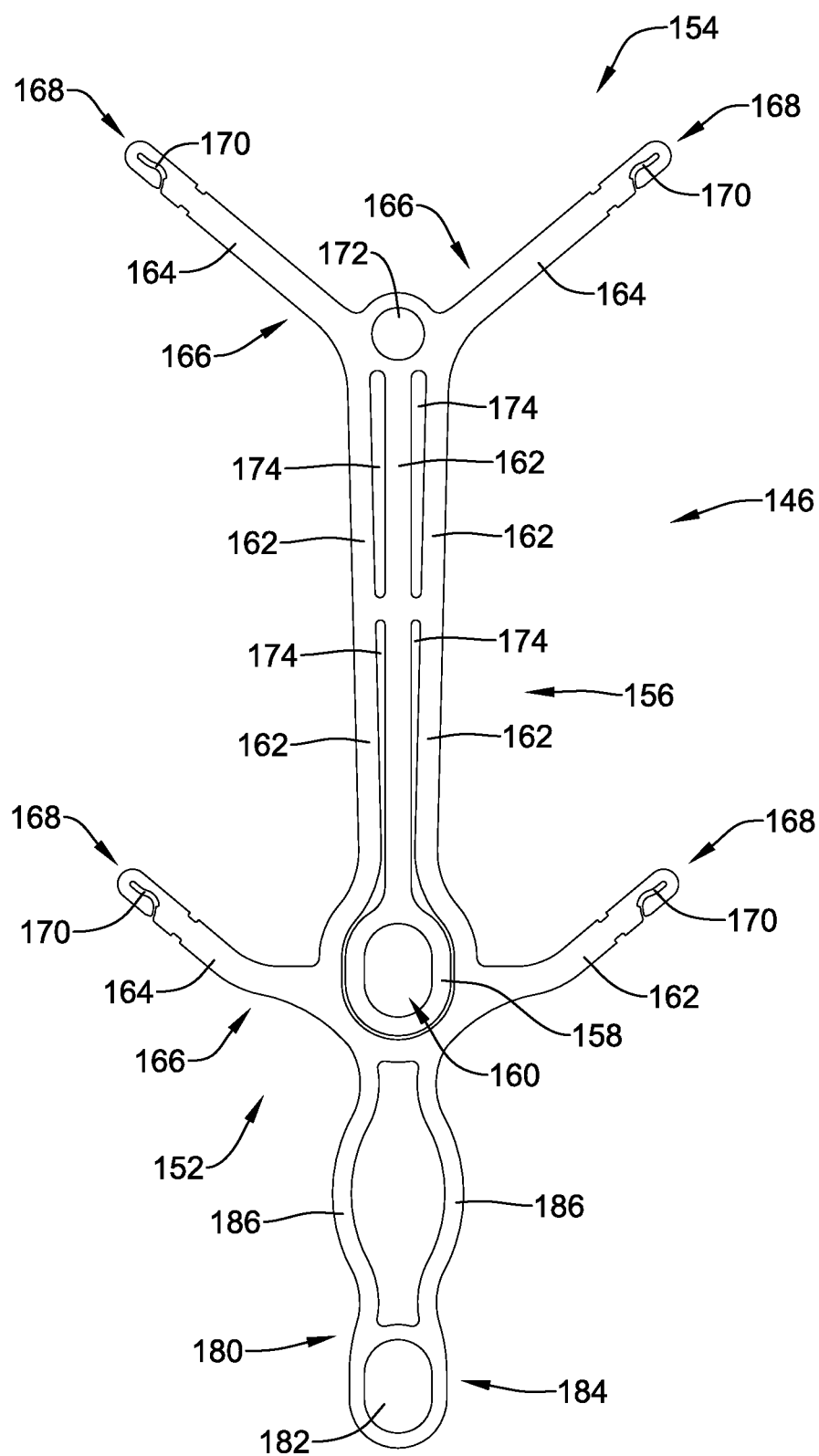
FIG. 8 illustrates another example implant delivery device.

FIG. 8 shows example detachable frame member 146. As illustrated in FIG. 8, frame member 146 may include a central body portion 156. In some examples, body portion 156 may be understood to define a circular, ovular, square, rectangular or similar shaped framework from which other members may extend. For example, body portion 156 of frame 146 may bear some resemblance to an elongated rectangle having a proximal portion 152 and a distal portion 154. Body portion 156 may include one or more apertures 174. Further, frame 146 may include a head portion 158 positioned within and/or extending away from the body portion 156. Head portion 158 may include an aperture 160.

As shown in FIG. 8, detachable frame 146 may include one or more attachment arms 164 extending away from body portion 156. Each respective attachment arm 164 may include a proximal portion 166 and a distal portion 168. The proximal portion 166 of each of the attachment arms 164 may be rigidly attached to body portion 156, while the distal portion 168 may be a free end of the attachment arm 164 spaced away from body portion 156. In some examples (such as that shown in FIG. 8), attachment arms 164 and head portion 158 may form a monolithic structure with body portion 156. In other words, in some examples body portion 156, head portion 158 and attachment arms 164 may be formed (e.g., machined, cut, shaped, stamped, laser-cut, etc.) as a unitary structure from a single piece of material. However, the above discussion is not intended to be limiting. Rather, it is contemplated that detachable frame 146 may be constructed using alternative materials and/or manufacturing methodologies. For example, frame 146, or portions thereof, may be constructed from a polymeric material, a ceramic material and/or other various materials. Additionally, frame 146 may be manufactured via an injection molding or alternative polymer manufacturing methodologies. Alternatively, frame 146 may be formed through a 3-D printing process, if desired. Further, different portions of frame 146 (as described above, for example), may be made from a variety of materials and combined using alternative methodologies. For example, attachment arms 164 may be made from a polymer material and combined with a central frame member constructed from a metal. Variations of combining different materials with different portions of frame 146 are contemplated.

FIG. 8 further illustrates that attachment arms 164 may include a variety of shapes. For example, in some instances, attachment arms 164 may include a bow and/or general curvilinear shape (such as that shown in the attachment arm 164 closest to head portion 158). In other examples, an attachment arm 164 may include additional features, such as the circular portion 172 positioned adjacent one or more attachment arms 164 (as shown adjacent two attachment arms 164 located farthest from head portion 158). Similar to that discussed above with respect to circular portion 72 shown in FIG. 4A, the circular portion 172 may be designed to provide a "visual engagement marker" for which a user (e.g., clinician) may be able to engage a secondary medical device and manipulate the position of the frame 146 after initial deployment. In other words, a clinician may be able to engage a secondary medical device with circular portion 172 and thereafter manipulate the secondary medical device to alter the initial deployment position of frame 146.

In some examples, frame 146 may include a variety of shapes and/or geometric arrangements. For example, while the above discussion has focused on the shape of frame 146 shown in FIG. 8, it is not intended to be limiting. For example, frame 146 may include one or more stiffening members 162 extending throughout frame 146, such as throughout body portion 156. Further, stiffening member 162 may be arranged within frame 146 (e.g., within body portion 156) such that it creates the one or more apertures 174. The number, shape, configuration and/or arrangement of stiffening members 162 and/or apertures 174 may depend on the particular performance characteristics desired to be imparted to detachable frame 146. For example, additional stiffening members 162 may be added to frame 146 to provide increased stiffness to frame 146. In other instances, stiffening members 162 may take on particular geometries that increase stiffness or flexibility in a particular direction and/or region while decreasing stiffness or flexibility in a different direction and/or region, for example.

Stiffening members 162 may be located (e.g., arranged) throughout frame 146 in a variety of configurations to provide additional stiffness and/or structural integrity to a particular frame shape. In other words, a wide variety of different shapes and/or arrangements of stiffening members 162 may be included within frame 146 to impart customized performance characteristics on frame 146. For example, in some instances it may be desirable to transfer rotational forces placed on head portion 158 to attachment arms 164 positioned at the distal portion 154 of frame 146. The addition of stiffening members 162 may transfer those rotational forces throughout frame 146 (e.g., to the distal portion 154 of frame 146) while minimizing the amount of force lost and/or dissipated throughout the frame 146 due to undesirable flexing of the frame members.

FIG. 8 further illustrates that frame 146 may include an extension member 180 extending away from head portion 158 (when viewed in the planar configuration shown in FIG. 8). Extension member 180 may include a connection aperture 182 formed in a proximal region 184 of extension member 180. Additionally, extension member 180 may include one or more extension arms 186 extending to a proximal portion of body portion 156. Extension arms 186 may be part of (e.g., a monolithic structure with) body portion 156. FIG. 8 illustrates that extension arms 186 may include a curve. However, it is contemplated that the shape of extension portion 180 (including extension arms 186 and/or aperture 186) may include a variety of shapes and/or configurations.

FIG. 8 further illustrates that frame 146 may include one or more attachment channels 170 located along a distal portion 168 of one or more attachment arms 164. For example, FIG. 8 shows attachment channels 170 positioned at a distal portion 168 of the attachment arms 164. As will be discussed in greater detail below, attachment channels 170 may be utilized to attach the frame 146 to an example implant. While FIG. 8 shows a single attachment channel 170 positioned along a distal portion 168 of each of the attachment arms 164, the illustrated number of attachment channels 170 is not intended to be limiting. In other words, it is contemplated that one or more attachment channels 170 may be positioned along any portion of frame 146. The number of attachment channels 170 positioned along frame 146 may be 1, 2, 3, 4, 5, 6, 7, 8, 9, 10, 15, 20 or more. In other instances, attachment arms 164 may be devoid of attachment channels 170. In such instances, attachment arms 164 may include an alternative attachment structure for attaching to an implant.

When combined with an example implant, frame 146 may be defined as having a first surface that faces away from the implant when the implant is attached to frame 146 (e.g., a first surface that faces away from a target site in the body) and a second surface that faces the example implant (e.g., a second surface that faces a target site in the body). In some instances, attachment channels 170 may extend from the first surface to the second surface. In other words, in some instances, attachment channels 170 may be defined as openings that extend through the thickness of frame 146 from the first surface of the frame 146 that faces away from the implant to the second surface of the frame 146 that faces toward the implant.

Figure 9A:
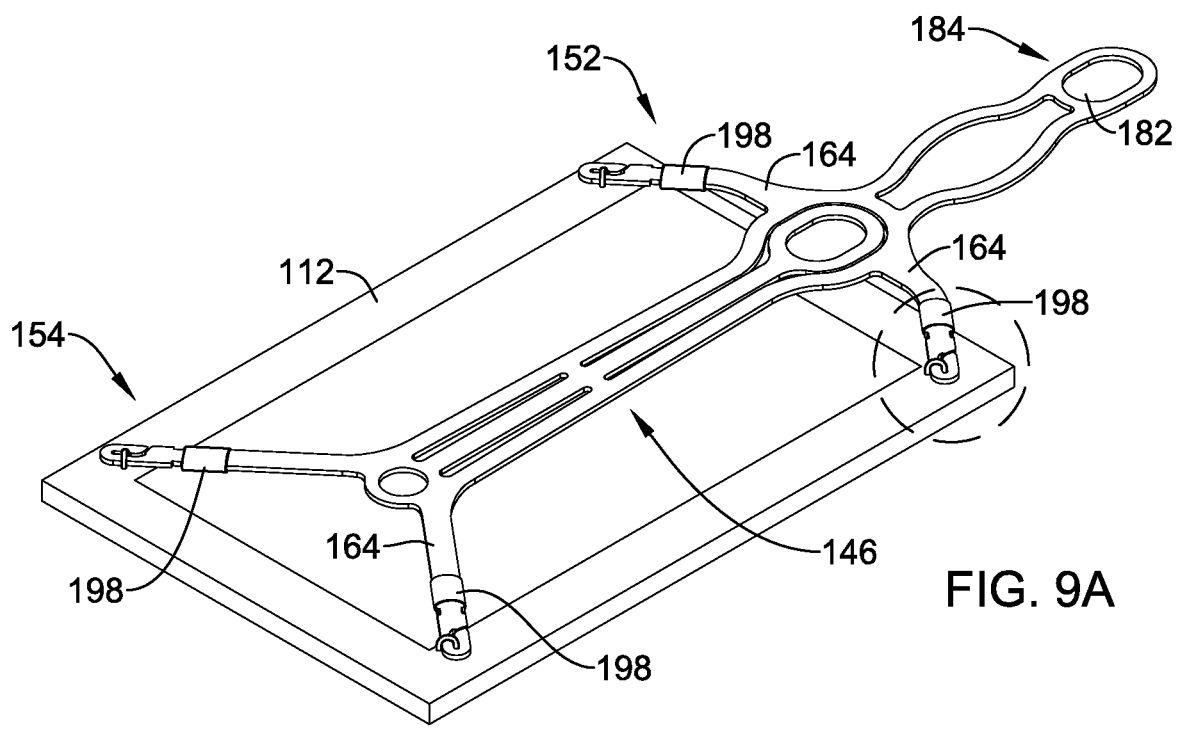
FIG. 9A illustrates another example implant delivery device attached to an implant.

As stated above, attachment channels 170 may be utilized to attach and/or couple frame 146 to an example implant. FIG. 9A shows an example frame 146 attached to an example implant 112. Further, FIG. 9A shows example frame 146 attached to example implant 112 at the distal or free end of each of the four attachment arms 164, respectively. Attachment of free distal ends of attachment arms 164 to implant 112 may be made by any desired attachment mechanism.

As will be described in greater detail below, FIG. 9A further illustrates locking covers 198 positioned along the distal portion 168 of attachment arms 164. Locking cover 190 may be used in conjunction with attachment channels 170 to secure frame 146 to implant 112. Locking covers 198 may be constructed of a variety of materials. For example, locking covers 198 may include a metal, a polymer or combinations thereof, for example.

Figure 9B:
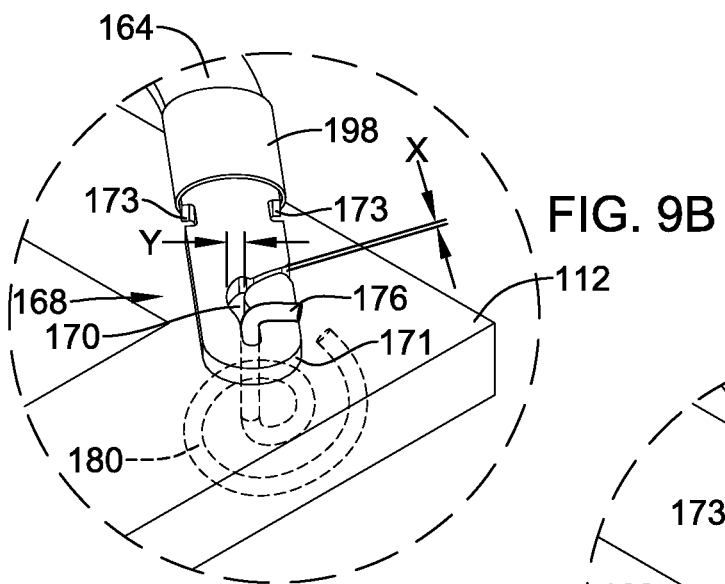
FIG. 9B illustrates an example delivery device attached to an implant.

FIG. 9B shows a detailed view of a portion of frame 146 attached to an implant 112 in a configuration similar to that discussed above with respect to FIGS. 7 and 8. Specifically, FIG. 9B shows example attachment arm 164 including a distal portion 168. Attachment channels 170 are positioned along the distal portion 168 of the attachment arm 164. Additionally, FIG. 9B shows an example attachment member (e.g. wire) 176 extending between and/or through one or more of the attachment channels 170 located on the distal portion 168 of attachment arms 164.

Attachment member 176 may include a variety of structures and/or techniques designed to attach example frame 146 to example implant 112. As shown in FIG. 9B, attachment member 176 may be inserted, looped, wound and/or threaded through one or more attachment channels 170 such that the attachment member 176 is prevented from being pulled away from the distal portion 168 of attachment arm 164. In other words, sliding, inserting and/or winding attachment member 176 through one or more attachment channels 170 may effectively affix attachment member 176 to attachment arm 164. In other words, it is contemplated that attachment member 176 may be affixed to the distal portion 168 of attachment arms 164 (via attachment channels 170, for example) without having either end of the attachment member 176 permanently attached (e.g., welded, etc.) to any structure (e.g., frame 146). In some instances, attachment member 176 may be wrapped and/or looped through attachment channel 170 one or more times to provide a friction fit, interference fit, and/or resistive tension to unraveling or unwinding as a withdrawal force is applied to attachment member 176.

FIG. 9B further illustrates that attachment channel 170 may include an opening that extends through the thickness of attachment arm 164 (e.g., from a top surface to the bottom surface of attachment arm 164) and also that attachment channel 170 may extend through the sidewall 171 of attachment arm 164 such that attachment member 176 may be laterally inserted into and/or removed from attachment channel 170. Additionally, attachment channel 170 may include one or more widths along the length of attachment channel 170. For example, FIG. 9B shows attachment channel 170 including a first width "X" which extends through sidewall 171 of attachment arm 164. Attachment channel 170 further includes a second width "Y." In some instances, width "X" may be narrower than width "Y." Further, it can be appreciated that width "X" may be sized such that it is slightly smaller than the width (e.g., diameter) of attachment member 176. Additionally, the general shape of attachment channel 170 may be designed such that it may flex to an extent sufficient to permit attachment member to extend (e.g., be inserted) through the narrower portion of channel 170 defined by the width "X" and further advanced into the wider portion of channel 170 defined by width "Y."

FIG. 9B further illustrates example detents 173. Detents may extend inwardly from the surface of sidewall 171. In some instances, detents 173 may be designed to mate with a protrusion or tab extending from an inner surface of locking member 198. Alternatively, detents may be protrusions or protuberances extending from the surface of attachment arm 164 configured to engage and/or mate with a feature of locking cover 198.

Similar to that described above with respect to FIG. 5B, FIG. 9B shows an example attachment configuration which may allow frame 146 to detach from implant 112. For example, FIG. 9B shows a portion of attachment member 176 wound in a spiral pattern 180 along the surface of implant 112 facing a target site. In other words, attachment member 176 may form a spiral pattern 180 that remains in a plane substantially parallel to the plane of the surface of implant 112 which faces a target site. Further, it can be appreciated that attachment member 176 may extend from the side of attachment arm 164 facing away from implant 112, through the combined thickness of the attachment arm 164 (e.g., via attachment channel 170) and implant 112, eventually exiting implant 112 on the surface of implant 112 facing a target site. The attachment member 176 may include a retention portion, such as a spiral pattern 180 positioned on the opposite side of implant 112 from attachment arm 164 for coupling implant 112 to attachment arm 164. Further, it can be appreciated that the spiral pattern 180 shown in FIG. 9B is one of a variety of configurations for which attachment member 176 may be wound in order to prevent frame 146 from prematurely releasing from implant 112. Further, as described above, when a sufficient threshold pull-away force is applied to frame 146, the portion of attachment member 176 forming the spiral 180 shown in FIG. 9B may unwind and/or straighten and pull back through implant 112. Instead of spiral 180, it is contemplated that attachment member 176 may have another shaped configuration positioned on the surface of implant 112 facing a target site, which may be straightened or release upon a sufficient removal force to pull back through implant 112.

FIG. 9B further shows locking member 198 positioned along the distal portion 168 of attachment arm 164. In at least some examples disclosed herein, locking member 198 may be able to translate (e.g., slide) along attachment arm 164. For example, FIG. 9B shows the distal portion 168 of attachment arm 164 extending through at least a portion of locking member 198. In such instances, locking member 198 may be a sleeve in which attachment arm 164 extends through lumen of sleeve. In at least some examples disclosed herein, locking member 198 is designed such that there is sufficient clearance between the inner surface (e.g., the inner diameter) of locking member 198 and the outer surface (e.g., the outer diameter) of attachment arm 164 such that locking member 198 can slide along attachment arm 164.

Figure 9C:
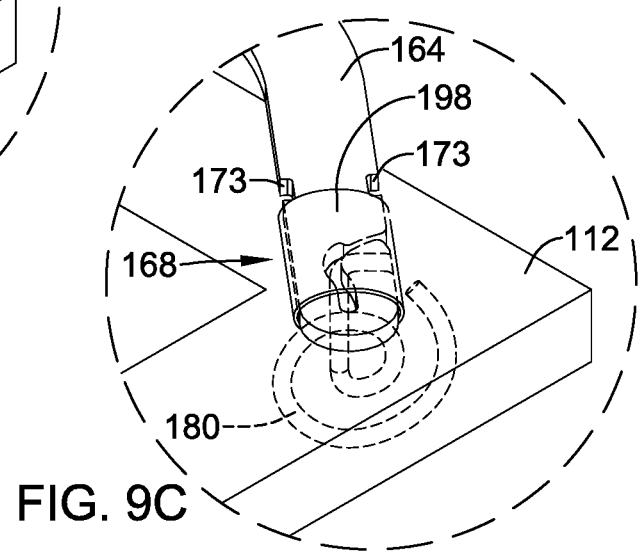
FIG. 9C illustrates an example delivery device attached to an implant.

It can further be appreciated that locking member 198 may slide along attachment arm 164 to a position in which locking member 198 covers attachment member 176 and/or attachment channel 170. For example, FIG. 9C shows locking member 198 positioned at the distal end 168 of the attachment arm 164. Further, FIG. 9C shows locking member 198 positioned over the top (e.g., covering) of attachment member 176 and attachment channel 170. It can be appreciated that when positioned over the top of the attachment member 176 and/or attachment channel 170, locking member 198 may pinch, hold, secure, and/or lock attachment member 176 to attachment arm 164, such as by securing or locking attachment member 176 in attachment channel 170. In some examples, locking member 198 may resemble a "compression-like" fitting wherein locking member 198 is drawn over the top of attachment member 176, thereby compressing attachment member 176 onto attachment arm 164 such that attachment member 176 is prevented from separating from attachment arm 164.

Additionally, when locking member 198 is positioned over the top of attachment member 176 and/or attachment channel 170, locking member 198 may lock in place via detents 173. In other words, when locking member 198 is positioned in its securement position, in which the attachment member 176 is secured to attachment arm 164, a feature of locking member 198 engages detents 173 to inhibit or prevent locking member 198 from moving back to the unsecured position shown in FIG. 9B. For example, it can be appreciated that the locking member 198 may include one or more inwardly projecting tabs (not shown) designed to be inserted (e.g., mate with) detents 173. The combination of tabs and detents 173 are, therefore, designed to prevent locking member 198 from moving along attachment arm 164 after having been positioned over top the attachment member 176 and/or attachment channel 170.

During assembly of implant 112 to frame 146, attachment member 176 may be passed through implant 112 with distal enlarged portion (e.g., spiral 180) positioned on a second surface of implant 112 facing away from frame 146. Portion of attachment member 176 extending from a first surface of implant 112 facing frame 146 may then be passed through attachment channel 170, such as passed laterally into attachment channel 170 and then bent, wound or otherwise manipulated around attachment arm 164. Locking member 198 may then be moved from a first, unsecured position, shown in FIG. 9B to a second, secured position, shown in FIG. 9C to secure attachment member 176 to attachment arm 164.

The above discussion describes example configurations of the distal end portions of the attachment arms and provides example configurations of how the attachment arms may be connected to an example implant. However, these configurations are not intended to be limiting. Rather, a variety of attachment arm configurations are contemplated. For example, FIG. 9D shows a detailed view of a portion of another example frame 246 attached to implant 112 in a configuration similar to that discussed above with respect to FIGS. 9A-9C.

Figure 9D:
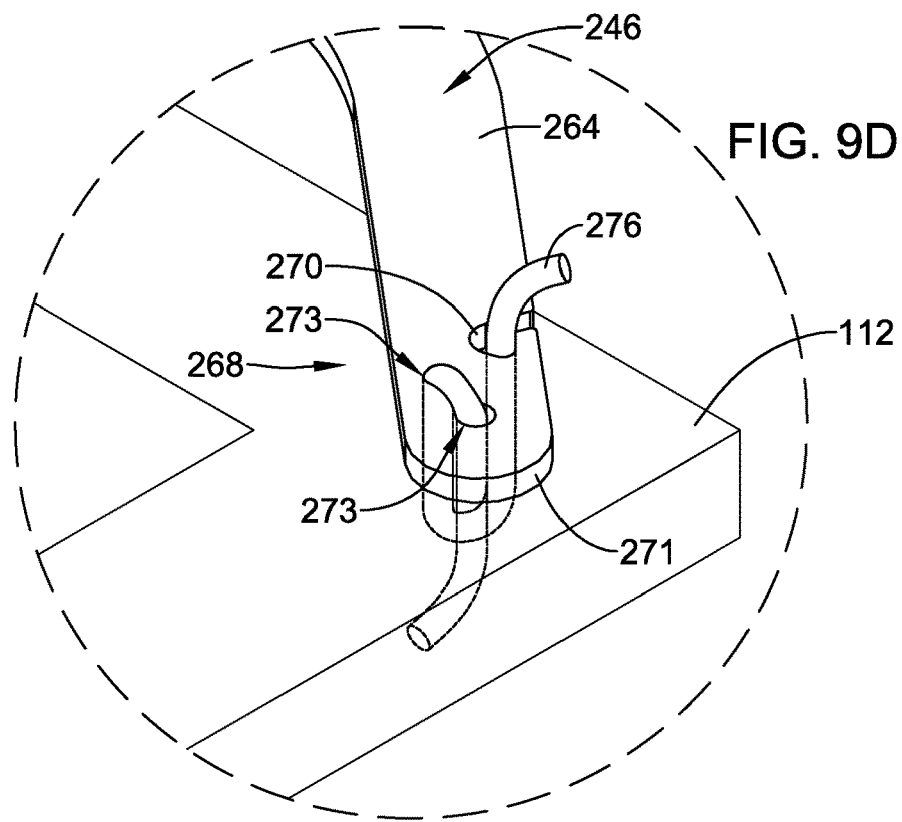
FIG. 9D illustrates an example delivery device attached to an implant.

Specifically, FIG. 9D shows example attachment arm 264 including a distal portion 268. An attachment channel 270 is positioned along the distal portion 268 of the attachment arm 264. Additionally, FIG. 9D shows an example attachment member (e.g. wire) 276 extending through the attachment channel 270 located on the distal portion 268 of attachment arm 264. FIG. 9D further illustrates that the distal portion 268 of the attachment arm 264 may include one or more openings 273 that extend through the thickness of attachment arm 264 (e.g., from a top surface to the bottom surface of attachment arm 264) and also that attachment channel 270 may extend through the sidewall 271 of attachment arm 264 such that attachment member 276 may be laterally inserted into and/or removed from attachment channel 270. As illustrated in FIG. 9D, attachment member 276 may be looped through one or more openings 273 and implant 112 (the dashed line in FIG. 9D depicts the attachment member 276 being looped through implant 112) in addition to being secured within attachment channel 270.

Attachment member 276 may include a variety of structures and/or techniques designed to attach example frame 246 to example implant 112. As shown in FIG. 9D, attachment member 276 may be inserted, looped, wound and/or threaded through one or more attachment channels 270 and/or openings 273 such that the attachment member 276 is prevented from being pulled away from the distal portion 268 of attachment arm 264. In other words, sliding, inserting and/or winding attachment member 276 through one or more attachment channels 270 and/or openings 273 may effectively affix attachment member 276 to attachment arm 264. In other words, it is contemplated that attachment member 276 may be affixed to the distal portion 268 of attachment arms 264 (via attachment channels 270 and/or openings 273, for example) without having either end of the attachment member 276 permanently attached (e.g., welded, etc.) to any structure (e.g., frame 246). In some instances, attachment member 276 may be wrapped and/or looped through attachment channel 270 and/or openings 273 one or more times to provide a friction fit, interference fit, and/or resistive tension to unraveling or unwinding as a withdrawal force is applied to attachment member 276.

Figure 9E:
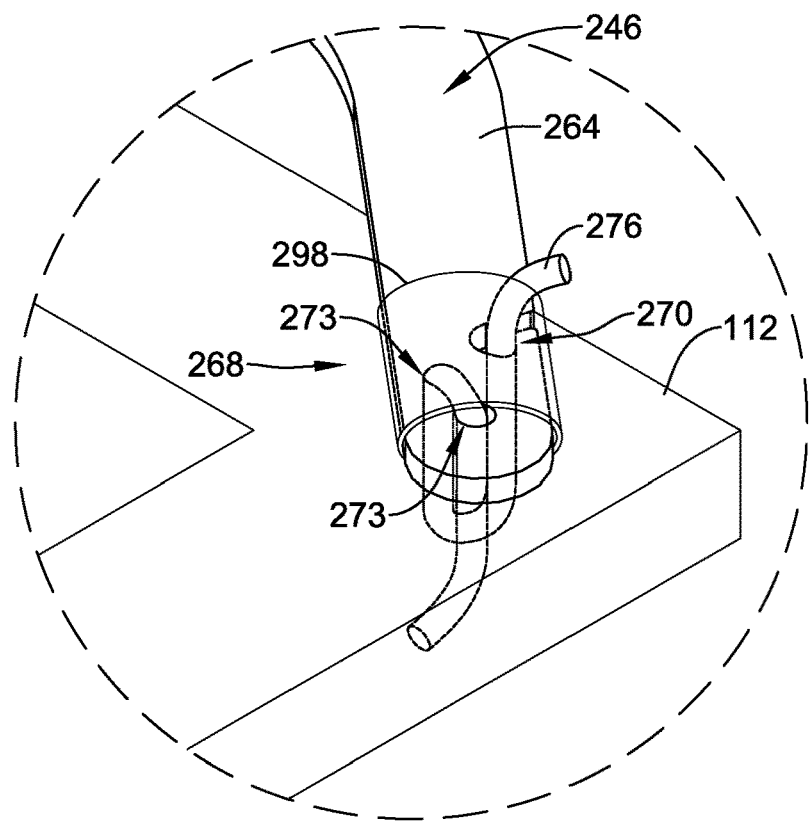
FIG. 9E illustrates an example delivery device attached to an implant.

Further, FIG. 9E illustrates that in some examples, a locking member 298 may be molded directly onto and/or otherwise positioned on the distal portion 268 of attachment arm 264. For example, FIG. 9E shows an example locking member 298 positioned along the distal portion 268 of the attachment arm 264 whereby the locking member 298 covers at least a portion of the attachment member 276 and/or attachment channel 270. Further, FIG. 9E shows locking member 298 encircling (e.g., covering) attachment member 276 and attachment channel 270. It can be appreciated that when molded over attachment member 276 and/or attachment channel 270, the locking member 298 may pinch, hold, secure, and/or lock attachment member 276 to attachment arm 264, such as by securing or locking attachment member 276 in attachment channel 270 and/or openings 273. In some examples, locking member 298 may compress attachment member 276 onto attachment arm 264 such that attachment member 276 is prevented from separating from attachment arm 264. It is contemplated that any of the examples described herein may utilize a sliding locking member 198 (as shown and described in FIGS. 9A-9C) and/or an over-molded locking member 298 (as shown and described in FIG. 9E).

Figure 10:
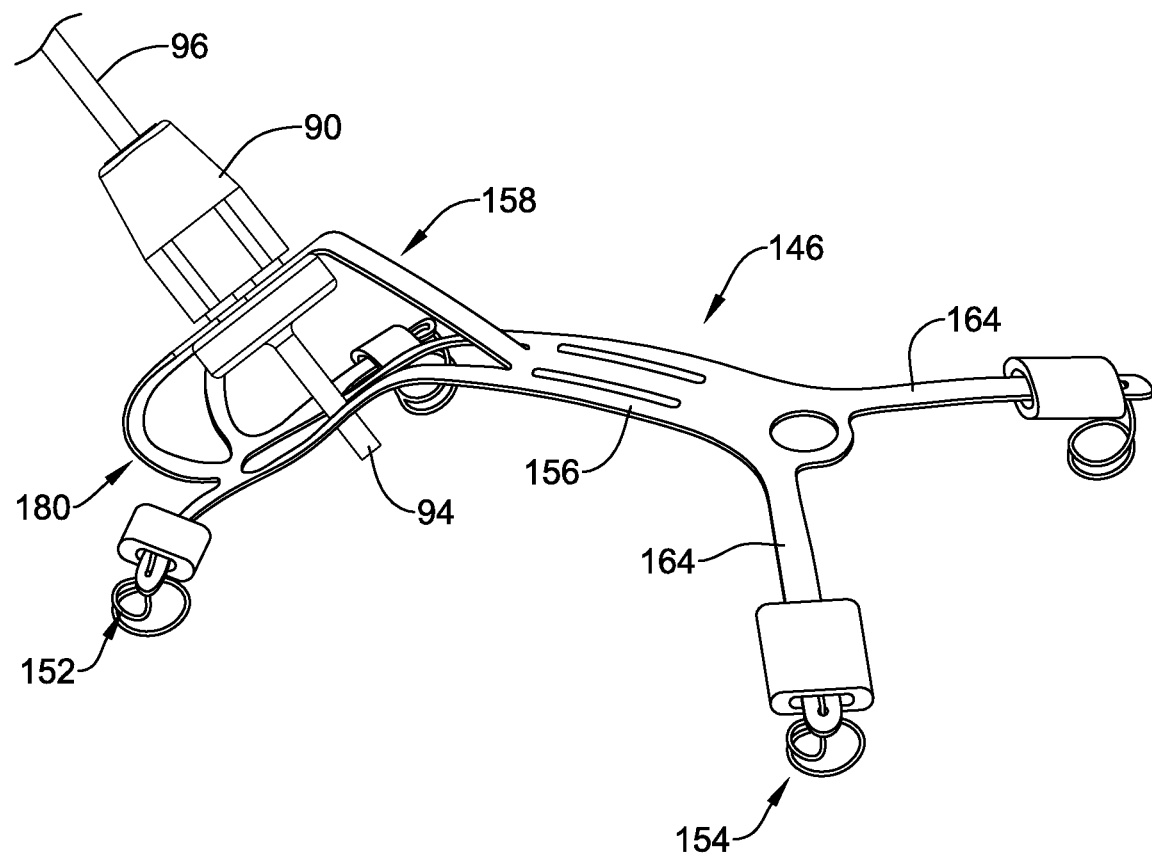
FIG. 10 illustrates another example implant delivery device.

FIG. 10 illustrates a perspective view of frame 146 representing the configuration frame 146 would be in when inserted into the body. For example, FIG. 10 shows frame 146 including extension member 180 coupled to both connection member 90 (similar in form and function to connection member 90 discussed above) and head portion 158. As discussed above, FIG. 10 illustrates that a tether 96 (similar in form and function to tether 96 discussed above) may be coupled to connection member 90 and extend proximally therefrom. Further, as illustrated in FIG. 10, extension member 180 may curve upward and back on itself (e.g., upward and back toward the distal end 154 of frame 146). Further, head portion 158 may extend upward and away from the body portion 156 of frame 146. It can be appreciated that connection member 90 may couple extension member 180 to head portion 158 via the apertures 182 and 160. In other words, connection member 90 may be inserted through both apertures 182 and 160, thereby securing extension member 180 to head portion 158. Additionally, FIG. 10 shows a tack member 94 extending through a portion of frame 146. Tack member 94 will be described in greater detail below.

Additionally, FIG. 10 illustrates that frame 146 may form a concave configuration when being inserted into the body. It can be appreciated that the concave shape of frame 146 may follow the contour of anatomy (e.g., shoulder) in which the example implant is to be secured.

Figure 11:
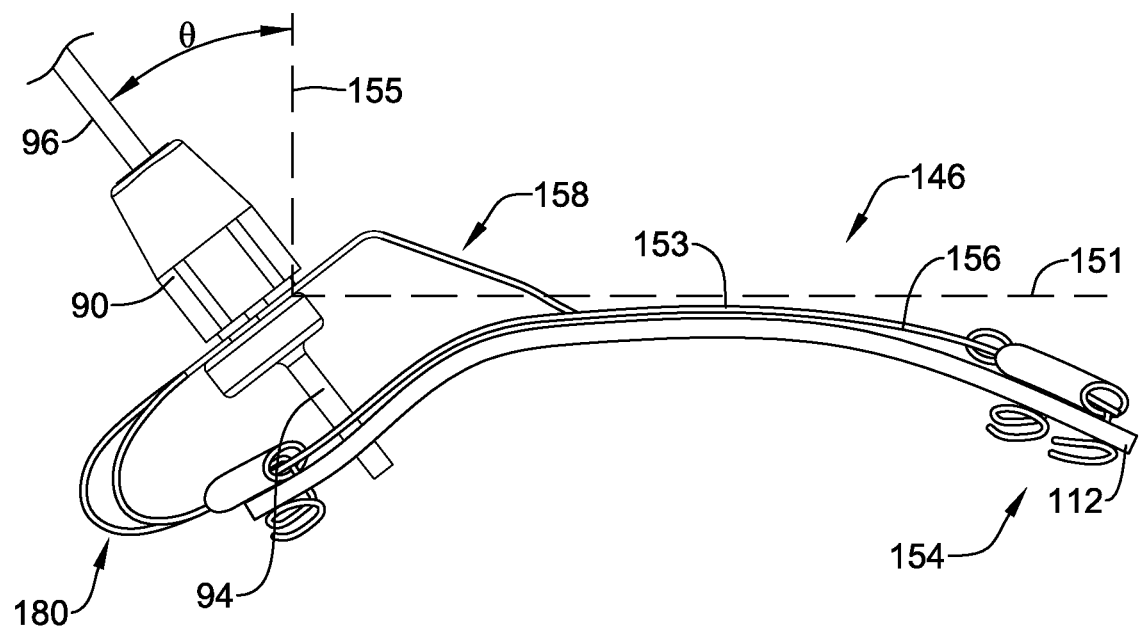
FIG. 11 illustrates another example implant delivery device.

FIG. 11 illustrates a side view of frame 146 described in FIG. 10. FIG. 11 illustrates the concave shape of frame 146. Additionally, FIG. 11 shows extension member 180 curving upward and back toward distal portion 154 of frame 146 as described above. Further, FIG. 11 shows head portion 158 extending upward and away from body portion 156 of frame 146. Extension member 180 and the head portion 158 are coupled to one another via connection member 90 extending through connection apertures 182, 160. Thus, connection apertures 182, 160 may be coaxial, with connection member 90 extending therethrough. Additionally, FIG. 11 shows tack member 94 extending through a portion of frame 146, such that the distal tip of tack member 94 penetrates through implant 112 to be positioned a distance below the lower surface (the surface of implant 112 opposite the frame 146) of implant 112. FIG. 11 further illustrates the tether member 96 described above with respect to FIG. 10. In some examples, the tether member 96 may be coupled to the tack member 94. While the above discussion describes the tether member 96 indirectly coupled to frame member 146 via the connection member 90, it is contemplated that in other instances the tether member 96 may be directly coupled to frame 146 (or other similar frame members described herein).

In some instances, the configuration of frame 146 shown in FIGS. 7-11 may provide both precise control and maneuverability to a clinician or other operator of the medical device. For example, the geometry of the extension member 180 in combination with head portion 158 and connection member 90 may provide precise maneuverability of the distal portion 154 of frame 146. For example, in some instances, an operator may manipulate connection member 90 with a delivery shaft 44 (described above). The delivery shaft may be able to impart a downward force (e.g., a force directed toward a patient's shoulder) onto frame 146 via the combination of connection member 190, extension member 180 and head portion 158. Further, the concave geometry of frame 146 may allow the distal portion of frame 146 to extend along the surface of the shoulder for which the implant 112 is to be positioned. In other words, the geometry of frame 146 shown in FIG. 10 and FIG. 11 may prevent the distal portion 154 of frame 146 (including attachment arms 164) from pulling up and away from the shoulder surface as a clinician manipulates frame 146 within the body. Further, the geometry of frame 146 shown in FIGS. 10 and 11 may allow the distal portion 154 of frame 146 to be advanced toward the surface of the shoulder in which an implant 112 is to be positioned.

Additionally, the geometry of frame 146 shown in FIG. 11 may allow a clinician improved visibility of the frame 146 (e.g., the distal portion 154 of frame 146) during implantation of the medical device. For example, in some instances a clinician may position a camera adjacent the implantation site. The clinician may utilize the camera to accurately maneuver and/or position an example implant into the patient. However, in some instances, the camera my obscure and/or impede the visibility of all or a portion of the frame or implant (e.g., frame 146 and/or implant 112). However, the geometry of frame 146 shown in FIG. 11 may allow the connection member 90 (and delivery sheath 44 coupled to connection member 90) to be inserted at an angle (depicted as "θ" in FIG. 11) which is directed away from the distal end 154 of frame 146. It can be appreciated that angle θ may be measured from a line 155 that is orthogonal to a line 151 tangent to a point 153 generally positioned at the apex of a curve defined by body portion 156. Orienting connection member 90 such that it is directed away from the distal end 154 of frame 146 may increase the amount of space for which a camera may be placed during a procedure. In other words, a clinician may be able to maneuver the camera such that it provides improved visibility of all or a portion of the medical device being implanted (e.g., implant 112 via frame 146).

Figure 12A:
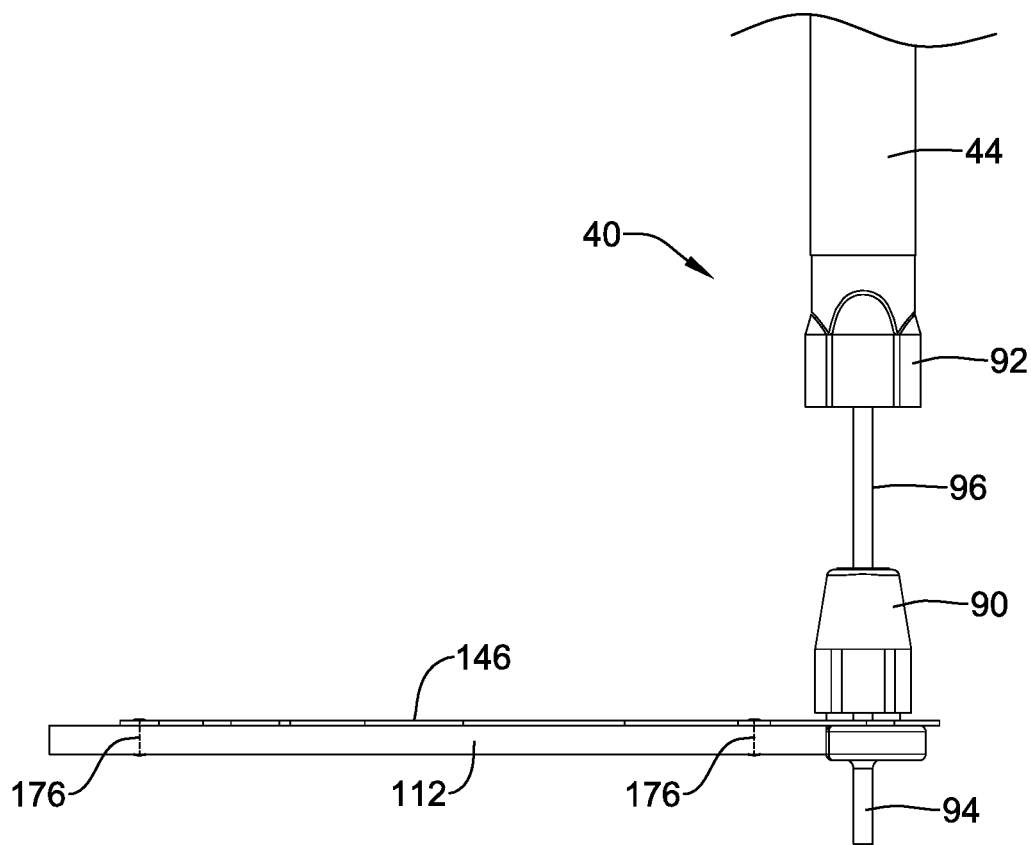
FIG. 12A illustrates a plan view of another example implant delivery device.

As briefly described above with respect to FIGS. 10 and 11, any of the implant delivery systems described herein may include a tack member designed to "anchor" the delivery system in place prior to a clinician affixing implant 12 to the bone and/or tendon. For example, FIG. 12A illustrates a tack member 94 extending distally from the first connection member 90. As shown in FIG. 12A, tack member 94 may extend distally from first connection member 90 and be substantially perpendicular to implant 12 and/or frame 46. In some instances, tack member 94 may extend generally parallel to the longitudinal axis of delivery sheath 42 and/or delivery shaft 44 with the frame 46 and implant 12 extending generally perpendicular to the longitudinal axis of delivery sheath 42 and/or delivery shaft 44. However, this configuration is not intended to be limiting. Rather, it is contemplated that tack member 94 may extend distally from the first connection member 90 and/or frame 46 at an oblique angle to the longitudinal axis of delivery sheath 42, delivery shaft 44, and/or frame 46.

In some instances, tack member 94 may resemble a cylindrical pin or rod extending away from frame 46. The tack member 94 may be designed to be rigid enough to be pounded and/or inserted into bone. For example, in some instances, a clinician may apply a force to a proximal portion of the implant delivery system 40 (e.g., delivery shaft 44) such that tack member 94 may be "hammered" into a body structure (e.g., bone). In some instances, tack member 94 may include a tapered distal tip, which may be a sharpened or blunt tapered distal tip in some instances.

In some instances, tack member 94 may be stationary (e.g., fixed in place) relative to frame 46 and/or first connection member 90 of connection assembly 88. For example, tack member 94 may extend distally from first connection member 90 and away from the surface of frame 46 which faces a target site.

While the above discussion describes example tack member 94, the discussion relative thereto is not intended to be limiting. Rather, a variety of tack member designs and configurations are contemplated herein. Different tack members may be designed to impart specific insertion forces while the tack is being driven into a body structure (e.g., bone). Additionally, these tack designs may also provide specific release forces upon removing the tack from a body structure (e.g., bone).

Figure 12B:
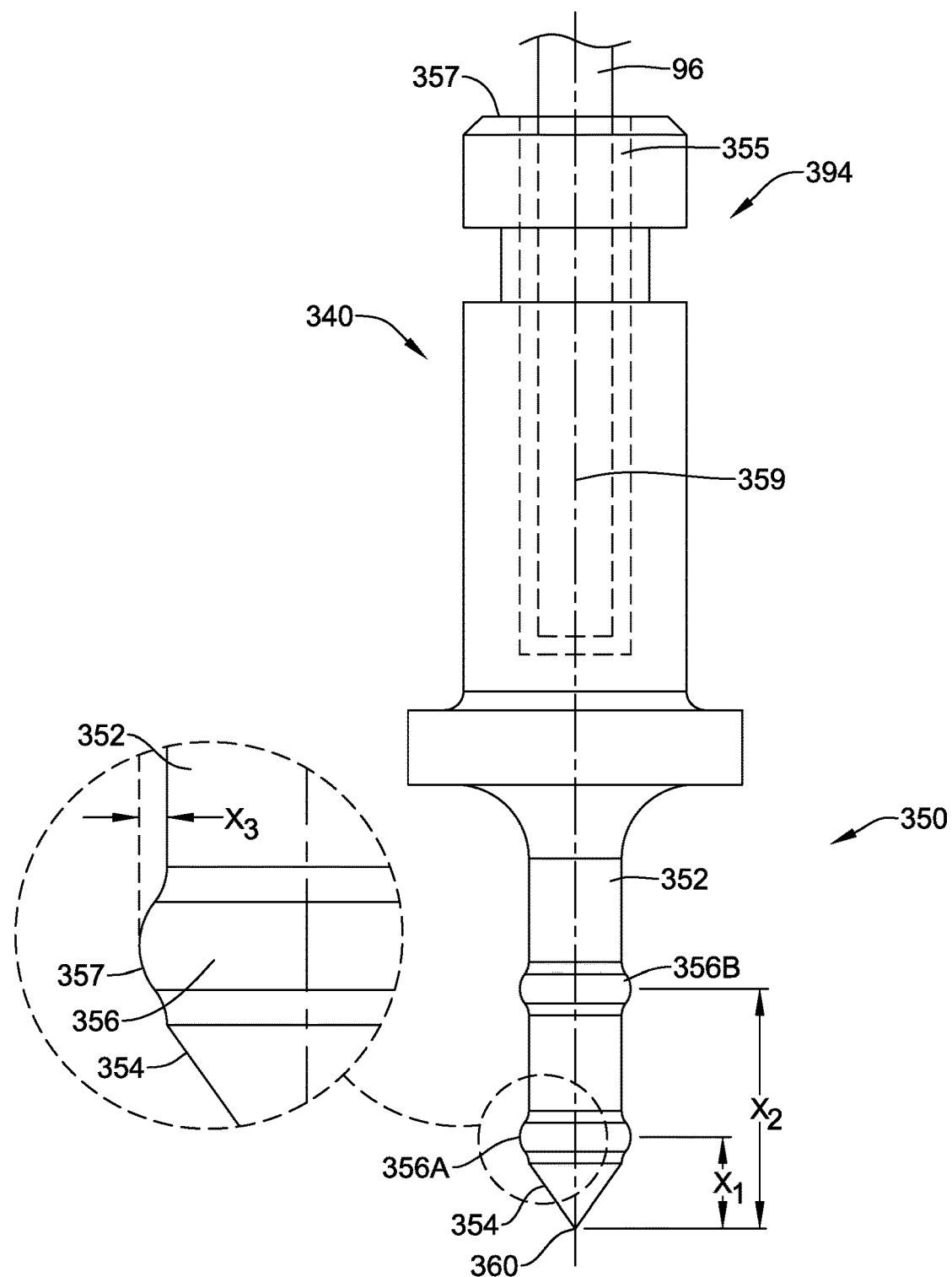
FIG. 12B illustrates an example tack member.

For example, FIG. 12B illustrates another tack member 394. Tack member 394 may include a proximal end region 340 and a distal end region 350. The distal end region 350 may include shaft member 352 and a tip member 354. The tip member 354 may be positioned at the distal end of the shaft member 352. Additionally, in some examples the tack member 394 may include one or more radially enlarged portions positioned along the shaft member 352. Radially enlarged portions may be protuberances or lobes (e.g., continuous or discontinuous circumferential and/or helical rims, etc.) extending radially outward beyond the outer surface of the shaft member 352, for example. For example, FIG. 12B shows a first radially enlarged portion 356A and a second radially enlarged portion 356B positioned along the shaft member 352. However, it is contemplated that the tack member 394 may include a single radially enlarged portion or more than two radially enlarged portions. For example, the tack member 394 may include 1, 2, 3, 4, 5, 6, 7, 8 or more radially enlarged portions. In some examples, the first radially enlarged portion 356A may be positioned adjacent tip member 354.

In some examples the proximal end region 340 of the tack member 394 may include a vertical bore 355 extending inward from a proximal end surface 357 of the tack member 394. The vertical bore 355 may extend along the longitudinal axis 359 of the tack member 394. Additionally, FIG. 12B illustrates the tether member 96 (discussed with respect to FIG. 12A) extending within the vertical bore 355. As shown in FIG. 12B, the vertical bore 355 may include a profile which mirrors the shape of the tether member 96 extending within the vertical bore 355. It can further be appreciated that the tether member 96 may be attached to the tack member 394 via the vertical bore 355. In other words, the tether member 96 may be rigidly fixed to the tack member 394 within the vertical bore 355 via a variety of attachment techniques (e.g., welding, adhesive, crimping, swaging, etc.) The diameter of the tether member 96 is illustrated as being less than the diameter of the vertical bore 355, however, it is noted that upon securement of the tether member 96 within vertical bore 355, the tether member 96 may substantially occupy the bore 355.

FIG. 12B illustrates that the first radially enlarged portion 356A and the second radially enlarged portion 356B may be spaced longitudinally away from one another along the shaft member 352 with a portion of the shaft 352 positioned therebetween. For example, FIG. 12B shows the distance at which each of the first radially enlarged portion 356A and the second radially enlarged portion 356B are spaced away from the distal end 360 of the tip member 354. For example, "$X_1$" depicts the distance at which the first radially enlarged portion 356A is spaced away from the distal end 360 of the tip member 354. In some examples, $X_1$ may be between 0.030 inches and 0.090 inches, or may be between 0.045 inches and 0.075 inches, or may be about 0.059 inches, for example. Additionally, "$X_2$" depicts the distance at which the second radially enlarged portion 356B is spaced away from the distal end 360 of the tip member 354. In some examples, $X_2$ may be between 0.100 inches and 0.150 inches, or may be between 0.115 inches and 0.130 inches, or may be about 0.124 inches.

However, it is further contemplated that in some examples the first radially enlarged portion 356A and the second radially enlarged portion 356B may be adjacent one another. In other words, it is contemplated that the first radially enlarged portion 356A and the second radially enlarged portion 356B may be positioned directly adjacent one another. It is further contemplated that in some examples the tack member 394 may include more than two radially enlarged portions, some of which may be positioned away from other radially enlarged portions and/or some of which may be positioned directly adjacent other radially enlarged portions.

Additionally, the detailed view of FIG. 12B illustrates that the first radially enlarged portion 356A and/or the second radially enlarged portion 356B may include a curved portion 357 having an outer surface which extends laterally away from the outer surface of the shaft member 352 located adjacent to the curved portion 357. In other words, the curved portion 357 of the radially enlarged portion 356 may have an outer diameter which is greater than the outer diameter of the shaft member 352 directly adjacent the curved portion 357. For example, the detailed view of FIG. 12B depicts the distance that curved portion 357 extends radially outward from the surface of the shaft member 352 as "$X_3$." In some examples, $X_3$ may be between 0.001 inches and 0.015 inches, or may be between 0.005 inches and 0.010 inches, or may be about 0.006 inches. In some examples, the distance that a first radially enlarged portion and a second radially enlarged portion extends away from the surface of the shaft member 352 may be different. For example, a more proximal radially enlarged portion may extend radially outward from the shaft member 352 a greater distance or a lesser distance than a more distal radially enlarged portion. In other examples (like those described above), the distance that a first radially enlarged portion and a second radially enlarged portion extends away from the surface of the shaft member 352 may be substantially equivalent.

It can be appreciated that the distance that curved portion 357 extends radially away from the surface of the shaft member 352 may correspond to the force required to retract the tack member 394 from a body structure into which the tack 394 may be inserted. It can further be appreciated that the shape, geometry, materials, etc. of the tack member 394 may be tailored to impart specific withdrawal forces from a body structure into which the tack member 394 may be inserted.

Additionally, in some instances, the shaft member 352 may include a taper. For example, the shaft member 352 may be tapered at an angle relative to the longitudinal axis 359 of the shaft member 352. In some examples, angle of taper may be about 1 degree to about 5 degrees, for example.

Figure 12C:
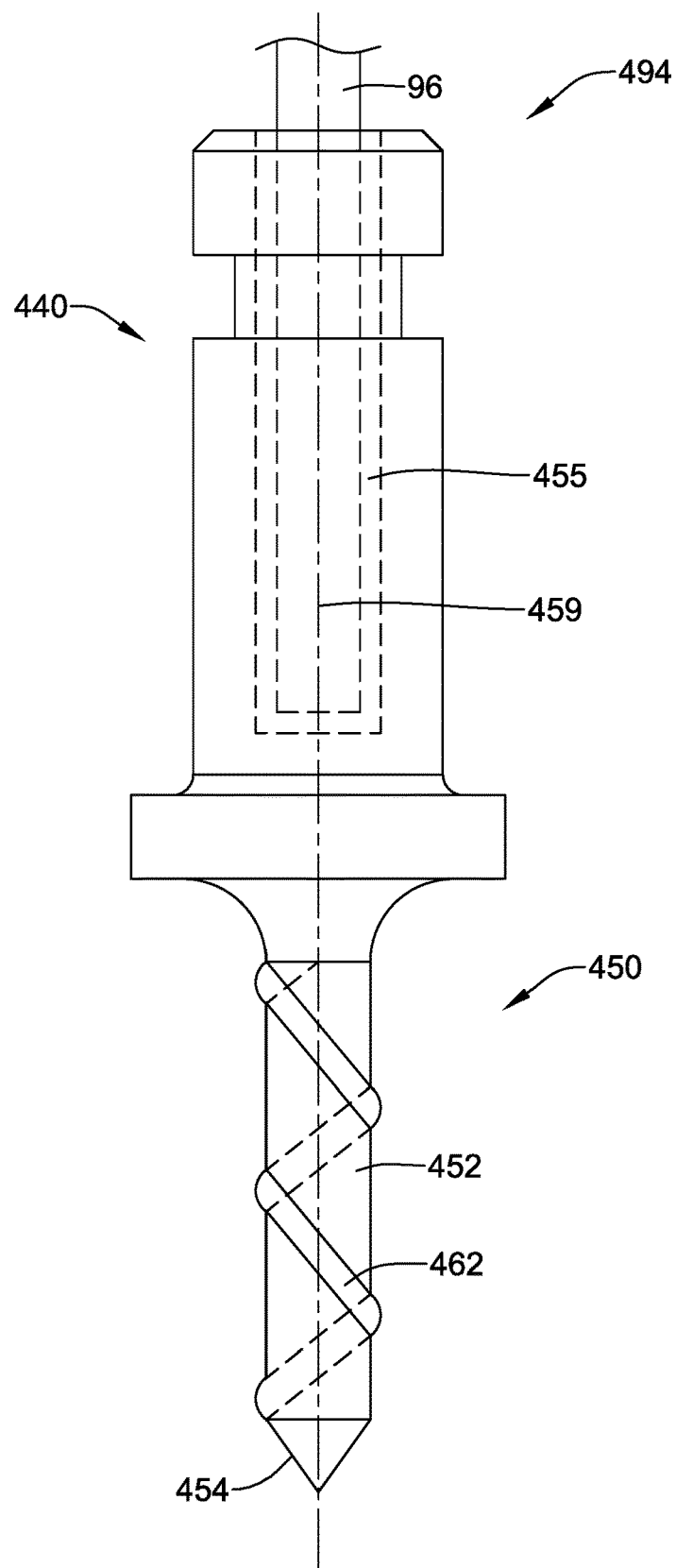
FIG. 12C illustrates another example tack member.

FIG. 12C illustrates another example tack member 494. The tack member 494 may be similar in form and function to other tack members described herein. For example, tack member 494 may include a proximal end region 440 and a distal end region 450. The distal end region 450 may include shaft member 452 and a tip member 454. The tip member 454 may be positioned at the distal end of the shaft member 452. The tack member 494 may further include the vertical bore 455. FIG. 12C illustrates the tether member 96 extending within the vertical bore 455. The tether member 96 may be attached to the tack member 494 via the vertical bore 455 as described above.

Additionally, FIG. 12C illustrates that shaft member 452 may include one or more radially enlarged portions 462 positioned helically along the shaft member 452. Similarly to the radially enlarged portions 356A/356B described above with respect to FIG. 12B, the helical radially enlarged portion 462 may include a curved portion having an outer surface which extends radially outward beyond the outer surface of the shaft member 452. As illustrated in FIG. 12C, the helical radially enlarged portion 462 may extend longitudinally along the shaft member 452 in a helical fashion. Additionally, while FIG. 12C shows a single helical radially enlarged portion extending along the surface of the shaft member 452, it is contemplated that the tack member 494 may include more than one helical radially enlarged portion 462. For example, tack member 494 may include two helical radially enlarged portions helically arranged along the shaft member 452. In some examples, first and second helical radially enlarged portions may extend around shaft member 452 in the same helical direction (e.g., a clockwise direction or a counterclockwise direction) along shaft member 452. In some examples, first and second helical radially enlarged portions may extend around shaft member 452 in opposite directions (e.g., a first helical radially enlarged portion extending in a clockwise direction and a second helical radially enlarged portion may extend in a counterclockwise direction) along shaft member 452.

Figure 12D:
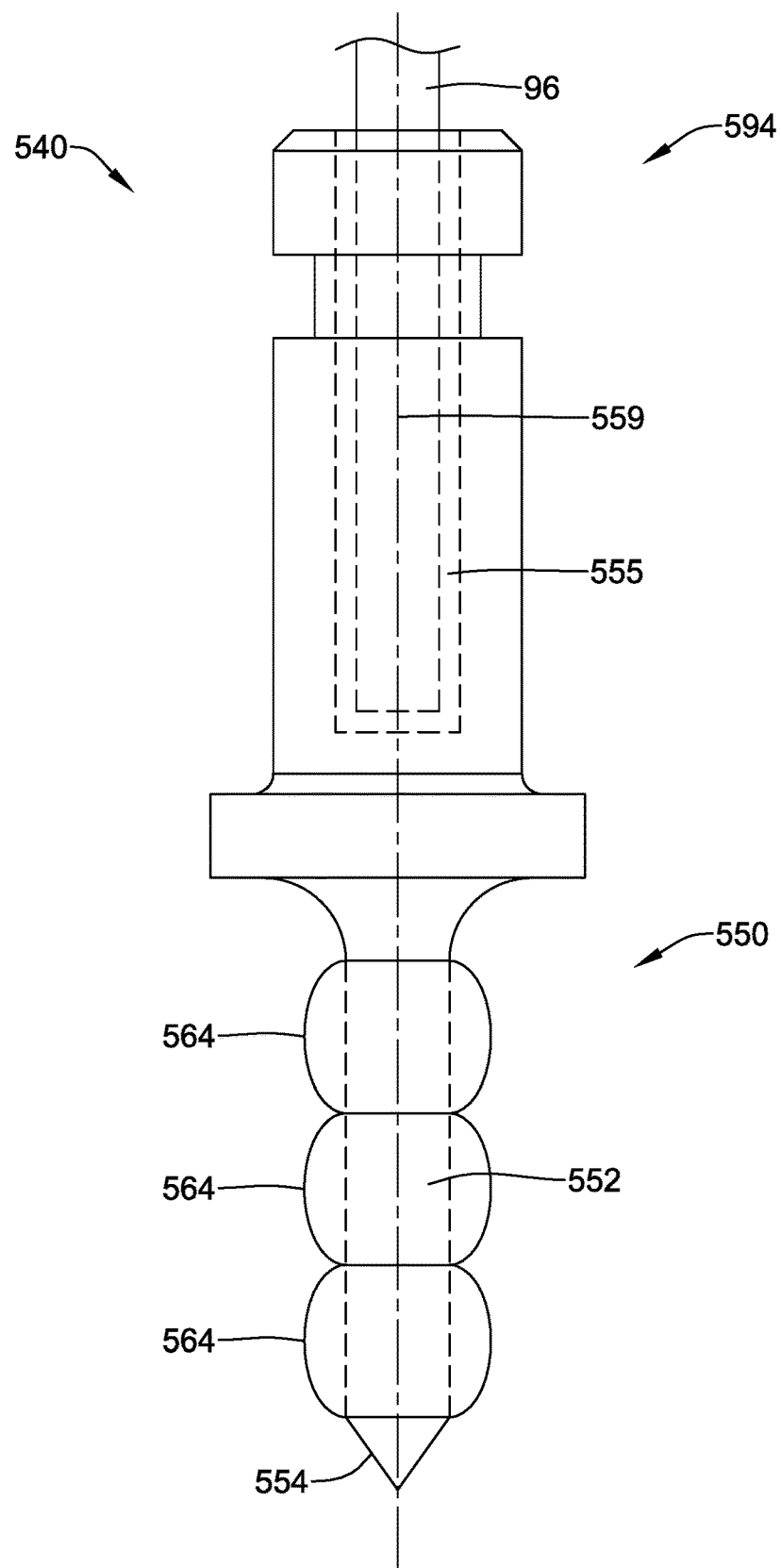
FIG. 12D illustrates another example tack member.

FIG. 12D illustrates another example tack member 594. The tack member 594 may be similar in form and function to other tack members described herein. For example, tack member 594 may include a proximal end region 540 and a distal end region 550. The distal end region 550 may include shaft member 552 and a tip member 554. The tip member 554 may be positioned at the distal end of the shaft member 552. The tack member 594 may further include the vertical bore 555. FIG. 12D illustrates the tether member 96 extending within the vertical bore 555. The tether member 96 may be attached to the tack member 594 via the vertical bore 555 as described above.

Additionally, FIG. 12D illustrates that tack member 594 may be formed as a composite structure including multiple components formed of dissimilar materials. For example, tack member 594 may include shaft member 552 along with one or more fixation members 564 disposed along the shaft member 552 (depicted by the dashed line in FIG. 12D). As shown in FIG. 12D, the fixation members 564 may be constructed from materials different from the material used to construct the shaft member 552. For example, the fixation members 564 may be formed from a material which is softer and/or more flexible than the material used to construct the shaft member 552, thus permitting the fixation members 564 to be radially compressible toward the longitudinal axis of the tack member 594. The fixation members 564 may include a polymeric material, composite material, or any other material with desirable compression/expansion characteristics, while the shaft member 552 may be formed of a metallic material, for example.

As illustrated in FIG. 12D, the one or more fixation members 564 may surround or otherwise extend radially outward from the surface of the shaft member 552 with the shaft member 552 extending through the one or more fixation members 564. In some instances, the one or more fixation members 564 may be positioned in one or more grooves or recesses formed in an outer surface of the shaft member 552. It can be appreciated that the fixation members 564 may be designed to provide a specific withdrawal force from a body structure into which the tack member may be inserted. For example, the fixation members 564 may be designed from a material having a selected modulus which allows the material to be compressed while inserted into a body structure. However, this material may also permit the fixation members 564 to impart a specific radially-outward force against the body structure while inserted into the body structure. This radially-outward force may correspond to the force required to remove the tack member 594 from the body structure. Thus, radial compression of the fixation members 564 may be necessary for insertion of the tack member 594 into a body structure (e.g., bone) and removal of the tack member 594 from the body structure (e.g., bone). The materials, number, geometry, spacing, etc. utilized for the fixation members 564 may be tailored to provide a particular "release" force corresponding to a maximum threshold force that a clinician may want to impart on tack member 564 to remove it from the body structure.

Figure 12E:
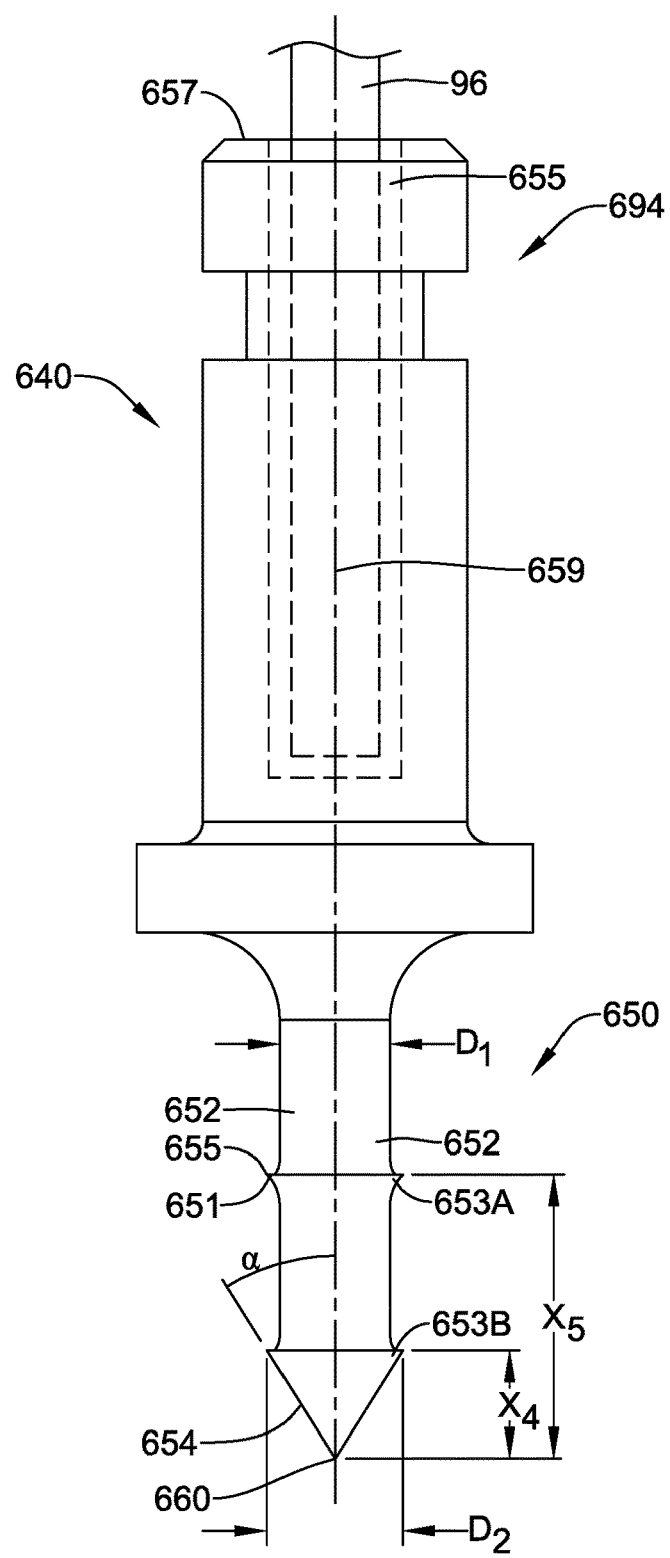
FIG. 12E illustrates another example tack member.

FIG. 12E illustrates another tack member 694. Tack member 694 may include a proximal end region 640 and a distal end region 650. The distal end region 650 may include shaft member 652 and a tip member 654. The tip member 654 may be positioned at the distal end of the shaft member 652. Additionally, in some examples the tack member 694 may include one or more radially extending portions positioned along the shaft member 652. Radially extended portions may be protuberances (e.g., continuous or discontinuous circumferential and/or helical flats, etc.) extending radially outward beyond the outer surface of the shaft member 652, for example. For instance, FIG. 12E shows a radially extending portion 653A positioned along the shaft member 652 and extending radially outward from the outer surface of shaft member 652. Additionally, FIG. 12E shows a second radially extending portion 653B positioned adjacent to and/or extending from tip member 654. However, it is contemplated that the tack member 694 may include a single radially extending portion or more than two radially extending portions. For example, the tack member 694 may include 1, 2, 3, 4, 5, 6, 7, 8 or more radially extending portions. In some examples, the first radially enlarged portion 652A may be positioned adjacent tip member 654.

In some examples, the proximal end region 640 of the tack member 694 may include a vertical bore 655 extending inward from a proximal end surface 657 of the tack member 694. The vertical bore 655 may extend along the longitudinal axis 659 of the tack member 694. Additionally, FIG. 12E illustrates the tether member 96 (discussed with respect to FIG. 12A) extending within the vertical bore 655. As shown in FIG. 12E, the vertical bore 655 may include a profile which mirrors the shape of the tether member 96 extending within the vertical bore 655. It can further be appreciated that the tether member 96 may be attached to the tack member 694 via the vertical bore 655. In other words, the tether member 96 may be rigidly fixed to the tack member 694 within the vertical bore 655 via a variety of attachment techniques (e.g., welding, adhesive, crimping, swaging, etc.) The diameter of the tether member 96 is illustrated as being less than the diameter of the vertical bore 655, however, it is noted that upon securement of the tether member 96 within vertical bore 655, the tether member 96 may substantially occupy the bore 655.

FIG. 12E illustrates that the first radially extending portion 653A and the second radially extending portion 653B may be spaced longitudinally away from one another along the shaft member 652 with a portion of the shaft 652 positioned therebetween. For example, FIG. 12E shows the distance at which each of the first radially extending portion 653A and the second radially enlarged portion 653B are spaced away from the distal end 660 of the tip member 654. For example, "$X_5$" depicts the distance at which the first radially extending portion 653A is spaced away from the distal end 660 of the tip member 654. In some examples, $X_5$ may be between 0.090 inches and 0.175 inches, or may be between 0.115 inches and 0.150 inches, or may be about 0.127 inches, for example. Additionally, "$X_4$" depicts the distance at which the second radially extending portion 653B is spaced away from the distal end 660 of the tip member 654. In some examples, $X_4$ may be between 0.025 inches and 0.100 inches, or may be between 0.050 inches and 0.075 inches, or may be about 0.062 inches.

However, it is further contemplated that in some examples the first radially extending portion 653A and the second radially enlarged portion 653B may be adjacent one another. In other words, it is contemplated that the first radially extending portion 653A and the second radially enlarged portion 653B may be positioned directly adjacent one another. It is further contemplated that in some examples the tack member 694 may include more than two radially extending portions, some of which may be positioned away from other radially extending portions and/or some of which may be positioned directly adjacent other radially extending portions.

Additionally, the detailed view of FIG. 12E illustrates that the first radially enlarged portion 653A and/or the second radially enlarged portion 653B may include a rim or lip portion 651 having a radially extending tip 655 which extends laterally away from the outer surface of the shaft member 652. The radially extending portion 653A (including rim or lip portion 651) may have an outer diameter which is greater than the outer diameter of the shaft member 652. For example, FIG. 12E shows the diameter of the rim or lip portion 651 extending radially outward from the surface of the shaft member 652 as "$D_2$" and the diameter of the shaft member 652 as "$D_1$." In some examples, $D_2$ may be between 0.035 inches and 0.100 inches, or may be between 0.050 inches and 0.075 inches, or may be about 0.070 inches. Further, in some examples, $D_1$ may be between 0.010 inches and 0.075 inches, or may be between 0.025 inches and 0.060 inches, or may be about 0.044 inches. In some examples, the distance that a first radially extending portion 653A and second radially extending portion 653B extends away from the surface of the shaft member 652 may be different. For example, a more proximal radially extending portion may extend radially outward from the shaft member 652 a greater distance or a lesser distance than a more distal radially extending portion. In other examples (like those described above), the distance that a first radially extending portion and a second radially extending portion extends away from the surface of the shaft member 652 may be substantially equivalent.

It can be appreciated that the distance that radially extending portions 653A/653B extend radially away from the surface of the shaft member 652 may correspond to the force required to retract the tack member 694 from a body structure into which the tack 694 may be inserted. It can further be appreciated that the shape, geometry, materials, etc. of the tack member 694 may be tailored to impart specific withdrawal forces from a body structure into which the tack member 694 may be inserted.

Further, in one example tack member 94 may be the first portion of delivery system 40 that exists the distal end 48 of delivery sheath 42 when the frame 46 and delivery shaft 44 are advanced out of the delivery sheath 42 upon deployment of the delivery system 40. In some instances, as the delivery sheath 42 is advanced through an insertion site toward a target site, the frame 46 (to which implant 12 is attached) and a stationary tack member 94 may be fully housed within the lumen 84 of delivery sheath 48. Additionally, as the delivery shaft 44 is advanced out the distal end 48 of the delivery sheath 44, the stationary tack member 94 may be driven directly into an adjacent structure (e.g., bone).

Figure 13A:
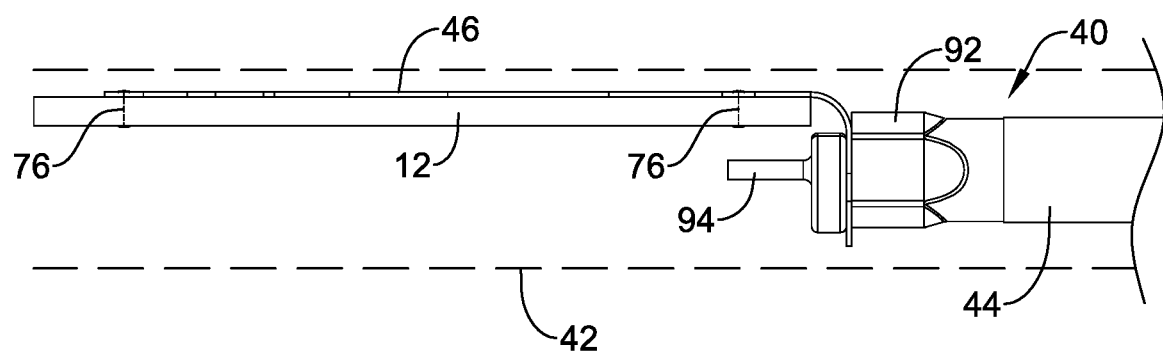
FIG. 13A illustrates a side view of another example implant delivery device with the sheath in cross-section.

However, in other examples, frame member 46 and implant 12 may be positioned within delivery sheath 42 (depicted as dashed line) as shown in FIG. 13A. FIG. 13A shows frame member 46 (with implant 12) substantially aligned longitudinally with delivery shaft 44 and tack member 94. In this example, the distal portion 54 of frame 46 and implant 12 may be located distal of tack member 94 within delivery sheath 42, and thus the first portion of delivery system 40 that exits the distal end 48 of delivery sheath 42 when the frame 46 and delivery shaft 44 are advanced out of the delivery sheath 42 upon deployment of the delivery system 40.

Figure 13B:
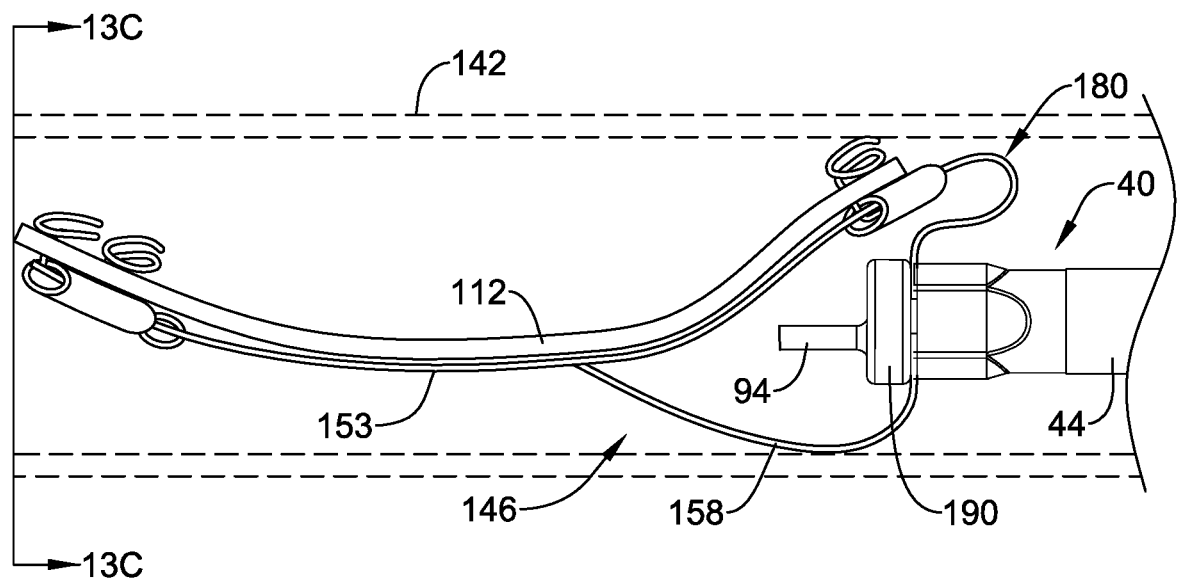
FIG. 13B illustrates a side view of another example implant delivery device with the sheath in cross-section.

In yet other examples, the frame member 146 and implant 112 may be positioned within delivery sheath 42 as shown in FIG. 13B. Further, FIG. 13B shows frame member 146 (and implant 112) substantially aligned longitudinally with delivery shaft 44 and tack member 94. In this example, the distal portion of frame 146 and implant 112 may be located distal of tack member 94 within delivery sheath 42, and thus the first portion of delivery system 140 that exits the distal end of delivery sheath 42 when the frame 146 and delivery shaft 44 are advanced out of the delivery sheath 42 upon deployment of the delivery system 40.

Figure 13C:
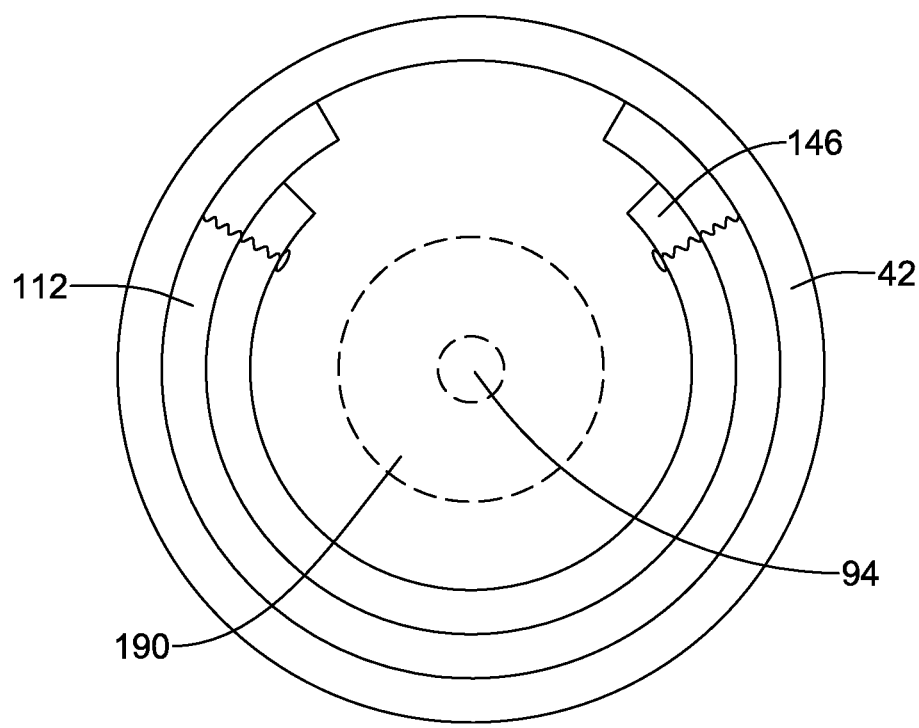
FIG. 13C illustrates an end view along line 13C-13-C of FIG. 13B.

Additionally, FIG. 13C illustrates that implant 112 may be rolled up and positioned between frame member 146 and the delivery sheath 42. Further, it can be appreciated that when positioned in delivery sheath 42 as illustrated in FIG. 13B, implant 112 may wrap around frame member 146 with frame member 146 located radially inward of implant 112, and thereby extend along all or a portion of the inner surface of delivery sheath 42. Upon exiting the distal end of delivery sheath 42, implant 112 may unwrap to a configuration illustrated in FIG. 10 and FIG. 11.

Figure 14:
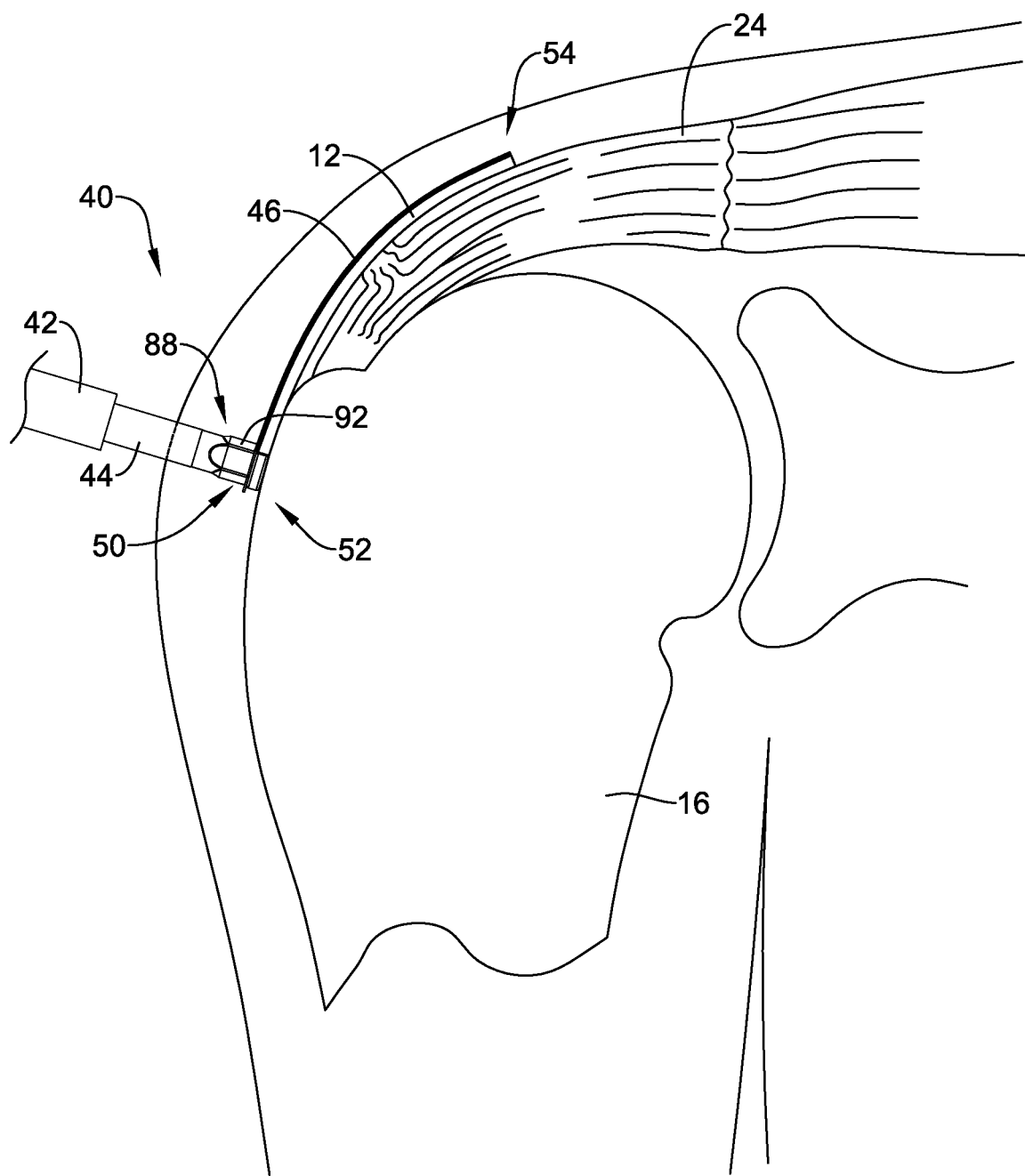
FIGS. 14-18 illustrate an exemplary method of installing an implant with an example implant delivery device at a target site.

In other examples, tack member 94 may translate (e.g., slide, move, etc.) along a longitudinal axis within a lumen (not shown) of first connection member 90 of connection assembly 88. For example, FIG. 14 shows example deployment system 40 positioned adjacent an example target site. FIG. 14 shows the proximal portion 52 of the frame 46 (along with implant 12) positioned adjacent the humeral head 16. In this position, the distal portion 54 of the frame 46 is positioned adjacent the tendon 24. FIG. 14 further illustrates that the tack member 94 has not been advanced and/or extended out of the first connection member 90 of connection assembly 88 and driven into the humeral head. Rather, the tack member 94 remains positioned within the connection assembly 88 (e.g., positioned within first connection member 90). However, in some examples contemplated herein, tack member 94 may be advanced out of the distal portion of delivery shaft 44 and/or connection assembly 88. In other words, the tack member 94 translates (e.g., slides, moves, etc.) relative to connection assembly 88 and advances away from the distal end 50 of delivery shaft 44.

Figure 15:
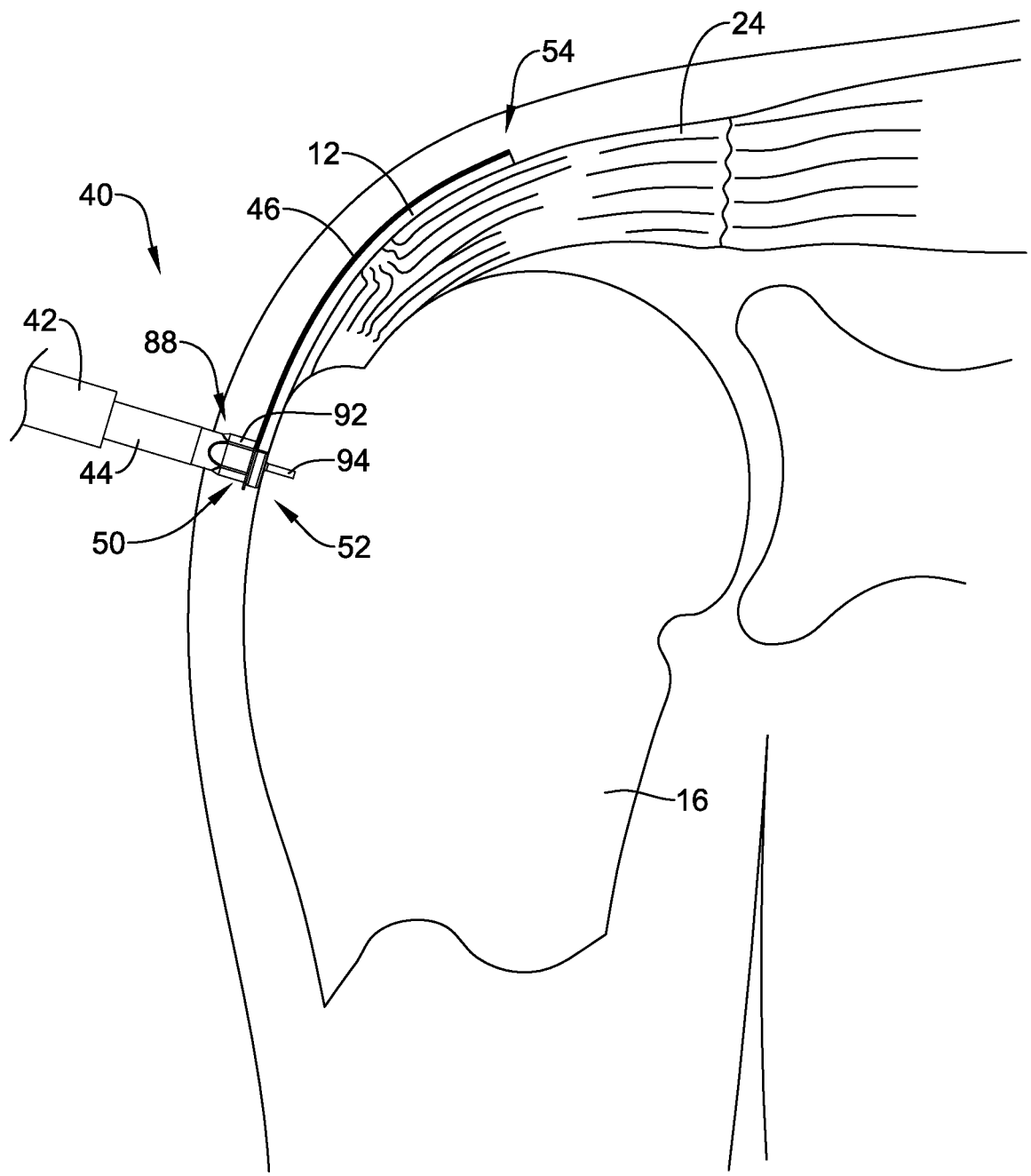

FIG. 15 illustrates tack member 94 being advanced out of the distal portion 50 of delivery shaft 44 after delivery shaft 44 (along with frame 46 and implant 12) have been maneuvered and/or positioned adjacent an example target site. In some examples, FIG. 15 may depict delivery system 40 (discussed with respect to FIGS. 7 and 8) after the tack member 94 has been advanced out of the distal end 50 of the delivery shaft 44 (e.g., advanced distally of first connection member 90) and into the humeral head 16. As discussed above, tack member 94 may be advanced out of the distal end 50 of delivery shaft 44 via the application of a force at the proximal end of the delivery system 40 and/or actuation of an actuation mechanism to move tack member 94 relative to first connection member 90. In some instances, a handle component may be utilized to generate a force to advance tack member 94 along a longitudinal axis of delivery shaft 44 and exit the distal end 50 of delivery shaft 44 distal of first connection member 90.

Figure 15A:
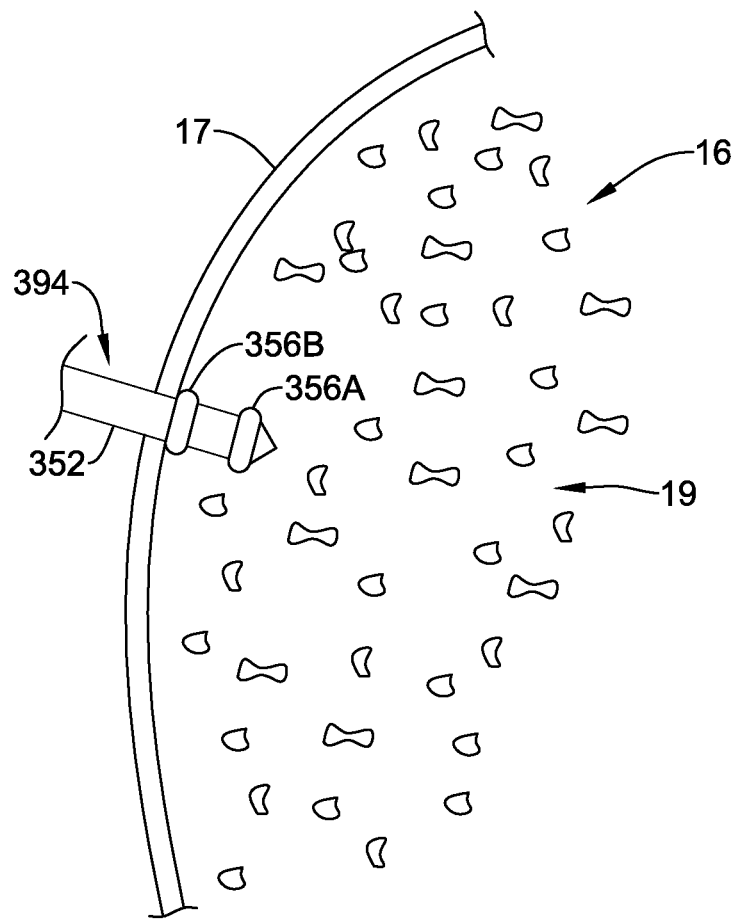

FIG. 15A illustrates the anchoring mechanism of the example tack member 394 (discussed above). As discussed with respect to FIG. 15, in some examples the tack member 94 (of which tack member 394 shown in FIG. 15A is a variation) may be anchored into the humeral head 16 of the humerus (a portion of which is shown in FIG. 15A). As shown in FIG. 15A, the humeral head 16 may include a cortical shell 17 covering a layer of soft bone 19. The cortical shell may be referred to as "hard" bone. FIG. 15A further illustrates that in some instances it may be desirable to advance the tack member 394 through the layer of cortical bone such that the first radially enlarged portion 356A and/or the second radially enlarged portion 357A is positioned beneath the cortical bone layer. In other words, the tack member 394 may be advanced into the humeral head 16 such that the first radially enlarged portion 356A and/or the second radially enlarged portion 357A is positioned within the layer of soft bone, wherein the first radially enlarged portion 356A and/or the second radially enlarged portion 357A provide resistance to being pulled back through the underside of the cortical bone layer. In instances in which the first radially enlarged portion 356A and/or the second radially enlarged portion 357A are made of a compressible material, the first radially enlarged portion 356A and/or the second radially enlarged portion 357A may be compressed as the first radially enlarged portion 356A and/or the second radially enlarged portion 357A are passed through the cortical shell 17. It can be appreciated that the amount of resistance provided by the first radially enlarged portion 356A and/or the second radially enlarged portion 357A may depend on the specific size and geometry of the first radially enlarged portion 356A and/or the second radially enlarged portion 357A.

In some instances, once tack member 94 has been anchored into a target site (as described above), it may be desirable to remove the delivery shaft 44 to make room for additional instruments to be advanced adjacent the target site. FIG. 16 illustrates removing delivery shaft 44 from the target site (depicted by the arrow in FIG. 16) while the frame 46 and implant 12 remain anchored to the humeral head 16 via the tack member 94. As discussed above, delivery shaft 44 may be detached from frame 46 via uncoupling (e.g., detaching) second connection member 92 from first connection member 90.

In some instances, it may be desirable to reengage delivery shaft 44 after detaching second connection member 92 from first connection member 90. For example, in some instances, the bone (e.g., humeral head) in which tack member 94 is initially inserted may be abnormally soft or hard, and therefore, may require additional force to either maintain placement (e.g., if the bone is too soft) or to remove (e.g., if the bone is too hard). Therefore, a clinician may choose to reinsert and reengage shaft member 44 to frame 46 via re-coupling second connection member 92 to first connection member 90, such as after implant 12 has been attached to a target site via one or more bone and/or tendon staples, as described below. Alternatively, shaft member 44 may remain engaged to frame 46 while attaching implant 12 to a target site via one or more bone and/or tendon staples, as described below. The clinician may then be able to apply additional force to frame 46 and/or tack member 92 when attaching implant 12 to an example target site via one or more bone and/or tendon staples.

Figure 17:
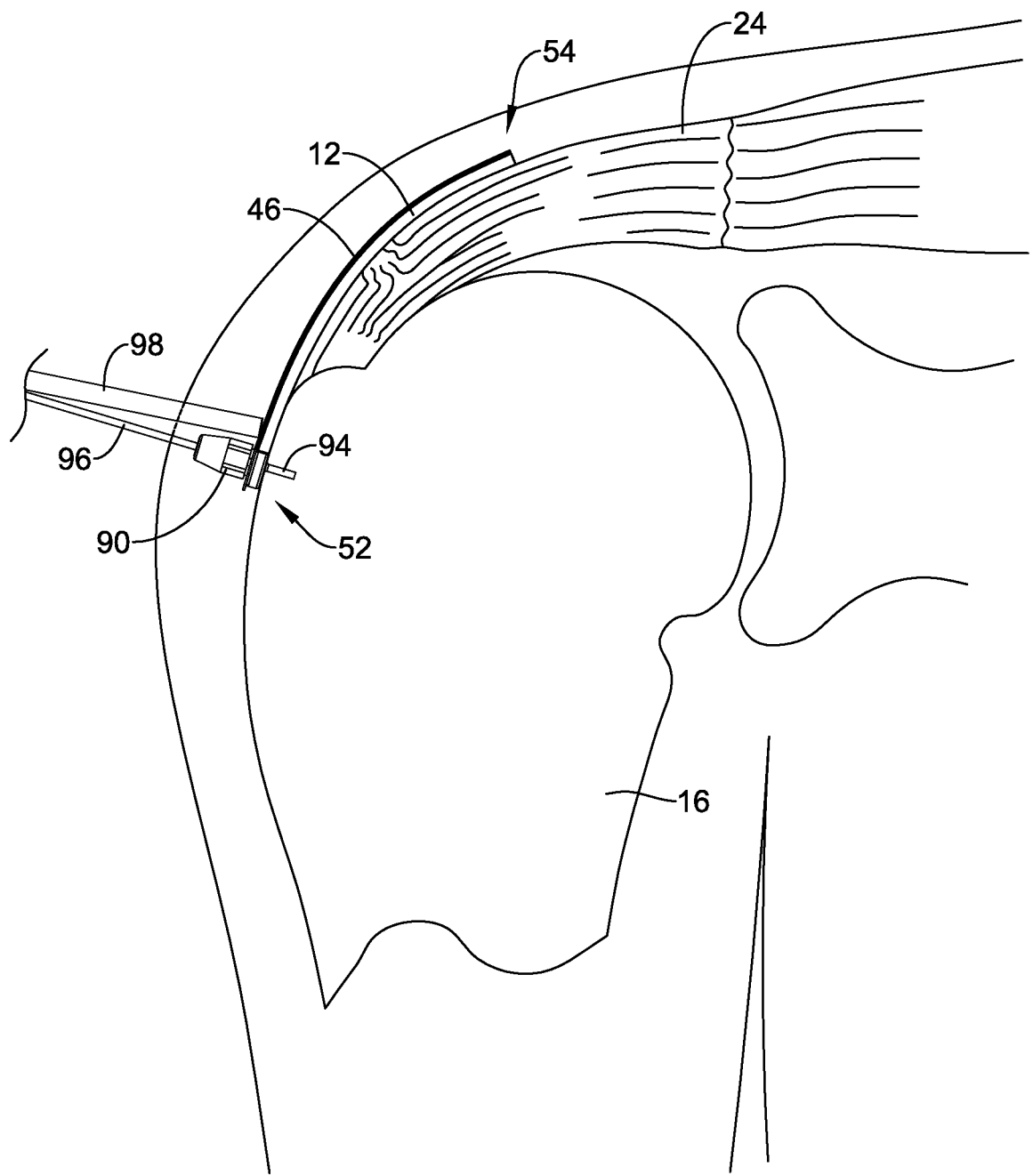

As discussed above, delivery system 40 may include a tether 96 directly or indirectly coupled to frame 46. It can be appreciated that tether 96 may remain attached to frame 46 (e.g., via first connection member 90) and extend to a location exterior of the patient through insertion site (i.e., incision) with delivery shaft 44 detached from frame 46 and removed from insertion site (i.e., incision) while additional instruments are advanced through the insertion site and to the target site. For example, FIG. 17 shows a medical instrument 98 (e.g., implant stapler) positioned adjacent the proximal end 52 of the frame 46 and implant 12. As discussed above and shown in FIG. 17, tether 96 remains attached to frame 46 (e.g., via first connection member 90) and is positioned exterior of and alongside example medical instrument 98. The medical instrument 98 may be used to attach implant 12 to treatment site, such as with one or more, or a plurality of staples and/or sutures.

As discussed above, in some instances, implant 12 may be affixed to a target site after which the frame 46 may be detached (and removed) from both implant 12 and the target site. For example, in some instances, implant 12 may be attached to a target site via one or more bone and/or tendon staples. The staples may be applied to the target site via a stapling instrument (e.g., medical instrument 98).

Further, in some instances, it may be beneficial to affix implant 12 to the bone portion of the target site (e.g., humeral head 16) prior to affixing the implant to the tendon portion 24 of the target site. For example, it may be beneficial for a clinician to orient and/or position the frame 46 and implant 12 in the location/arrangement shown in FIG. 17 prior to affixing the implant to the target site. As shown in FIG. 17 (and previously discussed) the implant is positioned such that the proximal portion 52 of the frame 46 and implant 12 are positioned adjacent the humeral head 16, while the distal portion 54 is positioned adjacent the tendon 24. Once the frame 46 and implant 12 have been placed appropriately, it may be desirable to utilize a stapling instrument to first insert staples along the proximal portion 52 of the implant (e.g., the portion of the implant 12 positioned adjacent the bone) and into bone, followed by insertion of staples along the sides and distal portion of implant 12 and into tendon tissue.

It can be further appreciated that because the examples disclosed herein allow for the removal of the delivery sheath 42 and delivery shaft 44 prior to insertion of the stapling instrument, sufficient room exists to manipulate the stapling instrument in order to accurately place the staples along the proximal portion 52 of the implant adjacent the humeral head 16.

Additionally, as discussed above, the tack member 94 may anchor the frame 46 and implant 12 in place (e.g., to the bone 16), thereby allowing a clinician to remove the delivery shaft 44 without fear that the frame/implant 46/12 combination will change position prior to the insertion of staples into the implant 12.

Figure 18:
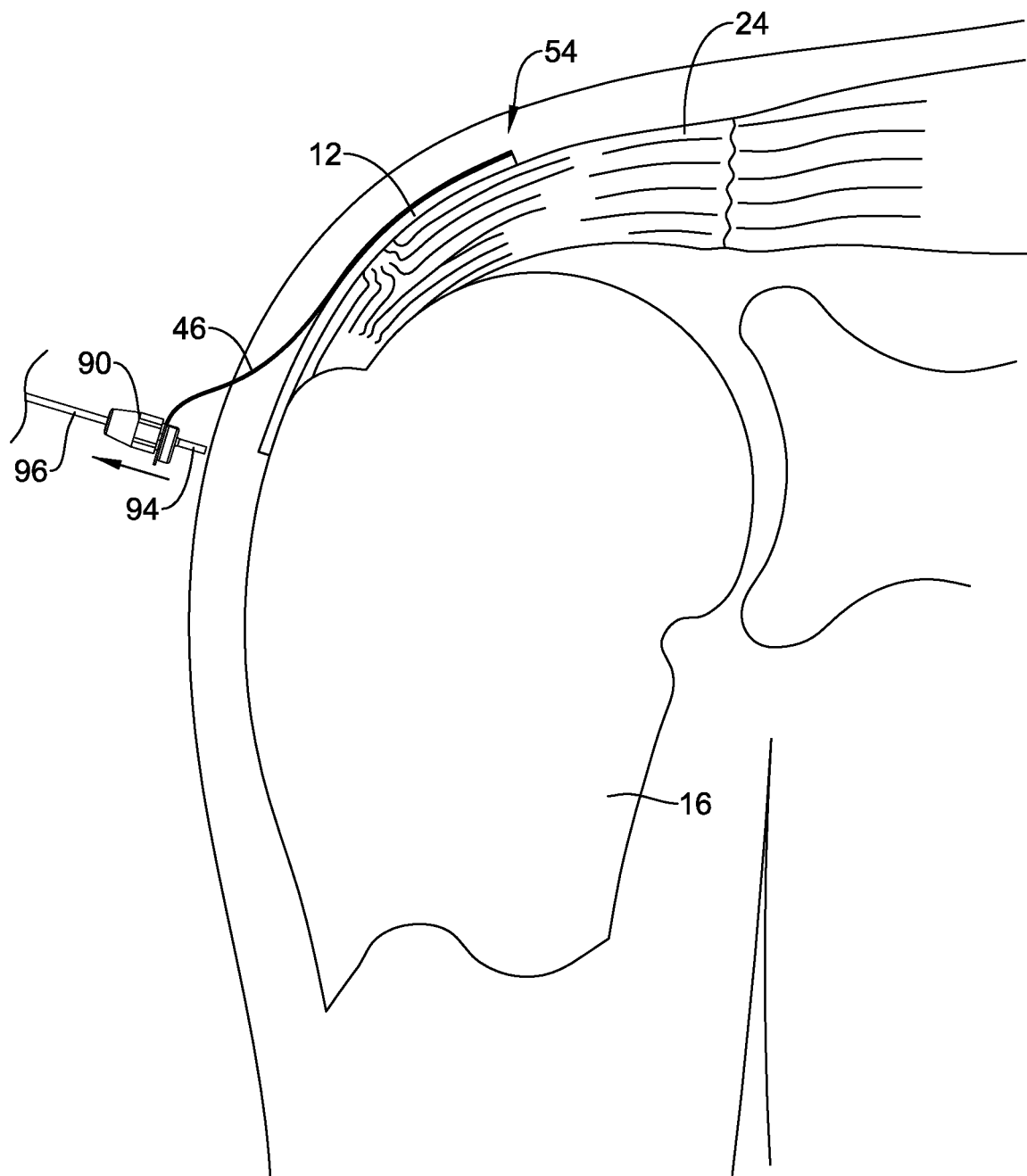

Once the implant 12 has been sufficiently affixed to the target site, the clinician may detach the frame 46 from the implant 12 (within the body) and remove it from the body via the insertion site. For example, FIG. 18 shows the detachment and removal of the frame 46 from the implant 12 (within the body) after the implant has been affixed (e.g., via staples) to the target site. In some instances, the clinician may detach and remove frame 46 from the implant 12 and the body via application of a withdrawal force to the frame 46. The withdrawal force made be applied via the tether 96. For example, a clinician may pull on the tether 96 (the proximal end of which may be positioned outside of the body), thereby applying a withdrawal force to frame 46. Once the withdrawal force reaches a threshold level (as discussed above), the frame 46 will detach from implant 12. Further withdrawal of the tether 96 may be continued to pull frame 46 out of the body via the insertion site.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An implant delivery system, the implant delivery system comprising:
    a delivery shaft including a proximal portion, a distal portion and a lumen extending there between;
    a frame detachably coupled to the distal portion of the delivery shaft;
    a tack member coupled to the frame; and
    a sheath having a lumen, wherein the delivery shaft and the frame are slidably disposed within the lumen of the sheath;
    wherein the sheath constrains the frame in a contracted configuration within the lumen of the sheath.
2. The implant delivery system of claim 1, further comprising a tether member coupled to a proximal portion of the tack member.
3. The implant delivery system of claim 2, wherein the tether member extends within the lumen of the delivery shaft.
4. The implant delivery system of claim 1, wherein the frame includes a body portion and a plurality of attachment arms extending away from the body portion.
5. The implant delivery system of claim 2, wherein the tack member extends through an aperture in the body portion of the frame.
6. The implant delivery system of claim 5, wherein a distal end portion of the tack member is configured to engage with a bone.
7. The implant delivery system of claim 6, wherein retraction of the tether member is designed to disengage the tack member from a bone.
8. The implant delivery system of claim 7, wherein the distal end portion of the tack member includes a tapered region.
9. The implant delivery system of claim 2, wherein a proximal end portion of the tack member includes a bore extending along a longitudinal axis of the tack member.
10. The implant delivery system of claim 9, wherein a distal end portion of the tether member is secured within the bore of the tack member.
11. The implant delivery system of claim 4, wherein the plurality of attachment arms are configured to be attached to an implant.
12. The implant delivery system of claim 1, wherein the frame is configured to detach from the delivery shaft in vivo.
13. The implant of claim 2, wherein the tether is directly coupled to the frame.
14. The implant of claim 2, wherein the tether is indirectly coupled to the frame via a connection member.
15. The implant delivery system of any one of claim 14, wherein the frame further comprises a first aperture configured to couple with the connection member.
16. An implant delivery system, the implant delivery system comprising:
    a delivery shaft including a proximal portion, a distal portion and a lumen extending therebetween;
    a frame detachably coupled to the distal portion of the delivery shaft;
    a tack member coupled to the frame;
    a tether member coupled to a proximal portion of the tack member;
    wherein the tether member is indirectly coupled to the frame via a connection member; and
    a sheath having a lumen, wherein the delivery shaft and the frame are slidably disposed within the lumen of the sheath;
    wherein the sheath constrains the frame in a contracted configuration within the lumen of the sheath.
17. The implant delivery system of claim 16, wherein the tether member extends within the lumen of the delivery shaft.
18. The implant delivery system of claim 16, wherein the frame includes a body portion and a plurality of attachment arms extending away from the body portion.
19. The implant delivery system of claim 18, wherein the tack member extends through an aperture in the body portion of the frame.
20. The implant delivery system of claim 19, wherein a distal end portion of the tack member is configured to engage with a bone.
21. The implant delivery system of claim 20, wherein retraction of the tether member is designed to disengage the tack member from a bone.
22. The implant delivery system of claim 20, wherein the distal end portion of the tack member includes a tapered region.
23. The implant delivery system of claim 16, wherein a proximal end portion of the tack member includes a bore extending along a longitudinal axis of the tack member.
24. The implant delivery system of claim 23, wherein a distal end portion of the tether member is secured within the bore of the tack member.
25. The implant delivery system of claim 18, wherein the plurality of attachment arms are configured to be attached to an implant.

26. The implant delivery system of claim 16, wherein the frame is configured to detach from the delivery shaft in vivo.

27. The implant delivery system of claim 16, wherein the frame further comprises a first aperture configured to couple with the connection member.

28. The implant delivery system of claim 16, wherein the connection member includes a first profile and wherein the lumen of the delivery shaft includes a second profile, and wherein the first profile is configured to mate with the second profile.

29. The implant delivery system of claim 28, wherein the connection member engages with the distal portion of the delivery shaft such that manipulation of the delivery shaft causes manipulation of the connection member, wherein the connection member is configured to disengage from the delivery shaft, and wherein the connection member is configured to remain engaged to the frame after disengaging from the delivery shaft.

30. The implant delivery system of claim 16, wherein the tack member is stationary with respect to the connection member.

31. The implant delivery system of claim 16, wherein the tack member can translate with respect to the connection member.

32. The implant delivery system of claim 16, wherein the tack member includes a shaft having a circumferential surface and one or more protrusions extending radially away from the circumferential surface.

33. The implant delivery system of claim 32, wherein the one or more protrusions are configured to anchor the tack member beneath a layer of bone.

34. The implant delivery system of claim 32, wherein the one or more protrusions are spaced away from each other along the shaft.

35. The implant delivery system of claim 16, wherein the tack member includes a shaft formed from a first material and one or more fixation members disposed along the shaft, wherein the one or more fixation members are formed from a second material different from the first material.

36. The implant delivery system of claim 35, wherein the one or more fixation members extend radially away from a circumferential surface of the shaft.

37. The implant delivery system of claim 16, wherein the tether member extends within the lumen of the delivery shaft while the delivery shaft is attached to the frame, and wherein the tether member remains connected to the frame when the delivery shaft is detached from the frame.

38. The implant delivery system of claim 16, wherein manipulation of the delivery shaft relative to the sheath causes the frame to be advanced out of the lumen of the sheath such that the frame assumes an expanded configuration.

39. The implant delivery system of claim 1, wherein manipulation of the delivery shaft relative to the sheath causes the frame to be advanced out of the lumen of the sheath such that the frame assumes an expanded configuration.

* * * * *